United States Patent
Rothberg et al.

(10) Patent No.: US 11,655,504 B2
(45) Date of Patent: May 23, 2023

(54) HIGH INTENSITY LABELED REACTANT COMPOSITIONS AND METHODS FOR SEQUENCING

(71) Applicant: Quantum-Si Incorporated, Guilford, CT (US)

(72) Inventors: Jonathan M. Rothberg, Guilford, CT (US); Jeremy Lackey, Guilford, CT (US); Brian Reed, Madison, CT (US); Xinghua Shi, Madison, CT (US); Haidong Huang, Madison, CT (US); David Dodd, Guilford, CT (US)

(73) Assignee: Quantum-Si Incorporated, Guilford, CT (US)

(*) Notice: Subject to any disclaimer, the term of this patent is extended or adjusted under 35 U.S.C. 154(b) by 367 days.

(21) Appl. No.: 16/043,547

(22) Filed: Jul. 24, 2018

(65) Prior Publication Data

US 2019/0024168 A1    Jan. 24, 2019

Related U.S. Application Data

(60) Provisional application No. 62/536,426, filed on Jul. 24, 2017.

(51) Int. Cl.

| | | |
|---|---|---|
| *C12Q 1/6876* | (2018.01) | |
| *C12Q 1/6816* | (2018.01) | |
| *C12Q 1/6806* | (2018.01) | |
| *C07H 19/073* | (2006.01) | |
| *C07H 21/04* | (2006.01) | |

(Continued)

(52) U.S. Cl.
CPC ......... *C12Q 1/6876* (2013.01); *C07H 19/073* (2013.01); *C07H 19/173* (2013.01); *C07H 21/04* (2013.01); *C12Q 1/6806* (2013.01); *C12Q 1/6816* (2013.01); *C12Q 1/6869* (2013.01); *C12Q 2525/185* (2013.01);

(Continued)

(58) Field of Classification Search
None
See application file for complete search history.

(56) References Cited

U.S. PATENT DOCUMENTS

| | | | |
|---|---|---|---|
| 5,210,015 A | 5/1993 | Gelfand et al. | |
| 5,487,972 A | 1/1996 | Gelfand et al. | |

(Continued)

FOREIGN PATENT DOCUMENTS

| | | |
|---|---|---|
| CA | 2373385 C | 11/2000 |
| CA | 2457513 A1 | 3/2003 |

(Continued)

OTHER PUBLICATIONS

U.S. Appl. No. 61/069,247.*

(Continued)

*Primary Examiner* — Robert T. Crow
(74) *Attorney, Agent, or Firm* — Wolf, Greenfield & Sacks, P.C.

(57) ABSTRACT

Compositions useful for the detection of single molecules in a sample are provided. In some aspects, the disclosure provides a nucleic acid connected to a nucleotide and two or more luminescent labels. In some embodiments, the nucleic acids described herein comprise one or more structural features that provide enhanced fluorescence intensity. In some aspects, methods of sequencing using the labeled nucleotides of the disclosure are provided.

18 Claims, 34 Drawing Sheets

Specification includes a Sequence Listing.

(51) Int. Cl.
*C07H 19/173* (2006.01)
*C12Q 1/6869* (2018.01)

(52) U.S. Cl.
CPC . *C12Q 2525/197* (2013.01); *C12Q 2525/313* (2013.01); *C12Q 2563/103* (2013.01); *C12Q 2600/16* (2013.01)

(56) References Cited

U.S. PATENT DOCUMENTS

| | | | |
|---|---|---|---|
| 5,594,117 A * | 1/1997 | Urdea | C07F 9/65515 435/6.11 |
| 5,707,804 A | 1/1998 | Mathies et al. | |
| 5,851,840 A | 12/1998 | Sluka et al. | |
| 6,133,445 A | 10/2000 | Waggoner et al. | |
| 6,153,442 A | 11/2000 | Pirio et al. | |
| 6,248,518 B1 | 6/2001 | Parkhurst et al. | |
| 6,255,083 B1 | 7/2001 | Williams | |
| 6,399,335 B1 | 6/2002 | Kao et al. | |
| 6,444,682 B1 * | 9/2002 | Simmonds | G01N 33/5308 514/274 |
| 6,762,048 B2 | 7/2004 | Williams | |
| 6,787,308 B2 | 9/2004 | Balasubramanian et al. | |
| 6,846,638 B2 | 1/2005 | Shipwash | |
| 6,869,764 B2 | 3/2005 | Williams et al. | |
| 6,936,702 B2 | 8/2005 | Williams et al. | |
| 7,041,812 B2 | 5/2006 | Kumar et al. | |
| 7,052,847 B2 | 5/2006 | Korlach et al. | |
| 7,056,661 B2 | 6/2006 | Korlach et al. | |
| 7,057,026 B2 | 6/2006 | Barnes et al. | |
| 7,229,799 B2 | 6/2007 | Williams | |
| 7,361,466 B2 | 4/2008 | Korlach et al. | |
| 7,405,281 B2 | 7/2008 | Xu et al. | |
| 7,625,701 B2 | 12/2009 | Williams et al. | |
| 7,968,702 B2 | 6/2011 | Wegener et al. | |
| 7,973,146 B2 | 7/2011 | Shen et al. | |
| 8,034,623 B2 | 10/2011 | Oh et al. | |
| 8,084,734 B2 | 12/2011 | Vertes et al. | |
| 8,133,702 B2 | 3/2012 | Shen et al. | |
| 8,148,516 B2 | 4/2012 | Williams et al. | |
| 8,153,375 B2 | 4/2012 | Travers et al. | |
| 8,192,961 B2 | 6/2012 | Williams | |
| 8,252,910 B2 | 8/2012 | Korlach et al. | |
| 8,257,954 B2 | 9/2012 | Clark et al. | |
| 8,309,330 B2 | 11/2012 | Travers et al. | |
| 8,354,252 B2 | 1/2013 | Wegener et al. | |
| 8,383,791 B1 * | 2/2013 | McDowell | C12Q 1/6827 536/23.1 |
| 8,420,366 B2 | 4/2013 | Clark et al. | |
| 8,455,193 B2 | 6/2013 | Travers et al. | |
| 8,530,154 B2 | 9/2013 | Williams | |
| 8,581,179 B2 | 11/2013 | Franzen | |
| 8,846,881 B2 | 9/2014 | Korlach et al. | |
| 8,906,614 B2 | 12/2014 | Wegener et al. | |
| 8,927,212 B2 | 1/2015 | Kong et al. | |
| 8,980,584 B2 | 3/2015 | Williams | |
| 9,062,091 B2 | 6/2015 | Bjornson et al. | |
| 9,404,146 B2 | 8/2016 | Travers et al. | |
| 9,435,810 B2 | 9/2016 | Havranek et al. | |
| 9,464,107 B2 | 10/2016 | Wegener et al. | |
| 9,542,527 B2 | 1/2017 | Travers et al. | |
| 9,551,031 B2 | 1/2017 | Korlach et al. | |
| 9,551,660 B2 | 1/2017 | Kong et al. | |
| 9,566,335 B1 | 2/2017 | Emili et al. | |
| 9,582,640 B2 | 2/2017 | Travers et al. | |
| 9,600,626 B2 | 3/2017 | Travers et al. | |
| 9,678,080 B2 | 6/2017 | Bjornson et al. | |
| 9,719,073 B2 | 8/2017 | Emig et al. | |
| 9,845,501 B2 | 12/2017 | Williams | |
| 9,879,319 B2 | 1/2018 | Korlach et al. | |
| 9,910,956 B2 | 3/2018 | Travers et al. | |
| 9,957,291 B2 | 5/2018 | Sebo et al. | |
| 10,023,605 B2 | 7/2018 | Bjornson et al. | |
| 10,066,258 B2 | 9/2018 | Kong et al. | |
| 10,150,872 B2 | 12/2018 | Zheng et al. | |
| 10,161,002 B2 | 12/2018 | Korlach et al. | |
| 10,174,363 B2 | 1/2019 | Rothberg et al. | |
| 10,481,162 B2 | 11/2019 | Emili et al. | |
| 10,544,449 B2 | 1/2020 | Shen et al. | |
| 10,545,153 B2 | 1/2020 | Marcotte et al. | |
| 10,570,445 B2 | 2/2020 | Kong et al. | |
| 10,676,788 B2 | 6/2020 | Shen et al. | |
| 10,745,750 B2 | 8/2020 | Korlach et al. | |
| 10,787,573 B2 | 9/2020 | Zheng et al. | |
| 11,001,875 B2 | 5/2021 | Rothberg et al. | |
| 2002/0182625 A1 * | 12/2002 | McGall | C07H 19/06 544/320 |
| 2003/0138809 A1 | 7/2003 | Williams et al. | |
| 2003/0143591 A1 | 7/2003 | Davies et al. | |
| 2005/0014154 A1 | 1/2005 | Weizenegger | |
| 2005/0042633 A1 | 2/2005 | Williams | |
| 2005/0266456 A1 | 12/2005 | Williams et al. | |
| 2007/0072196 A1 | 3/2007 | Xu et al. | |
| 2007/0219367 A1 | 9/2007 | Shchepinov et al. | |
| 2009/0068645 A1 | 3/2009 | Sibson | |
| 2009/0104614 A1 * | 4/2009 | Tsourkas | C12Q 1/6818 435/6.11 |
| 2009/0117540 A1 | 5/2009 | Sorge | |
| 2009/0233302 A1 | 9/2009 | Wegener et al. | |
| 2009/0263327 A1 | 10/2009 | Achilefu et al. | |
| 2009/0263802 A1 | 10/2009 | Drmanac | |
| 2010/0009872 A1 | 1/2010 | Eid et al. | |
| 2010/0029494 A1 | 2/2010 | Cherkasov et al. | |
| 2010/0034750 A1 | 2/2010 | Perfect et al. | |
| 2010/0035254 A1 | 2/2010 | Williams | |
| 2010/0093553 A1 | 4/2010 | Park et al. | |
| 2010/0129822 A1 * | 5/2010 | Siva | C12Q 1/6853 435/6.11 |
| 2010/0152424 A1 | 6/2010 | Korlach et al. | |
| 2010/0317005 A1 | 12/2010 | Hardin et al. | |
| 2011/0003343 A1 | 1/2011 | Nikiforov et al. | |
| 2011/0165652 A1 | 7/2011 | Hardin et al. | |
| 2011/0212437 A1 | 9/2011 | Emig et al. | |
| 2011/0256549 A1 | 10/2011 | Gaylord et al. | |
| 2011/0281776 A1 | 11/2011 | Eshoo et al. | |
| 2012/0322692 A1 | 12/2012 | Pham et al. | |
| 2013/0240359 A1 | 9/2013 | Turner et al. | |
| 2013/0316912 A1 | 11/2013 | Bjornson et al. | |
| 2014/0094375 A1 | 4/2014 | Kamtekar et al. | |
| 2015/0050659 A1 | 2/2015 | Sebo et al. | |
| 2015/0293022 A1 | 10/2015 | Buckhout-White et al. | |
| 2015/0330987 A1 | 11/2015 | Bjornson et al. | |
| 2017/0136433 A1 | 5/2017 | Sun et al. | |
| 2017/0362651 A1 | 12/2017 | Rothberg et al. | |
| 2018/0211003 A1 | 7/2018 | Travers et al. | |
| 2018/0299460 A1 | 10/2018 | Emili | |
| 2018/0346507 A1 | 12/2018 | Sebo et al. | |
| 2019/0010183 A1 | 1/2019 | Bjornson et al. | |
| 2019/0249153 A1 | 8/2019 | Kamtekar et al. | |
| 2019/0330688 A1 | 10/2019 | Rothberg et al. | |
| 2020/0031861 A1 | 1/2020 | Rothberg et al. | |
| 2020/0141944 A1 | 5/2020 | Emili et al. | |
| 2020/0148727 A1 | 5/2020 | Tullman et al. | |
| 2020/0232017 A1 | 7/2020 | Rothberg et al. | |

FOREIGN PATENT DOCUMENTS

| | | |
|---|---|---|
| CN | 1373813 A | 10/2002 |
| CN | 1771336 A | 5/2006 |
| CN | 1938328 A | 3/2007 |
| CN | 101346472 A | 1/2009 |
| CN | 101434988 A | 5/2009 |
| CN | 101636406 A | 1/2010 |
| CN | 102124128 A | 7/2011 |
| CN | 102329884 A | 1/2012 |
| CN | 102782159 A | 11/2012 |
| CN | 103866010 A | 6/2014 |
| CN | 105001292 A | 10/2015 |
| EP | 1681356 A1 | 7/2006 |
| EP | 1421213 B1 | 2/2010 |
| EP | 1179085 B1 | 5/2010 |
| EP | 2226330 A1 | 9/2010 |
| EP | 2263087 A1 | 12/2010 |
| EP | 2814953 | 12/2014 |

(56) References Cited

FOREIGN PATENT DOCUMENTS

| | | |
|---|---|---|
| GB | 2398383 A | 8/2004 |
| JP | H07-502992 A | 3/1995 |
| JP | 2002-543847 A | 12/2002 |
| JP | 2005-507674 A | 3/2005 |
| JP | 2009-518009 A | 5/2009 |
| JP | 2015-073523 A | 4/2015 |
| JP | 2016-011429 A | 1/2016 |
| WO | WO 93/09128 A1 | 5/1993 |
| WO | WO 00/70073 A1 | 11/2000 |
| WO | WO 01/09389 A2 | 2/2001 |
| WO | WO 03/089670 A2 | 10/2003 |
| WO | WO 03/102239 A2 | 12/2003 |
| WO | WO 2004/096997 A2 | 11/2004 |
| WO | WO 2005/044836 A2 | 5/2005 |
| WO | WO 2007/015168 A2 | 2/2007 |
| WO | WO 2007/041342 A2 | 4/2007 |
| WO | WO 2007/064905 A2 | 6/2007 |
| WO | WO 2007/070572 A2 | 6/2007 |
| WO | WO 2009/114182 A1 | 9/2009 |
| WO | WO 2010/065322 A1 | 6/2010 |
| WO | WO 2010/115016 A2 | 10/2010 |
| WO | WO 2010/117420 A2 | 10/2010 |
| WO | WO 2011/150852 A1 | 12/2011 |
| WO | WO 2012/027625 A2 | 1/2012 |
| WO | WO 2016/187580 A1 | 11/2016 |
| WO | WO 2017/201514 A1 | 11/2017 |
| WO | WO 2019/023257 A1 | 1/2019 |
| WO | WO 2019/040825 A1 | 2/2019 |

OTHER PUBLICATIONS

PCT/US2019/041717, Nov. 13, 2019, International Search Report and Written Opinion.
PCT/US2018/043526, Feb. 6, 2020, International Preliminary Report on Patentability.
U.S. Appl. No. 15/600,979, filed May 22, 2017, Rothberg et al.
U.S. Appl. No. 15/161,125, filed May 20, 2016, Rothberg et al.
PCT/US2017/033706, Sep. 12, 2017, International Search Report and Written Opinion.
PCT/US2017/033706, Nov. 29, 2018, International Preliminary Report on Patentability.
PCT/US2018/043526, Oct. 3, 2018, International Search Report and Written Opinion.
PCT/US2019/041717, Sep. 20, 2019, Invitation to Pay Additional Fee.
International Search Report and Written Opinion for Application No. PCT/US2019/041717 dated Nov. 13, 2019.
International Preliminary Report on Patentability for Application No. PCT/US2018/043526 dated Feb. 6, 2020.
Koushik et al., Cerulean, Venus, and VenusY67C FRET reference standards. Biophys J. Dec. 15, 2006;91(12):L99-L101. doi: 10.1529/biophysj.106.096206. Epub Oct. 13, 2006. PMID: 17040988; PMCID: PMC1779932.
Saito et al., Dual-labeled oligonucleotide probe for sensing adenosine via FRET: a novel alternative to SNPs genotyping. Chem Commun (Camb). Jun. 7, 2007;(21):2133-5. doi: 10.1039/b618465k. Epub Feb. 28, 2007. PMID: 17520113.
Sato et al., Polyproline-rod approach to isolating protein targets of bioactive small molecules: isolation of a new target of indomethacin. J Am Chem Soc. Jan. 31, 2007;129(4):873-80. doi: 10.1021/ja0655643. PMID: 17243824.
Stryer et al., Energy transfer: a spectroscopic ruler. Proc Natl Acad Sci U S A. Aug. 1967;58(2):719-26. doi: 10.1073/pnas.58.2.719. PMID: 5233469; PMCID: PMC335693.
Williams et al., An artificial processivity clamp made with streptavidin facilitates oriented attachment of polymerase-DNA complexes to surfaces. Nucleic Acids Res. Oct. 2008;36(18):e121. doi: 10.1093/nar/gkn531. Epub Aug. 22, 2008. PMID: 18723573; PMCID: PMC2566871.
U.S. Appl. No. 61/069,247, Korlach et al., filed Mar. 13, 2008.
U.S. Appl. No. 61/979,724, filed Apr. 14, 2014.
International Search Report and Written Opinion for International Application No. PCT/US2017/033706 dated Sep. 12, 2017.
International Preliminary Report on Patentability for International Application No. PCT/US2017/033706 dated Nov. 29, 2018.
International Search Report and Written Opinion for International Application No. PCT/US2018/043526 dated Oct. 3, 2018.
Invitation to Pay Additional Fees for Application No. PCT/US2019/041717 dated Sep. 20, 2019.
Brown et al., Synthesis of a modified thymidine monomer for site-specific incorporation of reportergroups into oligonucleotides. Tetrahedron Letters. 2001;42:2587-2591.
Cheng-Yao, DNA polymerases drive DNA sequencing-by-synthesis technologies: both past and present. Frontiers in Microbiology. 2014. 10 pages.
Kretschy et al., Comparison of the sequence-dependent fluorescence of the cyanine dyes Cy3, Cy5, DyLight DY547 and DyLight DY647 on single-stranded DNA. PLoS One. Jan. 15, 2014;9(1):e85605. doi: 10.1371/journal.pone.0085605. eCollection 2014.
Kumar et al., Terminal phosphate labeled nucleotides: synthesis, applications, and linker effect on incorporation by DNA polymerases. Nucleosides Nucleotides Nucleic Acids. Nov. 2005; 24(5-7):401-8.
Takkellapati et al., Synthesis of aminomethyl- and bis-aminomethyl-fluorescein energy transfer terminators. Nucleosides Nucleotides Nucleic Acids. Dec. 2007; 26(10-12):1467-70.
International Preliminary Report on Patentability for Application No. PCT/US2019/041717 dated Jan. 28, 2021.
Extended European Search Report dated May 6, 2021 for Application No. EP 18837972.1.
U.S. Appl. No. 16/212,724, filed Dec. 7, 2018, Rothberg et al.
U.S. Appl. No. 16/510,794, filed Jul. 12, 2019, Rothberg et al.
PCT/US2019/041717, Jan. 28, 2021, International Preliminary Report on Patentability.
Invitation to Pay Additional Fees for International Application No. PCT/US2020/014856 dated May 8, 2020.
International Search Report and Written Opinion for International Application No. PCT/US2020/014856 dated Jun. 30, 2020.
International Preliminary Report on Patentability for International Application No. PCT/US2020/014856 dated Aug. 5, 2021.
Bunt et al., FRET from single to multiplexed signaling events. Biophys Rev. 2017;9:119-29. Epub Mar. 23, 2017.

* cited by examiner

SEQUENCE LISTING

```
<160> NUMBER OF SEQ ID NOS: 19

<210> SEQ ID NO 1
<211> LENGTH: 35
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (21)..(22)
<223> OTHER INFORMATION: modified by linker
<220> FEATURE:
<221> NAME/KEY: misc_feature
<222> LOCATION: (30)..(31)
<223> OTHER INFORMATION: modified by linker

<400> SEQUENCE: 1
cacgcgtgga accctcgatt aattgcctta attgc                              35

<210> SEQ ID NO 2
<211> LENGTH: 37
<212> TYPE: DNA
<213> ORGANISM: Artificial Sequence
<220> FEATURE:
<223> OTHER INFORMATION: Synthetic Polynucleotide

<400> SEQUENCE: 2
gcaatttaag gcaatttaat cgagggttcc acgcgtg                            37

<210> SEQ ID NO 3
<211> LENGTH: 29
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (17)..(18)
<223> OTHER INFORMATION: modified by iCy3

<400> SEQUENCE: 3
ccacgcgtgg aaccctttg ggatttcca                                      29

<210> SEQ ID NO 4
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 4
tggatcccaa gggttccacg cgtgg                                         25

<210> SEQ ID NO 5
<211> LENGTH: 63
<212> TYPE: DNA
<213> ORGANISM: Artificial Sequence
<220> FEATURE:
```

<223> OTHER INFORMATION: Synthetic Polynucleotide
<220> FEATURE:
<221> NAME/KEY: misc_feature
<222> LOCATION: (30)..(30)
<223> OTHER INFORMATION: modified by linker
<220> FEATURE:
<221> NAME/KEY: misc_feature
<222> LOCATION: (50)..(50)
<223> OTHER INFORMATION: modified by linker

<400> SEQUENCE: 5
cgctagtccg tgagtaccca caaatgtttt ttacatttga gtatacattt tttgtataca    60
ggg    63

<210> SEQ ID NO 6
<211> LENGTH: 16
<212> TYPE: DNA
<213> ORGANISM: Artificial Sequence
<220> FEATURE:
<223> OTHER INFORMATION: Synthetic Polynucleotide

<400> SEQUENCE: 6
tactcacgga ctagcg    16

<210> SEQ ID NO 7
<211> LENGTH: 9
<212> TYPE: DNA
<213> ORGANISM: Artificial Sequence
<220> FEATURE:
<223> OTHER INFORMATION: Synthetic Polynucleotide

<400> SEQUENCE: 7 tatgggtag    9

<210> SEQ ID NO 8
<211> LENGTH: 9
<212> TYPE: DNA
<213> ORGANISM: Artificial Sequence
<220> FEATURE:
<223> OTHER INFORMATION: Synthetic Polynucleotide

<400> SEQUENCE: 8 ctacccata    9

<210> SEQ ID NO 9
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 9
ccacgcgtgg tagggatcca    20

<210> SEQ ID NO 10
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 10
tggatcccta ccacgcgtgg    20

<210> SEQ ID NO 11
<211> LENGTH: 17

```
<212> TYPE: DNA
<213> ORGANISM: Artificial Sequence
<220> FEATURE:
<223> OTHER INFORMATION: Synthetic Polynucleotide

<400> SEQUENCE: 11
agcttgggca actgtta                                                   17

<210> SEQ ID NO 12
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 12
taacagttgc ccaagct                                                   17

<210> SEQ ID NO 13
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 13
gcaatttaac gatggttcca cgcgtg                                         26

<210> SEQ ID NO 14
<211> LENGTH: 25
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (20)..(21)
<223> OTHER INFORMATION: modified by linker

<400> SEQUENCE: 14
cacgcgtgga accatcgtta attgc                                          25

<210> SEQ ID NO 15
<211> LENGTH: 28
<212> TYPE: DNA
<213> ORGANISM: Artificial Sequence
<220> FEATURE:
<223> OTHER INFORMATION: Synthetic Polynucleotide

<400> SEQUENCE: 15
gtgcgctacc ttgggaatat tgcttacg                                       28

<210> SEQ ID NO 16
<211> LENGTH: 43
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (5)..(6)
<223> OTHER INFORMATION: modified by linker
```

<400> SEQUENCE: 16
cgttaattgc tttttgcaat gcaatattcc caaggtagcg cac        43

<210> SEQ ID NO 17
<211> LENGTH: 37
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (22)..(22)
<223> OTHER INFORMATION: modified by linker
<220> FEATURE:
<221> NAME/KEY: misc_feature
<222> LOCATION: (32)..(32)
<223> OTHER INFORMATION: modified by linker

<400> SEQUENCE: 17
cacgcgtgga accctcgatt atattgcctt atattgc        37

<210> SEQ ID NO 18
<211> LENGTH: 35
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (5)..(6)
<223> OTHER INFORMATION: modified by linker
<220> FEATURE:
<221> NAME/KEY: misc_feature
<222> LOCATION: (14)..(15)
<223> OTHER INFORMATION: modified by linker

<400> SEQUENCE: 18
cgttaattcc gttaattagc tcccaaggtg cgcac        35

<210> SEQ ID NO 19
<211> LENGTH: 37
<212> TYPE: DNA
<213> ORGANISM: Artificial Sequence
<220> FEATURE:
<223> OTHER INFORMATION: Synthetic Polynucleotide

<400> SEQUENCE: 19
gtgcgcacct tgggagctaa tttaacggaa tttaacg        37

HIGH INTENSITY LABELED REACTANT COMPOSITIONS AND METHODS FOR SEQUENCING

RELATED APPLICATIONS

This application claims priority under 35 U.S.C. § 119(e) to U.S. Provisional Patent Application No. 62/536,426, filed Jul. 24, 2017, which is hereby incorporated by reference in its entirety.

FIELD OF THE APPLICATION

The present application is directed generally to brightly labeled reactant compositions and methods of using the same for the detection of single molecules.

BACKGROUND

Advancements in next-generation sequencing technologies have made it possible to conduct massively parallel analysis of single molecules, which has fundamentally altered the landscape of life science research. Some of these techniques involve monitoring a biological reaction in real-time using luminescently labeled reaction components. The labels are illuminated with a light source to cause luminescence, and the luminescent light is detected with a photodetector. These events can be recorded and analyzed to identify individual reaction components based on corresponding luminescent properties. In identifying a specific type of labeled molecule among a plurality of types, it is critical that each type possess unique and readily identifiable luminescent properties. Furthermore, these parameters can be determinative of instrumental requirements such as excitation source power and overall instrument size.

SUMMARY

Aspects of the technology disclosed herein relate to labeled reaction components comprising two or more luminescent labels separated by a linker (e.g., a constrained linker). In some embodiments, the application relates to the separation of luminescent labels to prevent attenuation of detectable signals due to label-label interaction. In some aspects, the application provides labeled nucleotides comprising a nucleotide (e.g., a nucleoside polyphosphate) connected to two or more luminescent labels via a linker. In some aspects, the application provides compositions, methods, and kits for sequencing a template nucleic acid.

In some aspects, the application provides labeled nucleotides comprising a nucleotide (e.g., a nucleoside polyphosphate) connected to two or more luminescent labels via a linker. In some embodiments, the nucleotide is configured for use as a substrate in a polymerization reaction. In some embodiments, labeled nucleotides of the application comprise two or more luminescent labels separated from one another by a minimum distance. In some embodiments, each luminescent label is at least 5 angstroms separated from any other luminescent label. For example, in some embodiments, each luminescent label is at least 5, at least 10, at least 15, at least 20, at least 25, at least 30, at least 40, or at least 50 angstroms separated from any other luminescent label. In some embodiments, each luminescent label comprises a center of mass that is at least 5 angstroms separated from the center of mass of any other luminescent label.

In some embodiments, labeled nucleotides of the application comprise one or more luminescent labels attached to the linker via a spacer molecule. In some embodiments, the spacer molecule connects a luminescent label to an attachment site on the linker. In some embodiments, a luminescent label is attached to the linker via a spacer molecule that comprises at least 8 contiguous atoms between the luminescent label and the attachment site on the linker. In some embodiments, the spacer molecule comprises fewer than 50, fewer than 40, fewer than 30, or fewer than 20 contiguous atoms between the luminescent label and the attachment site on the linker. In some embodiments, a luminescent label is integrated into the linker.

In some embodiments, the linker is an oligomer (e.g., an oligomeric linker, or a polymeric linker). In some embodiments, the oligomer comprises monomeric units. In some embodiments, the oligomer comprises two or more different types of monomeric units. In some embodiments, the oligomer comprises a plurality of the same type of monomeric unit (e.g., the oligomer is a polymer of one type of monomeric units). In some embodiments, the oligomer comprises a first region with a plurality of a first type of monomeric units and a second region with a plurality of a second type of monomeric units. In some embodiments, the oligomer comprises a plurality of different regions (e.g., 2, 3, 4, 5, or more) each comprising a plurality of a different type of monomeric units. In some embodiments, the oligomer comprises at least 5 monomeric units. In some embodiments, the oligomer comprises at least 10 monomeric units. In some embodiments, the oligomer comprises fewer than 150, fewer than 100, or fewer than 50 monomeric units (e.g., at least 5 monomeric units and fewer than 200, 150, 100, 75, 50, or 25 monomeric units; at least 10 monomeric units and fewer than 200, 150, 100, 75, 50, or 25 monomeric units).

In some embodiments, where the linker is an oligomer (e.g., an oligomeric linker, a polymeric linker), each luminescent label is separated from each other label by at least 5 monomeric units of the oligomer. In some embodiments, a first luminescent label is integrated into the linker at a first position that is at least 5 monomeric units separated from a second position at which a second luminescent label is integrated into or attached to the linker. In some embodiments, where adjacent luminescent labels are integrated into the linker, the labels can be separated by fewer than 5 monomeric units. In some embodiments, each luminescent label is attached to the linker at an attachment site that is at least 5 monomeric units (e.g., at least 6, at least 8, at least 10, at least 12, at least 14, at least 16, at least 18, at least 20, or more, monomeric units) separated from any other attachment site. In some embodiments, each luminescent label is attached at an attachment site that is at least 5 monomeric units and fewer than 40 monomeric units (e.g., fewer than 38, fewer than 36, fewer than 34, fewer than 32, fewer than 30, fewer than 28, fewer than 26, fewer than 24, fewer than 22, or fewer than 20 monomeric units) separated from any other attachment site. In some embodiments, a luminescent label is integrated into the linker in between two sequential monomeric units of the oligomer (e.g., covalently connecting two adjacent monomeric units of an oligomer).

In some embodiments, a linker is sufficiently rigid to prevent interactions between two or more labels connected to the linker. In some embodiments, the rigidity of the linker is sufficient to preserve at least 75%, at least 80%, at least 85%, at least 90%, at least 95%, for example 95-100% (e.g., around 95%, around 96%, around 97%, around 98%, around 99%, around 100%) of the intensity of each label relative to their intensity when present as a single label attached to the same linker.

In some embodiments, the linker is a peptide. In some embodiments, the amino acid composition of the peptide provides structural rigidity (e.g., due to the presence of one or more polyproline segments in the peptide linker). In some embodiments, 90% or more (e.g., all) of the peptide linker consists of a polyproline polymer. In some embodiments, the peptide rigidity is provided by constraining the peptide via chemical modification. For example, in some embodiments, the peptide comprises one or more cyclized segments. In some embodiments, the peptide is a cyclized peptide (e.g., a stapled peptide, an end-to-end cyclized peptide, etc.). In some embodiments, sufficient peptide rigidity can be provided by incorporating a combination of one or more rigid amino acid polymer segments and one or more chemically modified amino acid polymer segments.

In some embodiments, the linker is a polysaccharide (e.g., heparin, heparin sulfate, polyglucose, polylactose, aminoglycosides, N-acetylaminoglycosides, and combinations thereof).

In some embodiments, the linker is a nucleic acid. In some embodiments, the nucleic acid comprises a deoxyribonucleic acid (DNA), a ribonucleic acid (RNA), a peptide nucleic acid (PNA), a locked nucleic acid (LNA), or a derivative thereof. In some embodiments, sufficient rigidity is provided by using one or more double stranded nucleic acid segments (e.g., separating two or more different labels). In some embodiments, sufficient rigidity is provided by one or more chemical modifications of a nucleic acid (e.g., of a single-stranded or a double-stranded nucleic acid, or of a nucleic acid comprising one or more single-stranded and one or more double-stranded segments). In some embodiments, a nucleic acid comprises a combination of one or more double-stranded segments and one or more chemically modified segments.

In some embodiments, the nucleic acid comprises a combination of one or more single-stranded and one or more double-stranded segments. A single-stranded segment can, in some embodiments, be present in the form of a loop (e.g., as in a stem-loop secondary structure described elsewhere herein). In some embodiments, a single-stranded segment is present in the form of an unpaired region within a double-stranded segment. For example, an internal loop can form within a double-stranded segment where one or more bases of one strand do not form base pairing interactions with one or more adjacent bases of the other strand. A further example of an unpaired region includes bulge loops, which can form within double-stranded segments where one strand includes one or more additional bases relative to the other strand. In some embodiments, single-stranded regions and double-stranded regions impart structural rigidity.

In some embodiments, a single-stranded region (e.g., an unpaired region) is at least 2 bases long (e.g., 2, 3, 4, 5, 6, 7, 8, 9, 10, or more, bases long). In some embodiments, a single-stranded region is between 2 and 10 bases long (e.g., between 2 and 8, between 4 and 10, or between 4 and 8, bases long). In some embodiments, a double-stranded region is between 2 and 40 bases long (e.g., between 2 and 20, between 2 and 10, between 10 and 40, between 10 and 30, between 10 and 20, between 20 and 40, or between 20 and 30, bases long).

In some embodiments, the nucleic acid comprises a first oligonucleotide strand attached to the two or more luminescent labels. In some embodiments, the two or more luminescent labels are attached at two or more attachment sites on the first oligonucleotide strand. In some embodiments, each luminescent label comprises a steric volume having a center point that is at least 5 angstroms separated from that of any other luminescent label. For example, in some embodiments, each luminescent label comprises a steric volume having a center point that is at least 6 angstroms, between about 5 to 10 angstroms, between about 6 to 10 angstroms, between about 10 to 15 angstroms, between about 15 to 20 angstroms, between about 20 to 25 angstroms, or between about 25 to 50 angstroms separated from that of any other luminescent label.

In some embodiments, the nucleic acid further comprises a second oligonucleotide strand hybridized with the first oligonucleotide strand. In some embodiments, the first oligonucleotide strand is attached to a nucleotide (e.g., a nucleoside polyphosphate). In some embodiments, the second oligonucleotide strand is attached to a nucleotide (e.g., a nucleoside polyphosphate).

In some embodiments, the two or more attachment sites are separated from one another by at least 5 bases (e.g., at least 5 nucleotides) on the first oligonucleotide strand. In some embodiments, the two or more attachment sites are separated from one another by at least 5 and fewer than 40 bases (e.g., between about 5 and 30 bases, between about 5 and 20 bases, between about 5 and 10 bases, between about 10 and 40 bases, between about 20 and 40 bases, or between about 30 and 40 bases) on the first oligonucleotide strand. In some embodiments, each attachment site is at least 2 bases separated from a guanine or a cytosine on the first oligonucleotide strand. In some embodiments, each attachment site occurs at an abasic site on the first oligonucleotide strand. In some embodiments, each attachment site occurs at a nucleobase of a nucleotide on the first oligonucleotide strand. In some embodiments, the nucleobase is selected from an A, T, or U nucleobase.

In some embodiments, the first oligonucleotide strand forms one or more (e.g., 1, 2, 3, 4, or more) stem-loops. In some embodiments, a loop region of each stem-loop comprises an attachment site of the two or more attachment sites. In some embodiments, the loop region of each stem-loop comprises at least 4 unpaired bases (e.g., 4, 5, 6, 7, 8, or more, unpaired bases). In some embodiments, the loop region comprises a sequence (e.g., a nucleotide sequence) having less than 33% G/C content.

In some aspects, labeled nucleotides of the disclosure comprise a nucleic acid linker comprising a first oligonucleotide strand attached to two or more branching oligonucleotide strands at a terminal end of the first oligonucleotide strand. In some embodiments, the first oligonucleotide strand is attached to the two or more branching oligonucleotide strands via a covalent coupling compound. In some embodiments, each branching oligonucleotide strand comprises at least one luminescent label. In some embodiments, the first oligonucleotide strand is hybridized with a second oligonucleotide strand. In some embodiments, the second oligonucleotide strand is attached to a nucleotide (e.g., a nucleoside polyphosphate). In some embodiments, each branching oligonucleotide strand is further hybridized with a complementary branching oligonucleotide strand.

In some embodiments, the covalent coupling compound is of a structure:

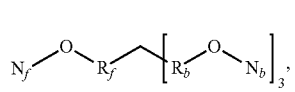

wherein $N_f$ is the first oligonucleotide strand; $N_b$ is a branching oligonucleotide strand; $R_f$ and $R_b$ are each, independent from one another, a bond or a linking group selected from the group consisting of substituted or unsubstituted alkylene; substituted or unsubstituted alkenylene; substituted or unsubstituted alkynylene; substituted or unsubstituted heteroalkylene; substituted or unsubstituted heteroalkenylene; substituted or unsubstituted heteroalkynylene; substituted or unsubstituted heterocyclylene; substituted or unsubstituted carbocyclylene; substituted or unsubstituted arylene; substituted or unsubstituted heteroarylene; and combinations thereof; and each instance of O is an oxygen atom of either a 5' phosphate group or a 3' hydroxyl group of an adjacent oligonucleotide strand.

In some aspects, labeled nucleotides of the disclosure comprise a nucleic acid linker comprising a first oligonucleotide component that comprises three or more oligonucleotide strands (e.g., 3, 4, 5, 6, or more, oligonucleotide strands) extending from a covalent coupling compound. In some embodiments, at least one of the three or more oligonucleotide strands is attached to a nucleotide (e.g., a nucleoside polyphosphate). In some embodiments, the first oligonucleotide component is hybridized with a second oligonucleotide component. In some embodiments, the second oligonucleotide component comprises at least one oligonucleotide strand attached to a luminescent label.

In some embodiments, labeled nucleotides of the disclosure are luminescently labeled with a fluorescent dye. In some embodiments, the fluorescent dye is a rhodamine dye, a BODIPY dye, or a cyanine dye.

In some embodiments, labeled nucleotides of the disclosure comprise a nucleotide (e.g., a nucleoside polyphosphate) that is at least 1 nm separated from any luminescent label of the two or more luminescent labels. In some embodiments, the nucleotide is separated from any luminescent label of the two or more luminescent labels by between approximately 1 and 10 nm (e.g., between approximately 2 and 10 nm, between approximately 4 and 10 nm, between approximately 6 and 10 nm, or between approximately 8 and 10 nm). In some embodiments, the nucleotide is separated from any luminescent label of the two or more luminescent labels by between approximately 2 and 20 nm (e.g., between approximately 6 and 20 nm, between approximately 10 and 20 nm, between approximately 12 and 20 nm, or between approximately 16 and 20 nm).

In some aspects, the disclosure provides methods of determining the sequence of a template nucleic acid. In some embodiments, the methods include a step comprising exposing a complex in a target volume, the complex comprising the template nucleic acid, a primer, and a polymerizing enzyme, to a plurality of types of luminescently labeled nucleotides provided by the application. In some embodiments, one or more of the plurality of types of luminescently labeled nucleotides comprise a nucleotide (e.g., a nucleoside polyphosphate) connected to two or more luminescent labels via a linker. In some embodiments, the linker is an oligomer that comprises at least 10 monomeric units. In some embodiments, each luminescent label is attached to the linker at an attachment site that is at least 5 monomeric units separated from any other attachment site. For example, in some embodiments, an attachment site is separated from any other attachment site by between about 5 and 30 monomeric units, between about 5 and 20 monomeric units, between about 5 and 10 monomeric units, between about 10 and 40 monomeric units, between about 20 and 40 monomeric units, or between about 30 and 40 monomeric units. In some embodiments, each luminescent label is at least 5 angstroms separated from any other luminescent label. For example, in some embodiments, each luminescent label is separated from any other luminescent label by approximately 5 to 10 angstroms, approximately 6 to 10 angstroms, approximately 10 to 15 angstroms, approximately 15 to 20 angstroms, approximately 20 to 25 angstroms, or approximately 25 to 50 angstroms. Accordingly, in some aspects, the disclosure provides methods of nucleic acid sequencing that utilize any of the luminescently labeled nucleotides described herein.

In some embodiments, the methods further comprise a step of directing a series of pulses of one or more excitation energies towards a vicinity of the target volume. In some embodiments, the methods further comprise a step of detecting a plurality of emitted photons from luminescently labeled nucleotides during sequential incorporation into a nucleic acid comprising the primer. In some embodiments, the methods further comprise a step of identifying the sequence of incorporated nucleotides by determining timing and optionally luminescent intensity and/or brightness of the emitted photons.

In some embodiments, four different types of nucleotides (e.g., adenine, guanine, cytosine, thymine/uracil) in a reaction mixture can each be labeled with one or more luminescent molecules (e.g., having two or more luminescent labels, as described herein). In some embodiments, each type of nucleotide can be connected to more than one of the same luminescent molecule (e.g., two or more of the same fluorescent dye connected to a nucleotide). In some embodiments, each luminescent molecule can be connected to more than one nucleotide (e.g., two or more of the same nucleotide). In some embodiments, more than one nucleotide can be connected (e.g., via a linker described herein) to more than one luminescent molecule.

In some embodiments, the luminescent labels among a set of four nucleotides can be selected from dyes comprising an aromatic or heteroaromatic compound and can be a pyrene, anthracene, naphthalene, acridine, stilbene, indole, benzindole, oxazole, carbazole, thiazole, benzothiazole, phenanthridine, phenoxazine, porphyrin, quinoline, ethidium, benzamide, cyanine, carbocyanine, salicylate, anthranilate, coumarin, fluorescein, rhodamine, or other like compound. Examples of dyes include xanthene dyes, such as fluorescein or rhodamine dyes, naphthalene dyes, coumarin dyes, acridine dyes, cyanine dyes, benzoxazole dyes, stilbene dyes, pyrene dyes, phthalocyanine dyes, phycobiliprotein dyes, squaraine dyes, BODIPY dyes, and the like.

In some aspects, the application provides kits for sequencing a template nucleic acid. In some embodiments, a kit comprises a plurality of types of luminescently labeled nucleotides as described herein. In some embodiments, each type of labeled nucleotide comprises two or more luminescent labels attached to one or more nucleotides (e.g., one or more nucleoside polyphosphates) via a linker. In some embodiments, the kit further comprises a polymerizing enzyme. In some embodiments, the kit further comprises a primer complementary to the template nucleic acid being sequenced.

In some aspects, the application provides nucleic acid sequencing reaction compositions. In some embodiments, the compositions comprise two or more (e.g., 2, 3, 4, or more) different types of luminescently labeled nucleotides in a reaction mixture. In some embodiments, each type of luminescently labeled nucleotide comprises a labeled nucleotide according to the present application. In some embodiments, the compositions further comprise a polymerizing enzyme. In some embodiments, the compositions further comprise a template nucleic acid. In some embodiments, the compositions further comprise a primer complementary to the template nucleic acid.

BRIEF DESCRIPTION OF THE DRAWINGS

The skilled artisan will understand that the figures, described herein, are for illustration purposes only. It is to be understood that, in some instances, various aspects of the invention may be shown exaggerated or enlarged to facilitate an understanding of the invention. In the drawings, like reference characters generally refer to like features, functionally similar and/or structurally similar elements throughout the various figures. The drawings are not necessarily to scale, emphasis instead being placed upon illustrating the principles of the teachings. The drawings are not intended to limit the scope of the present teachings in any way.

The features and advantages of the present invention will become more apparent from the detailed description set forth below when taken in conjunction with the drawings.

When describing embodiments in reference to the drawings, direction references ("above," "below," "top," "bottom," "left," "right," "horizontal," "vertical," etc.) may be used. Such references are intended merely as an aid to the reader viewing the drawings in a normal orientation. These directional references are not intended to describe a preferred or only orientation of an embodied device. A device may be embodied in other orientations.

As is apparent from the detailed description, the examples depicted in the figures (e.g., FIGS. 1-10) and further described for the purpose of illustration throughout the application describe non-limiting embodiments, and in some cases may simplify certain processes or omit features or steps for the purpose of clearer illustration.

Figure 1A:
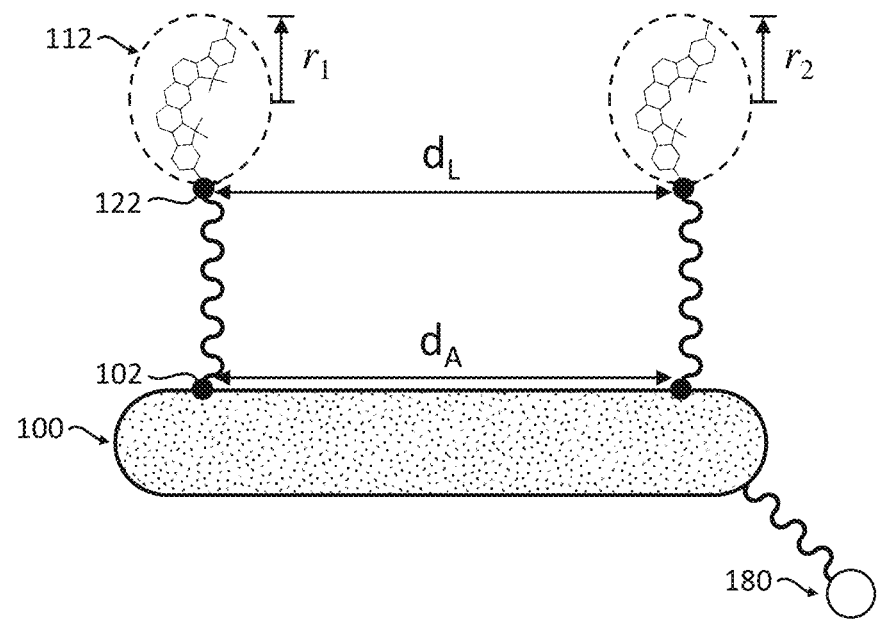

FIG. 1A is a diagram that generically depicts luminescent label separation on a brightly labeled reactant.

Figure 1B:
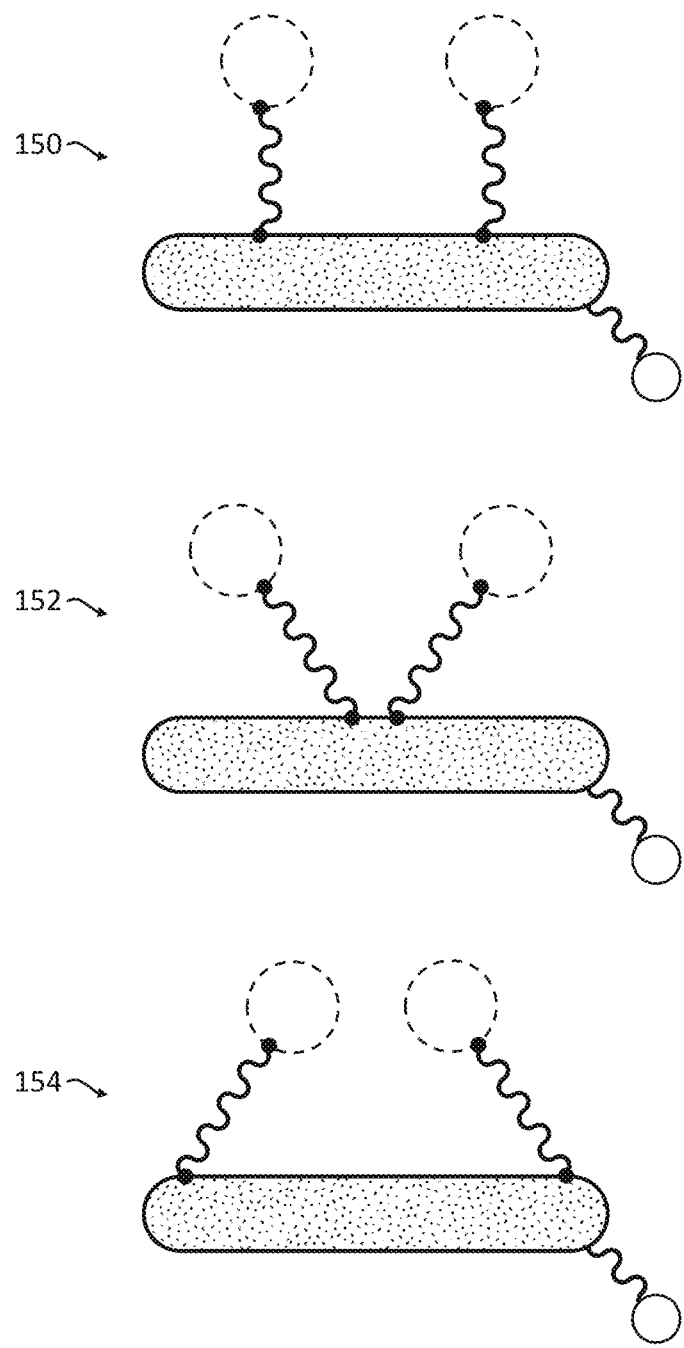

FIG. 1B depicts generic linker structures having different luminescent label attachment configurations.

Figure 2A:
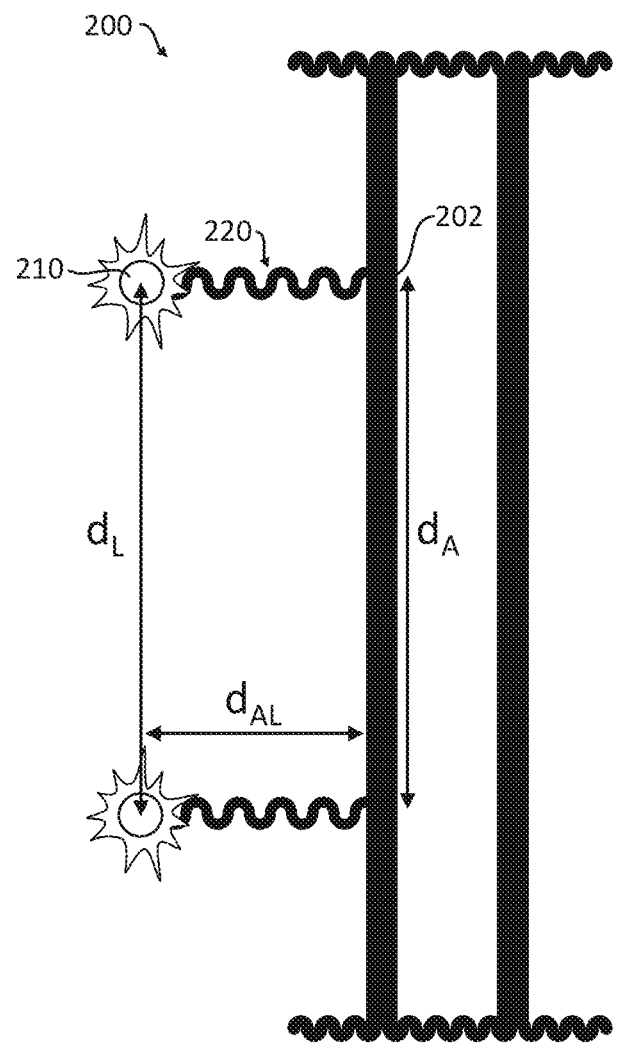

FIG. 2A is a diagram that generically depicts a nucleic acid linker attached to two luminescent labels.

Figure 2B:
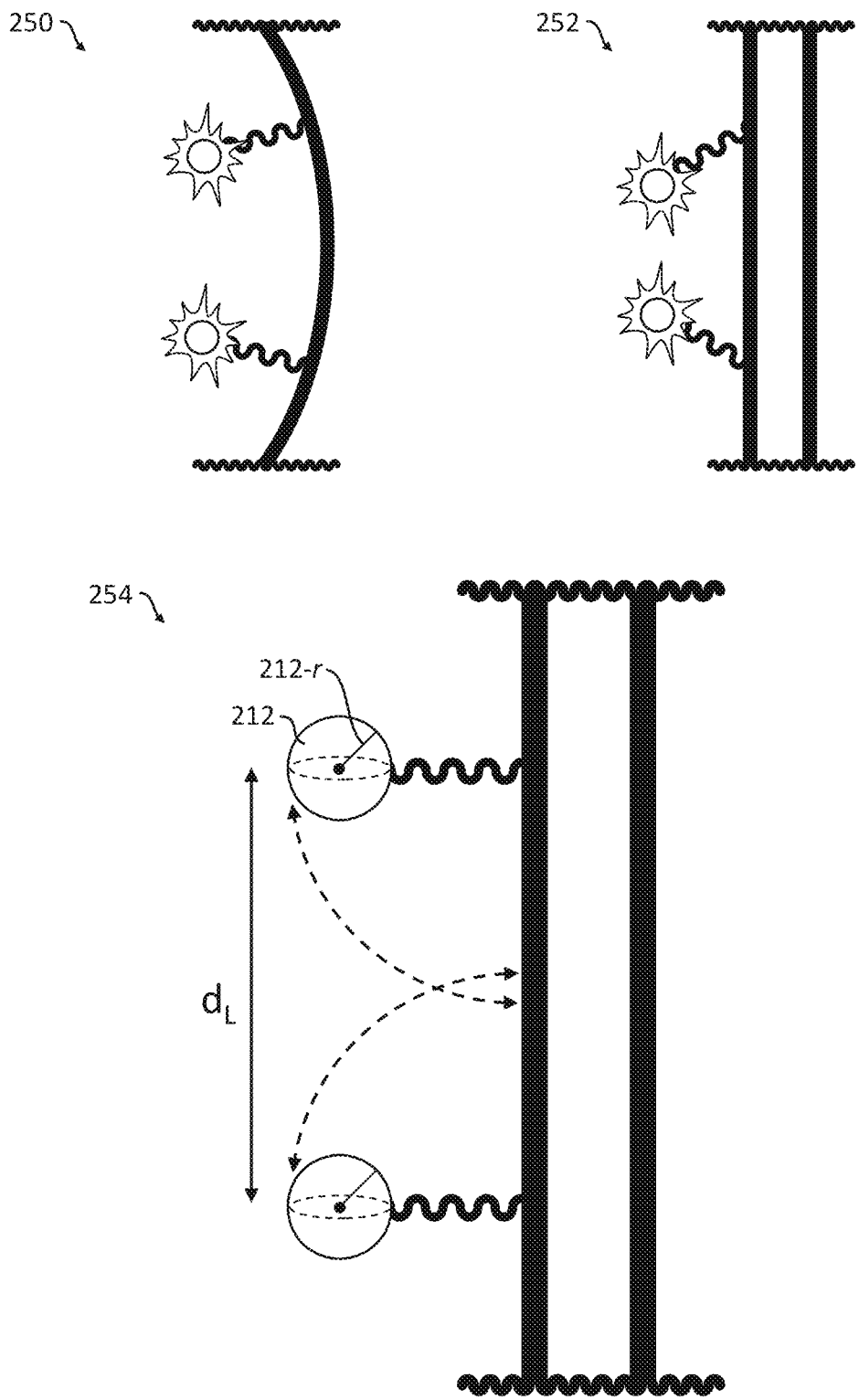

FIG. 2B depicts generic nucleic acids having differing strand configurations (top) and a diagram that generically depicts luminescent label spatial occupation (bottom).

Figure 2C:
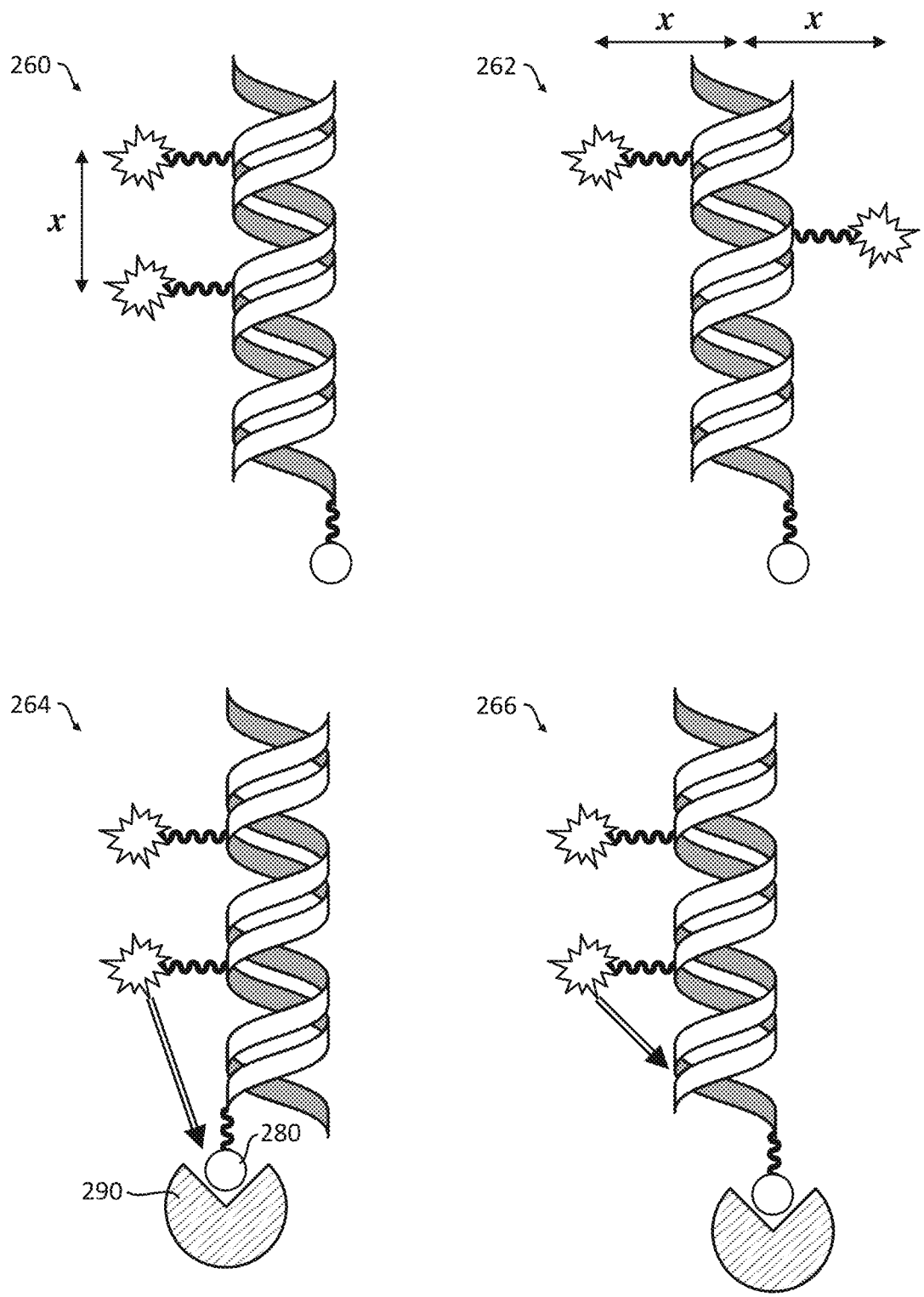

FIG. 2C depicts generic nucleic acids having different relative label attachment sites (top) and different reactant connectivity (bottom).

Figure 3A:
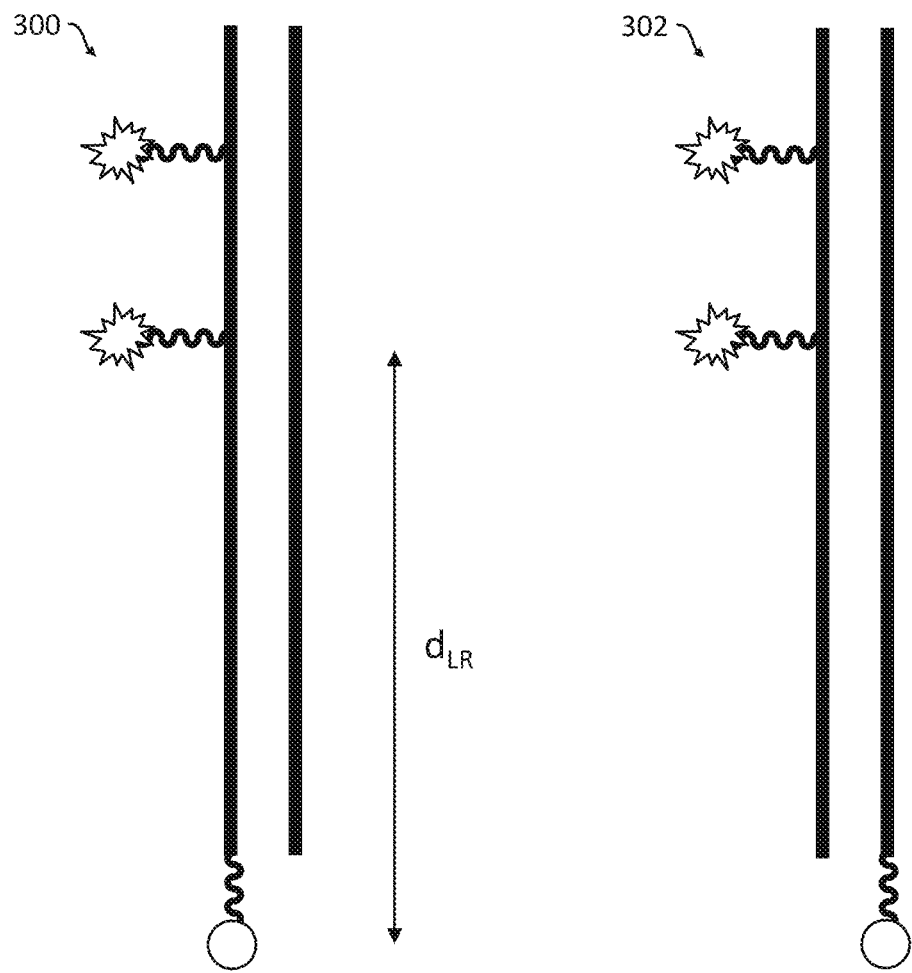

FIG. 3A depicts generic nucleic acids connecting labels to a reactant via same (left) or opposite (right) oligonucleotide strand connectivity.

Figure 3B:
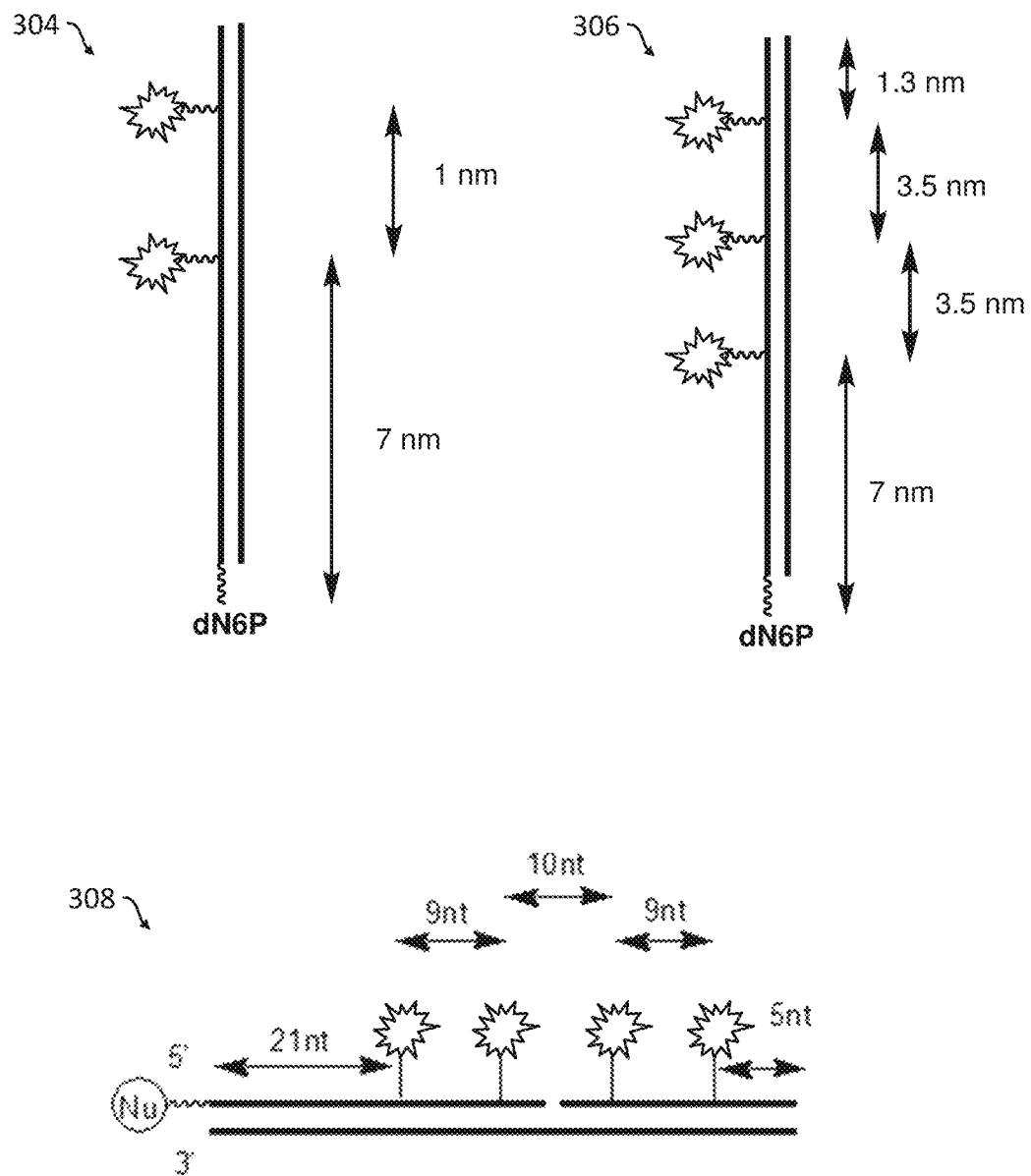

FIG. 3B depicts generic nucleic acids with examples of approximate size constraints that may be used in the design of brightly labeled reactants.

Figure 3C:
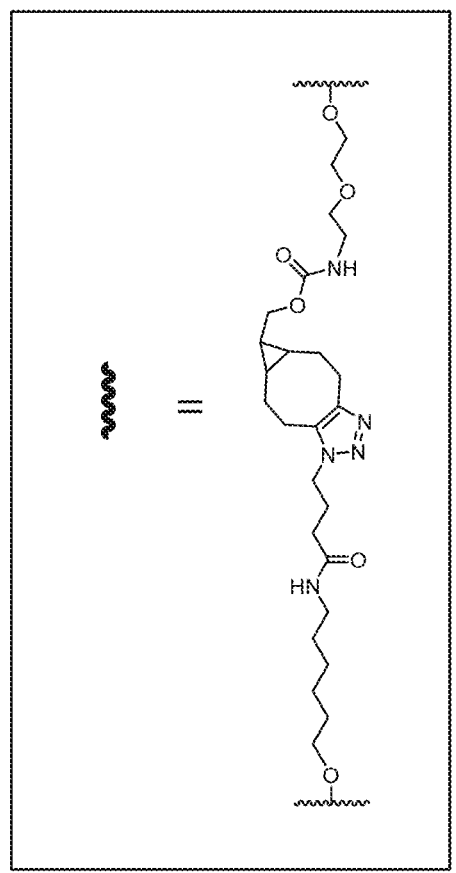
Figure 3C:
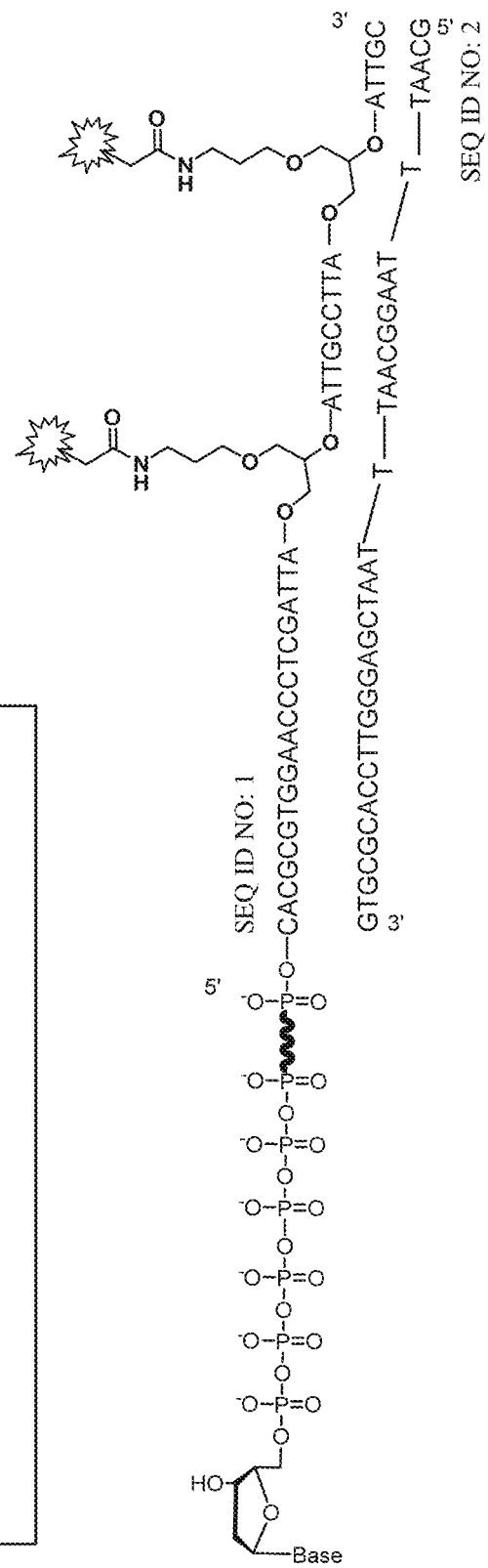

FIG. 3C is an example structure of a nucleic acid connecting two luminescent labels to a nucleoside polyphosphate via same-strand connectivity.

Figure 3D:
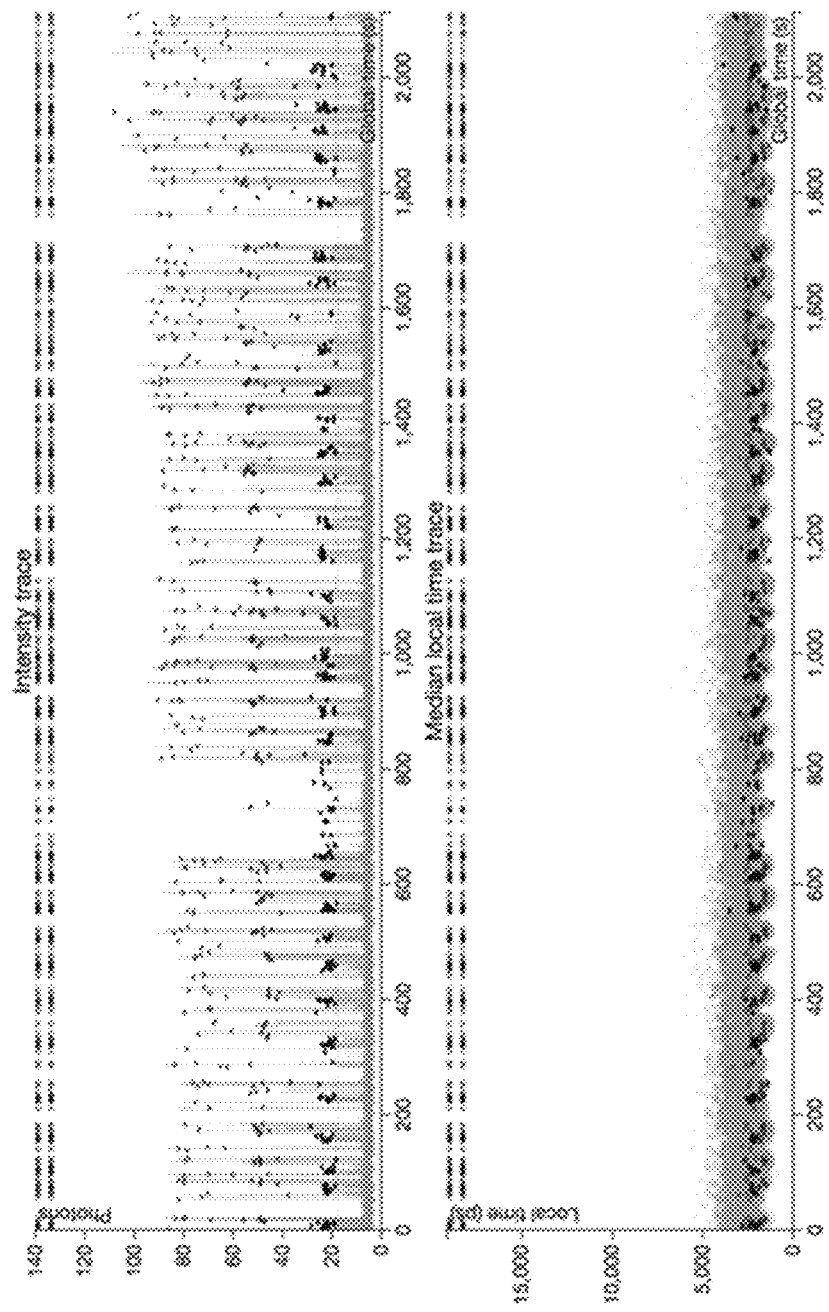
Figure 3D:
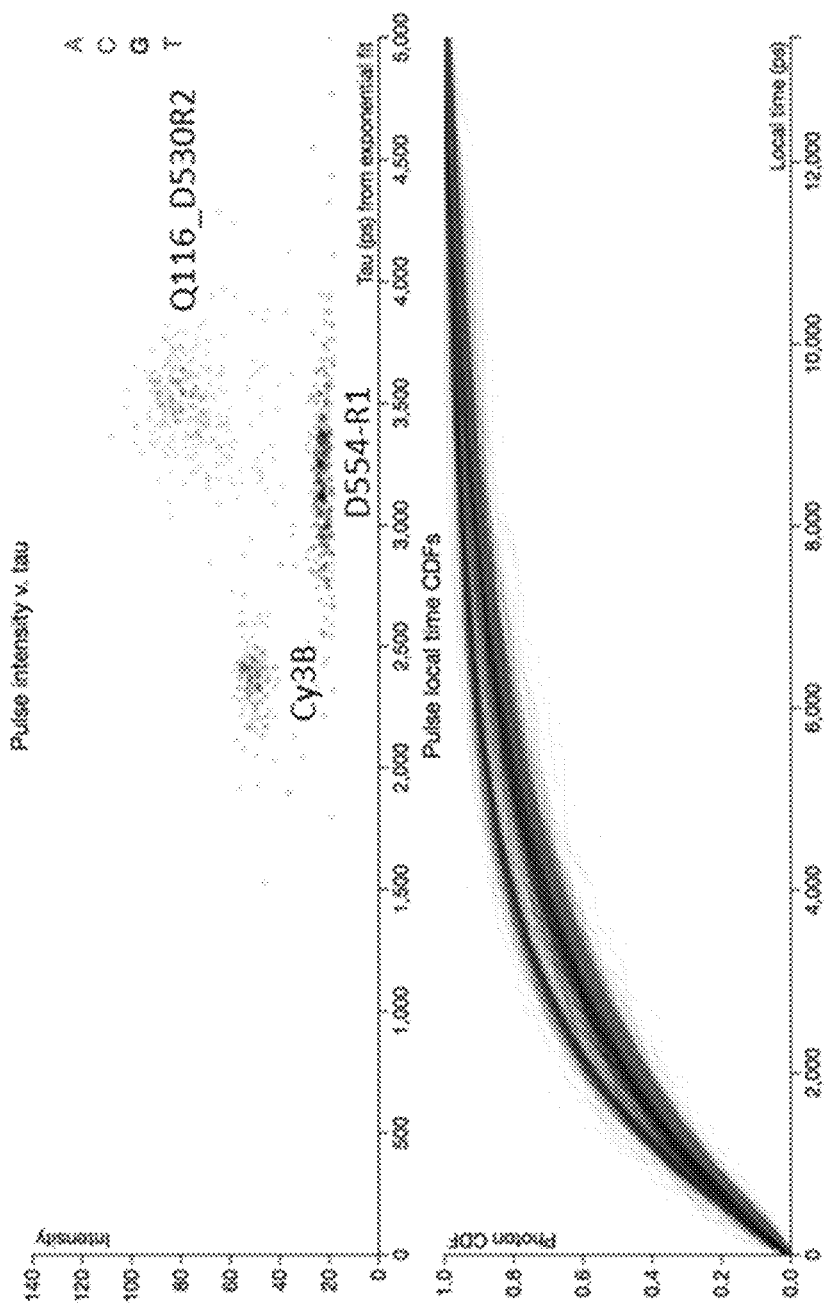

FIG. 3D depicts an example of a sequencing reaction which confirmed that a rod-shaped nucleic acid linker (e.g., as shown in FIG. 3C) can be used to detect incorporation of a labeled nucleoside polyphosphate.

Figure 3E:
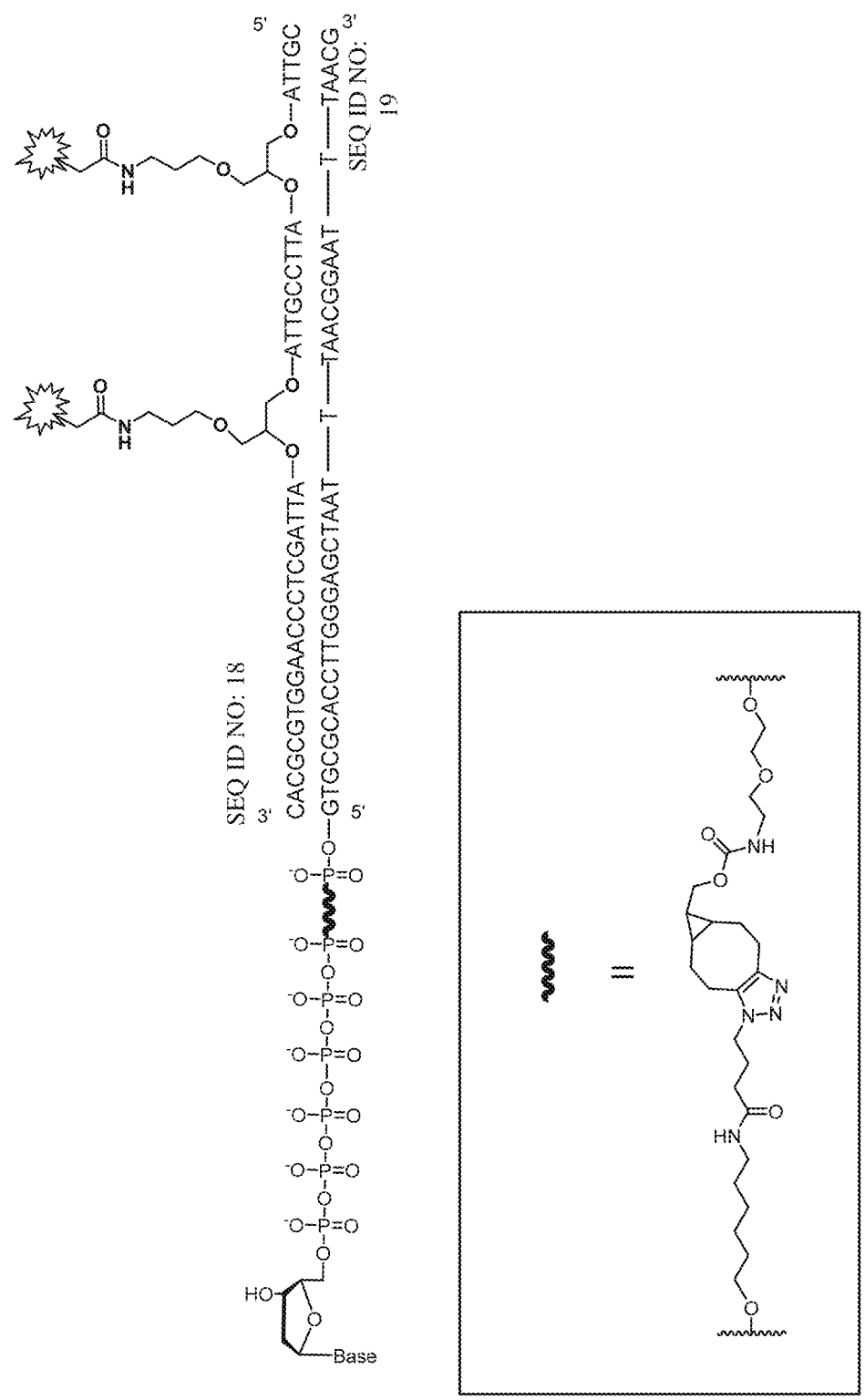

FIG. 3E is an example structure of a nucleic acid connecting two luminescent labels to a nucleoside polyphosphate via opposite-strand connectivity.

Figure 3F:
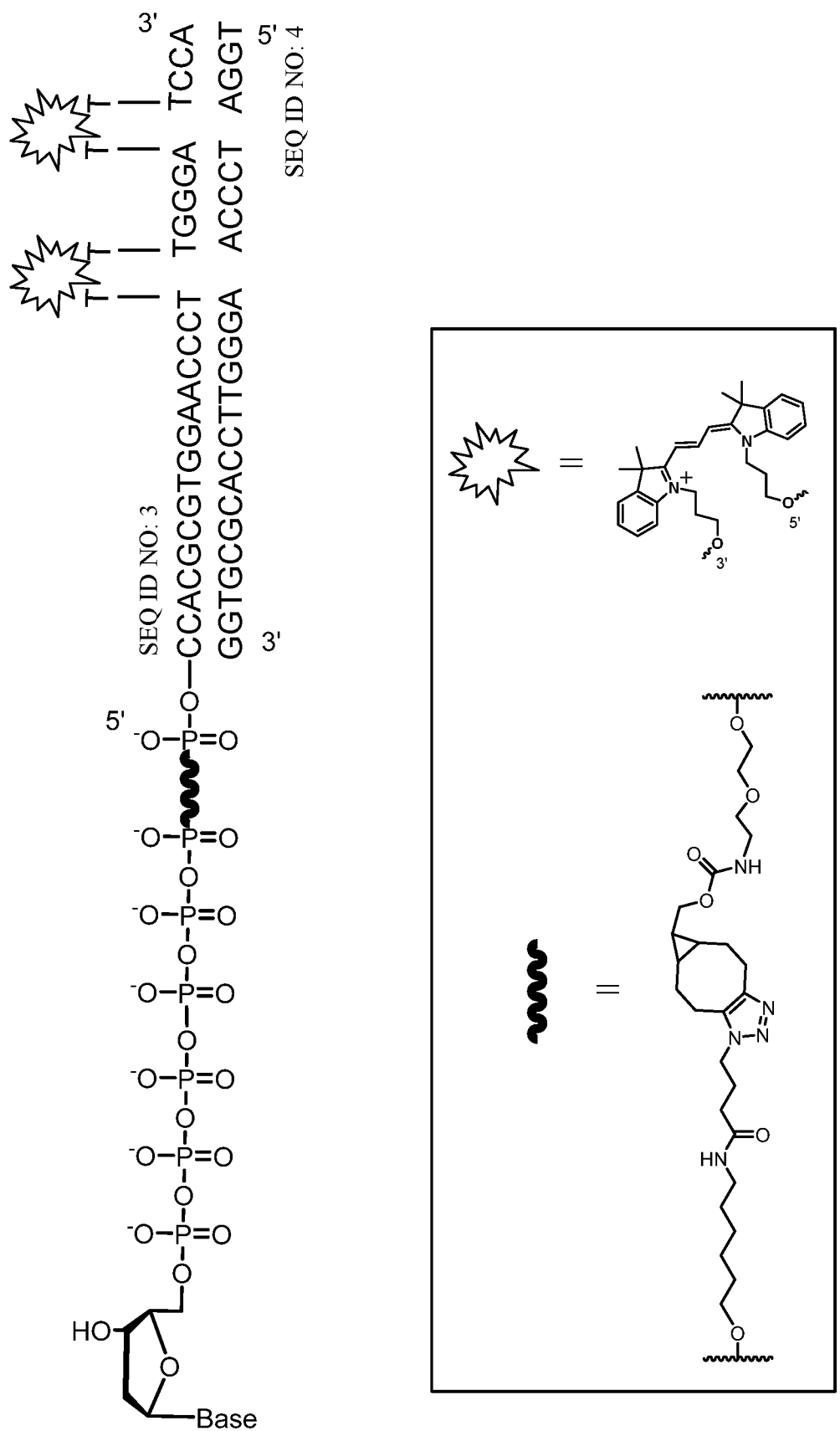

FIG. 3F is an example structure of a nucleic acid linker having luminescent labels integrated into an oligonucleotide strand.

Figure 3G:
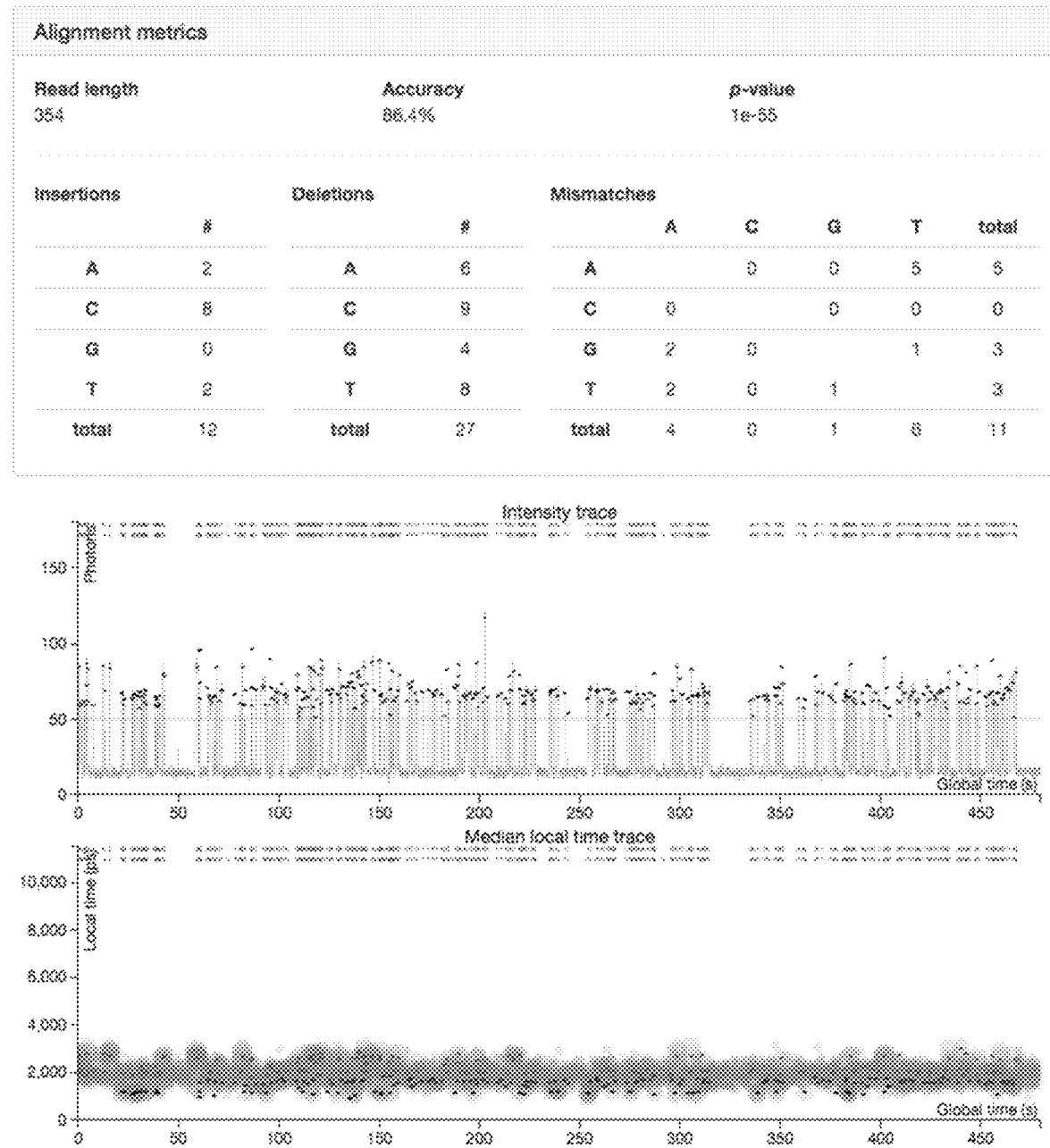
Figure 3G:
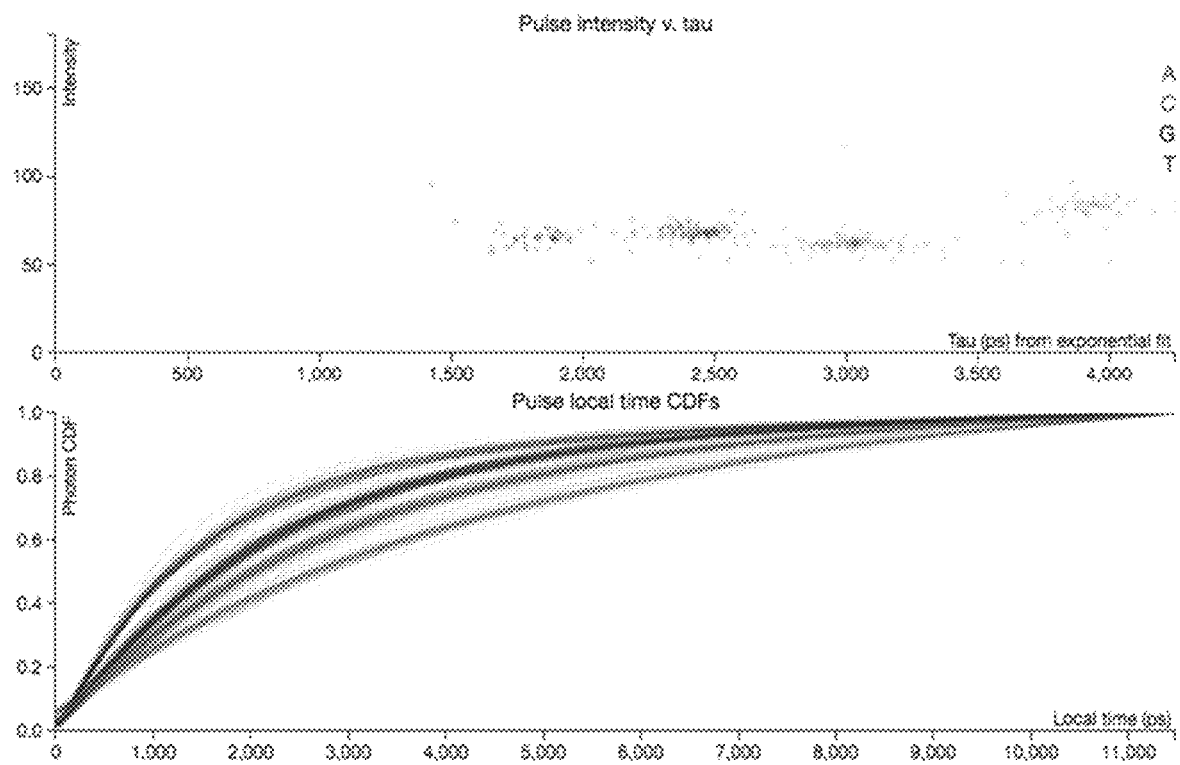
Figure 3G:
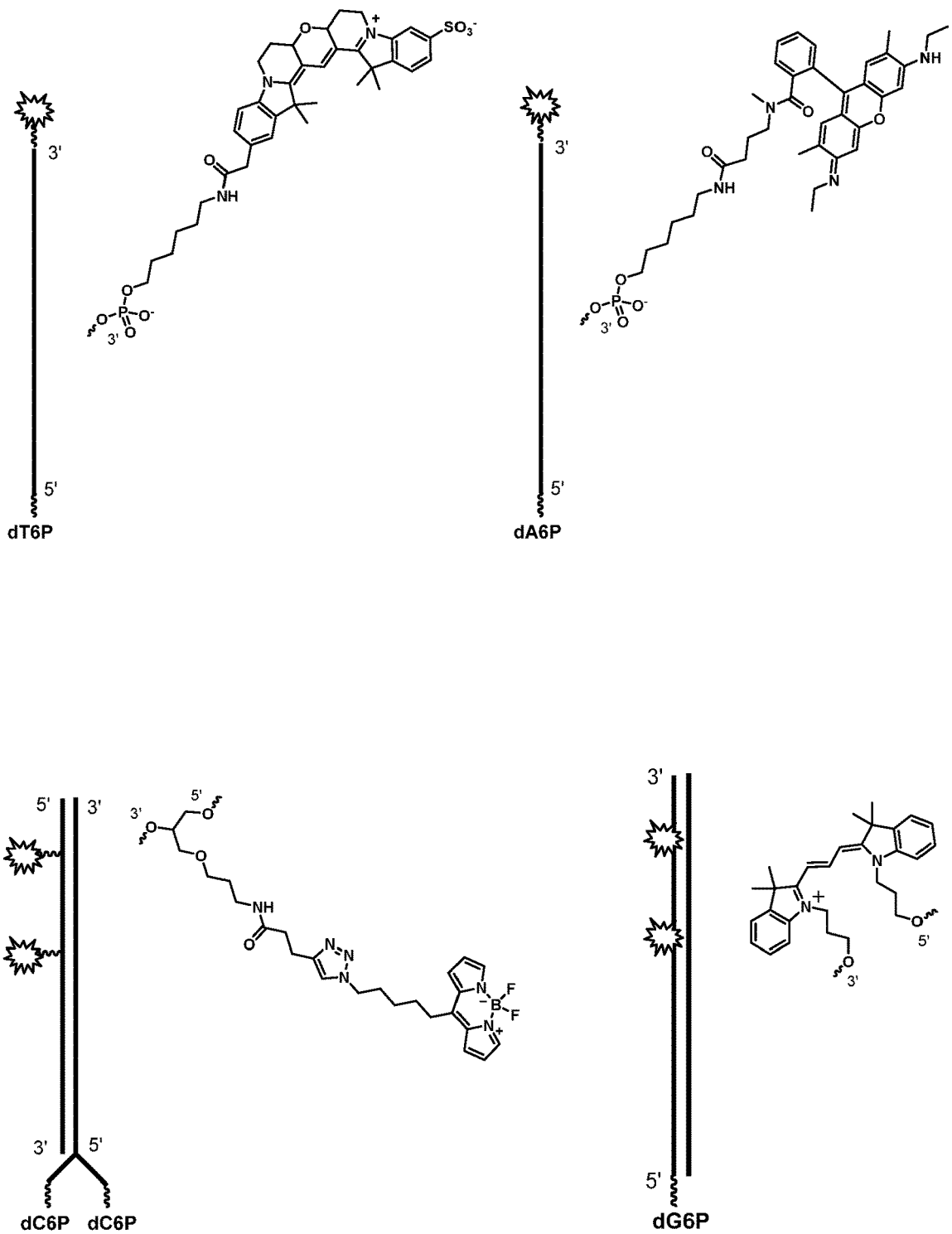

FIG. 3G depicts an example of a sequencing reaction that was conducted using the four different nucleic acid linker constructs shown.

Figure 4A:
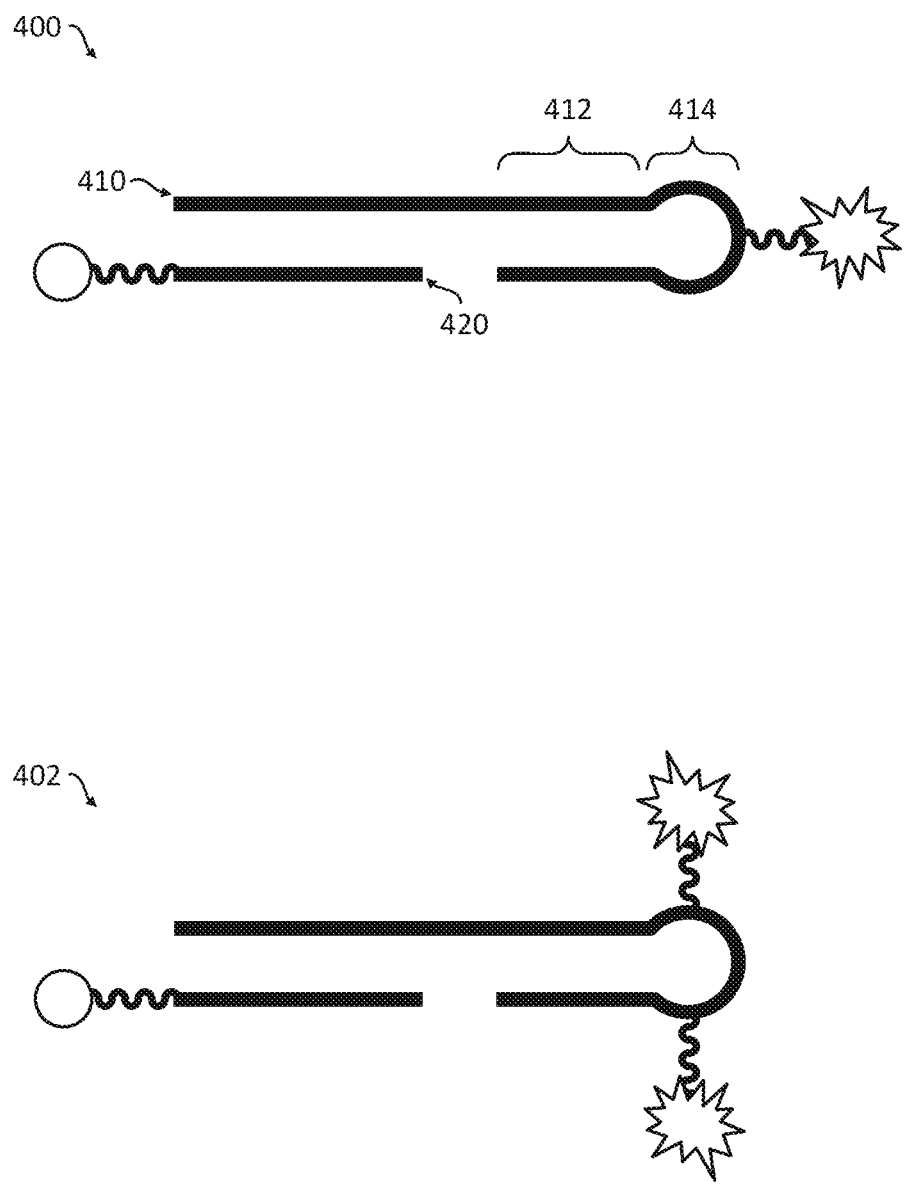

FIG. 4A depicts generic nucleic acid linkers having a single stem-loop secondary structure.

Figure 4B:
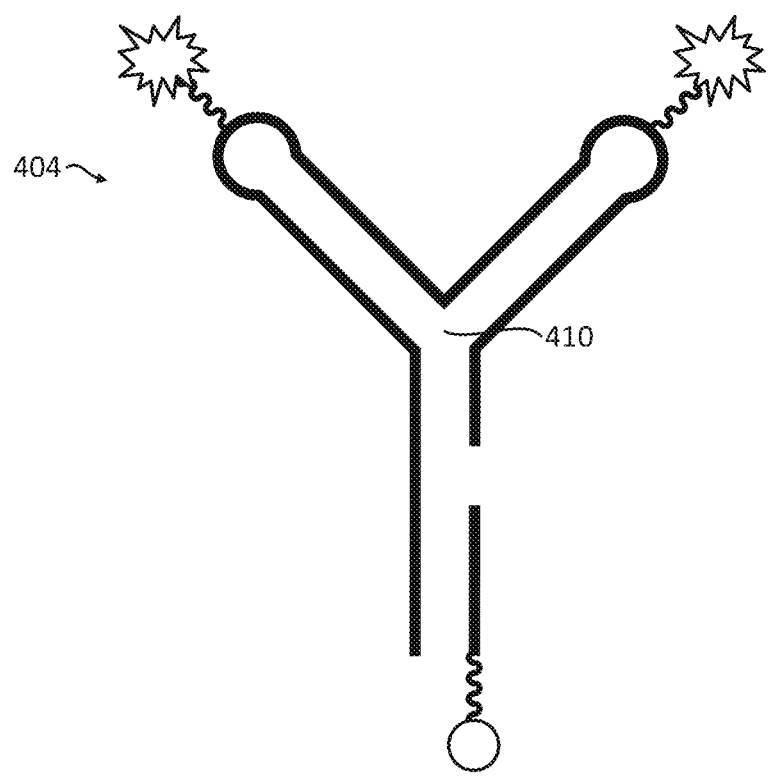
Figure 4B:
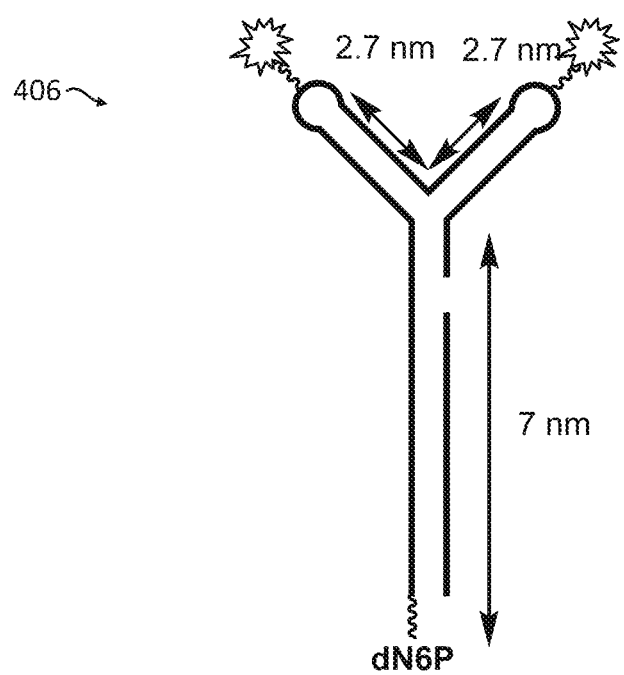

FIG. 4B depicts generic nucleic acid linkers having multiple stem-loop secondary structures.

Figure 4C:
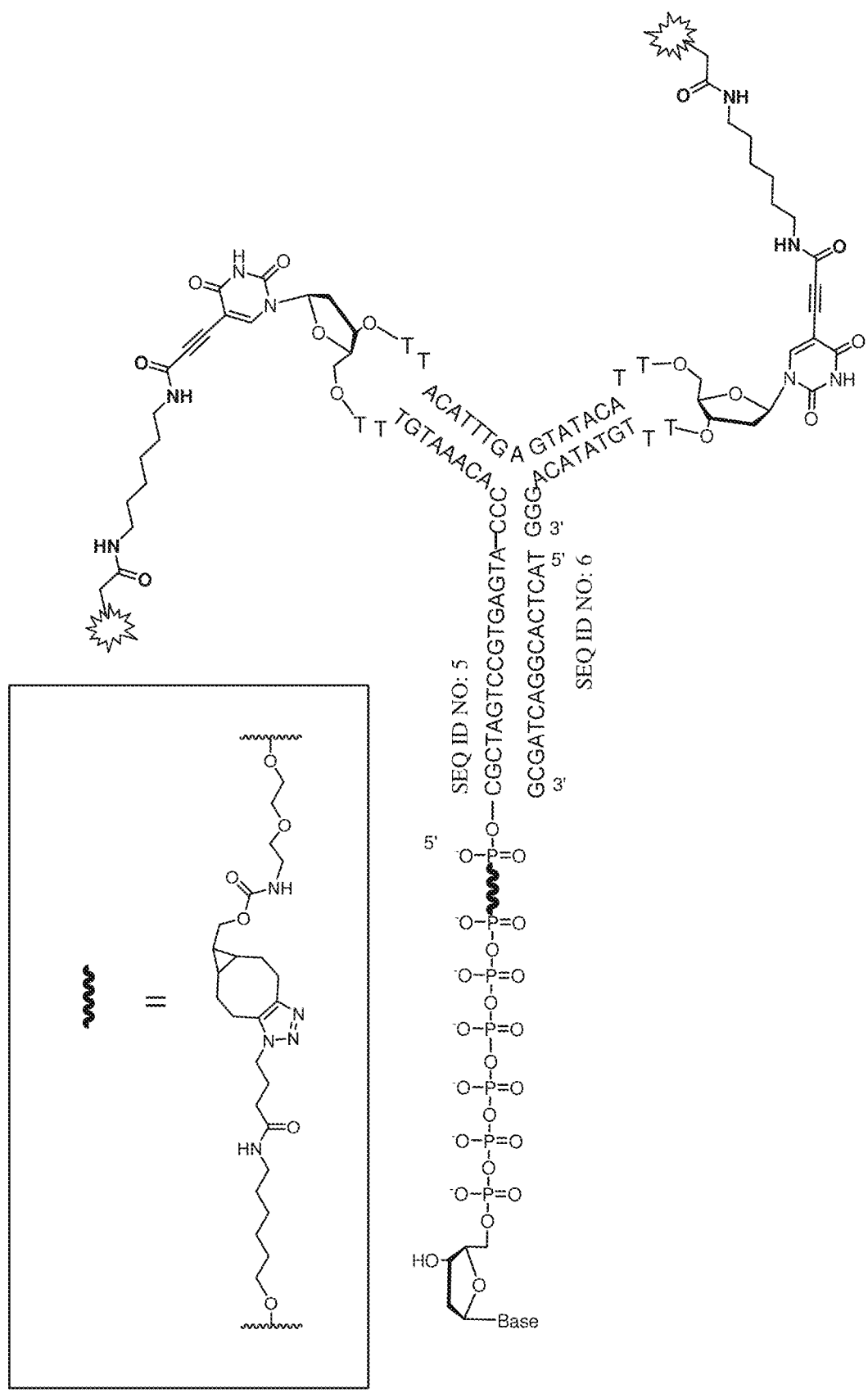

FIG. 4C is an example structure of a nucleic acid linker having luminescent labels attached at loops of separate stem-loop secondary structures.

Figure 4D:
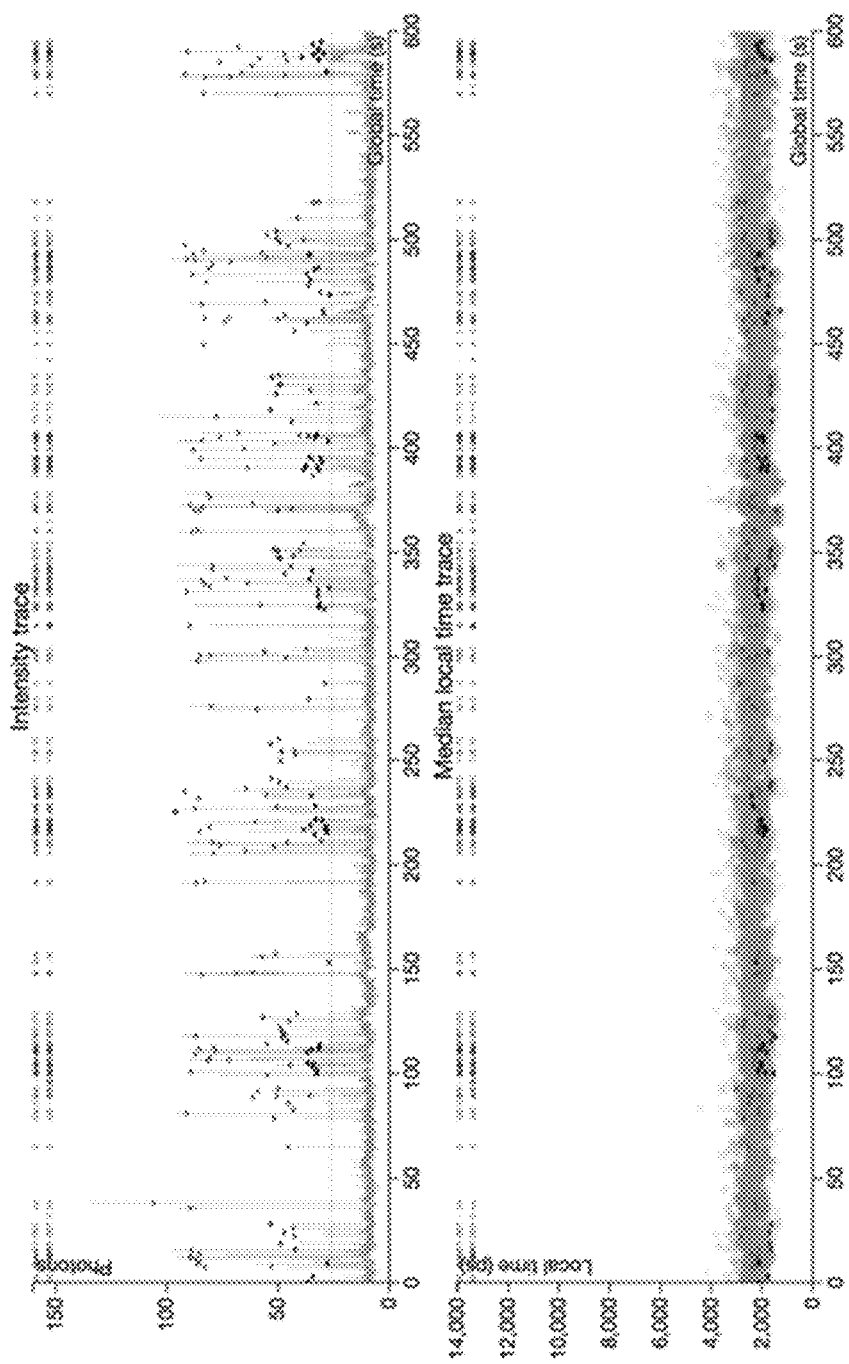
Figure 4D:
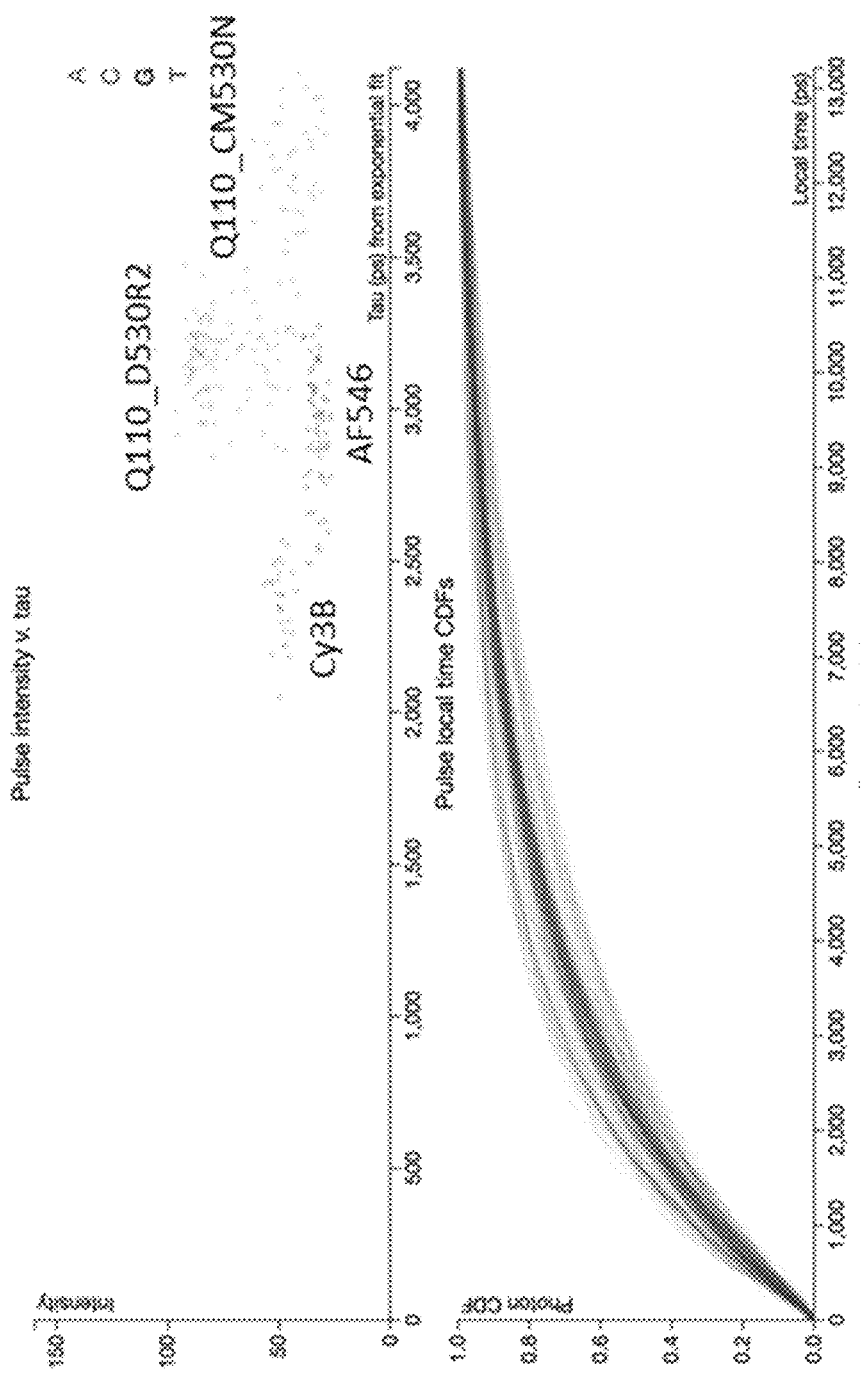

FIG. 4D depicts an example of a sequencing reaction which confirmed that a labeled nucleoside polyphosphate having a stem-loop nucleic acid linker (e.g., as shown in FIG. 4C) can be used to detect incorporation of a nucleoside polyphosphate.

Figure 5A:
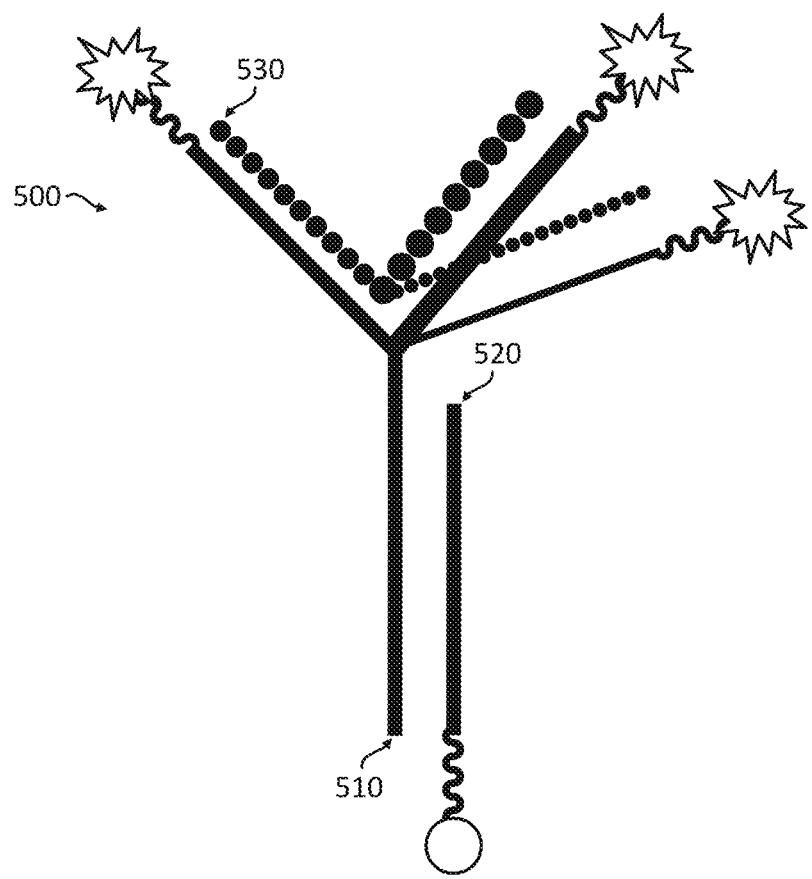
Figure 5A:
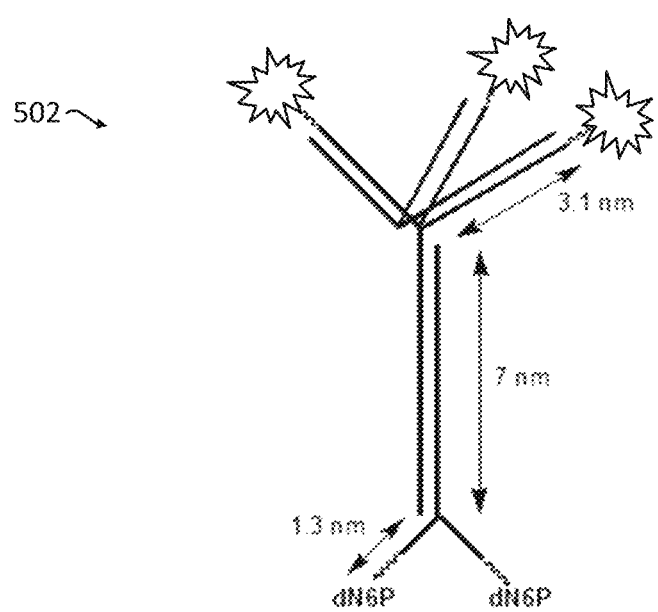

FIG. 5A generically depicts tree-shaped nucleic acid linkers having branching oligonucleotide strands attached to luminescent labels.

Figure 5B:
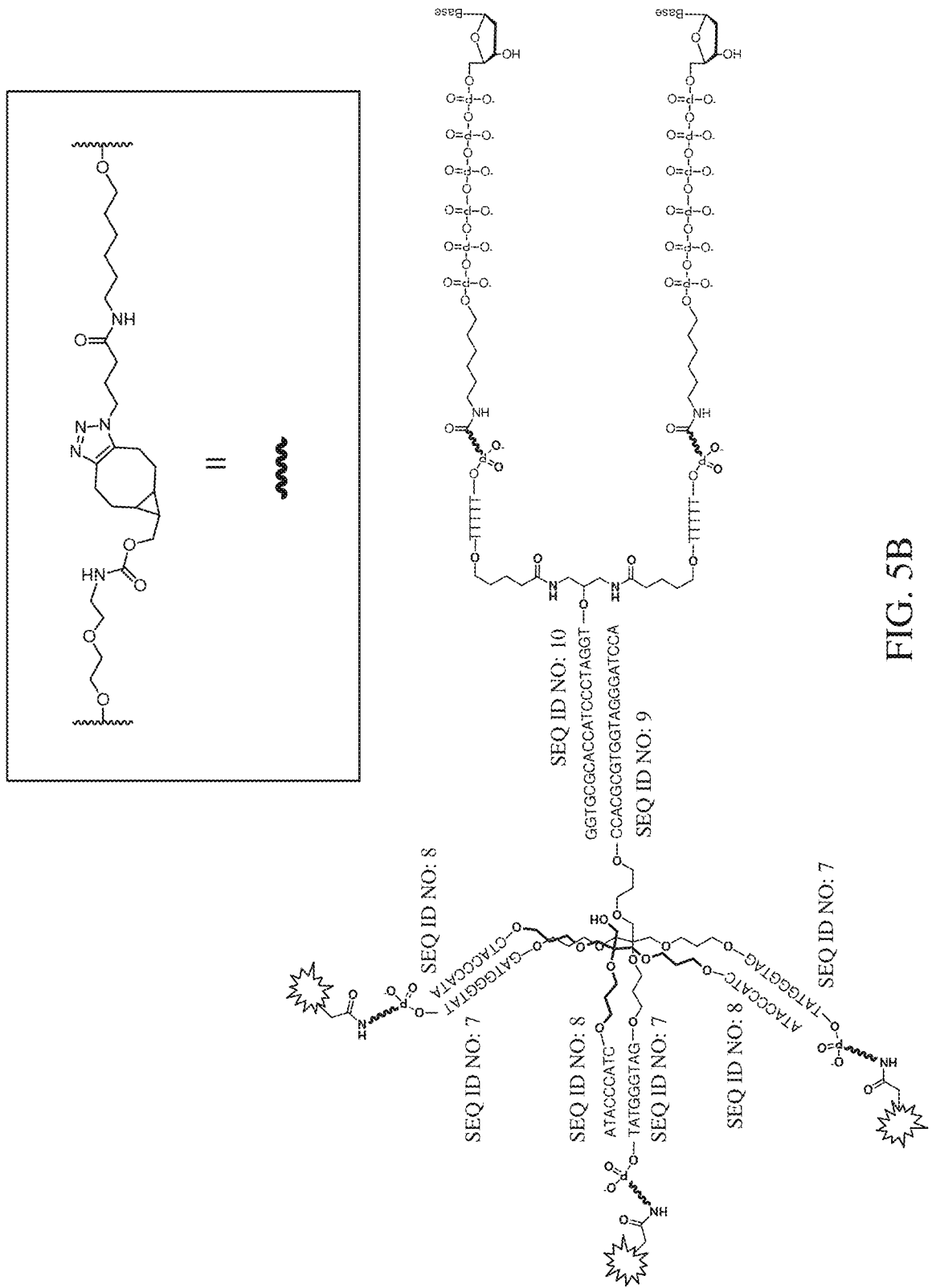

FIG. 5B is an example of a tree-shaped nucleic acid linker having luminescent labels attached at terminal ends of separate branching oligonucleotide strands.

Figure 6A:
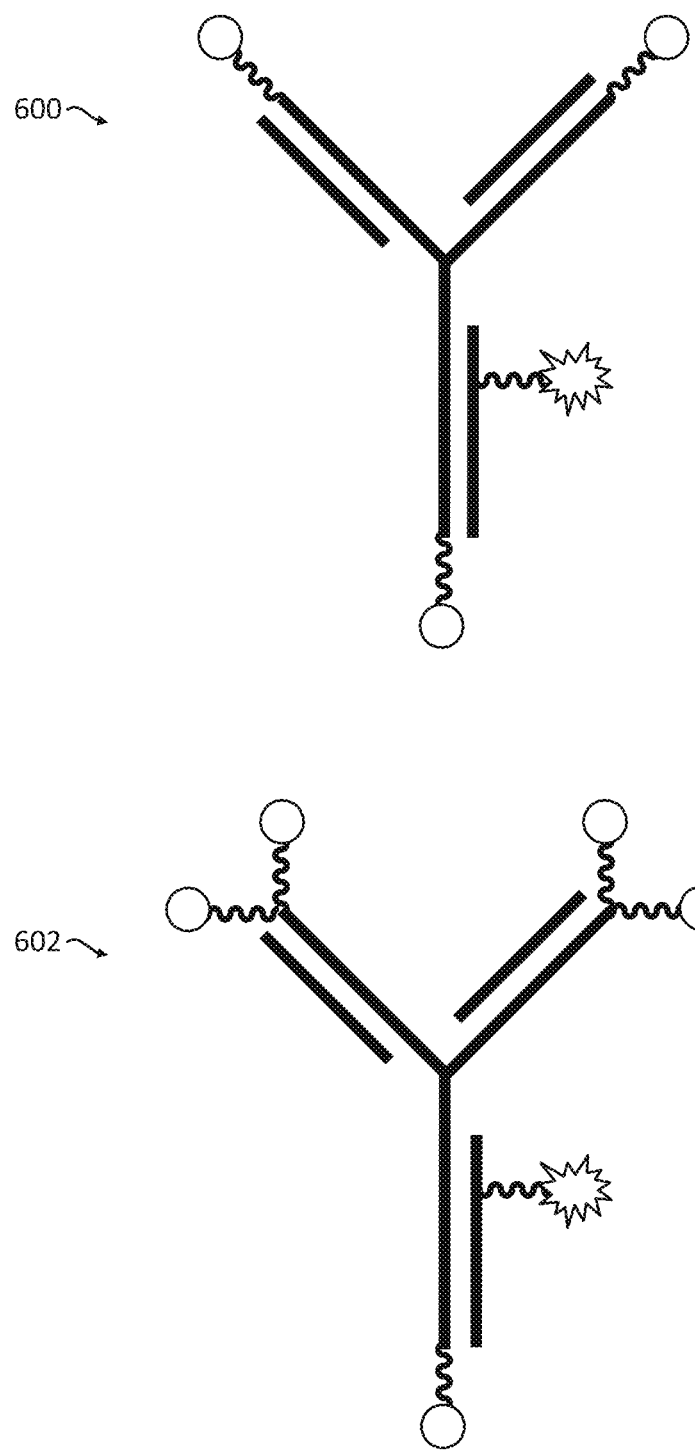
Figure 6A:
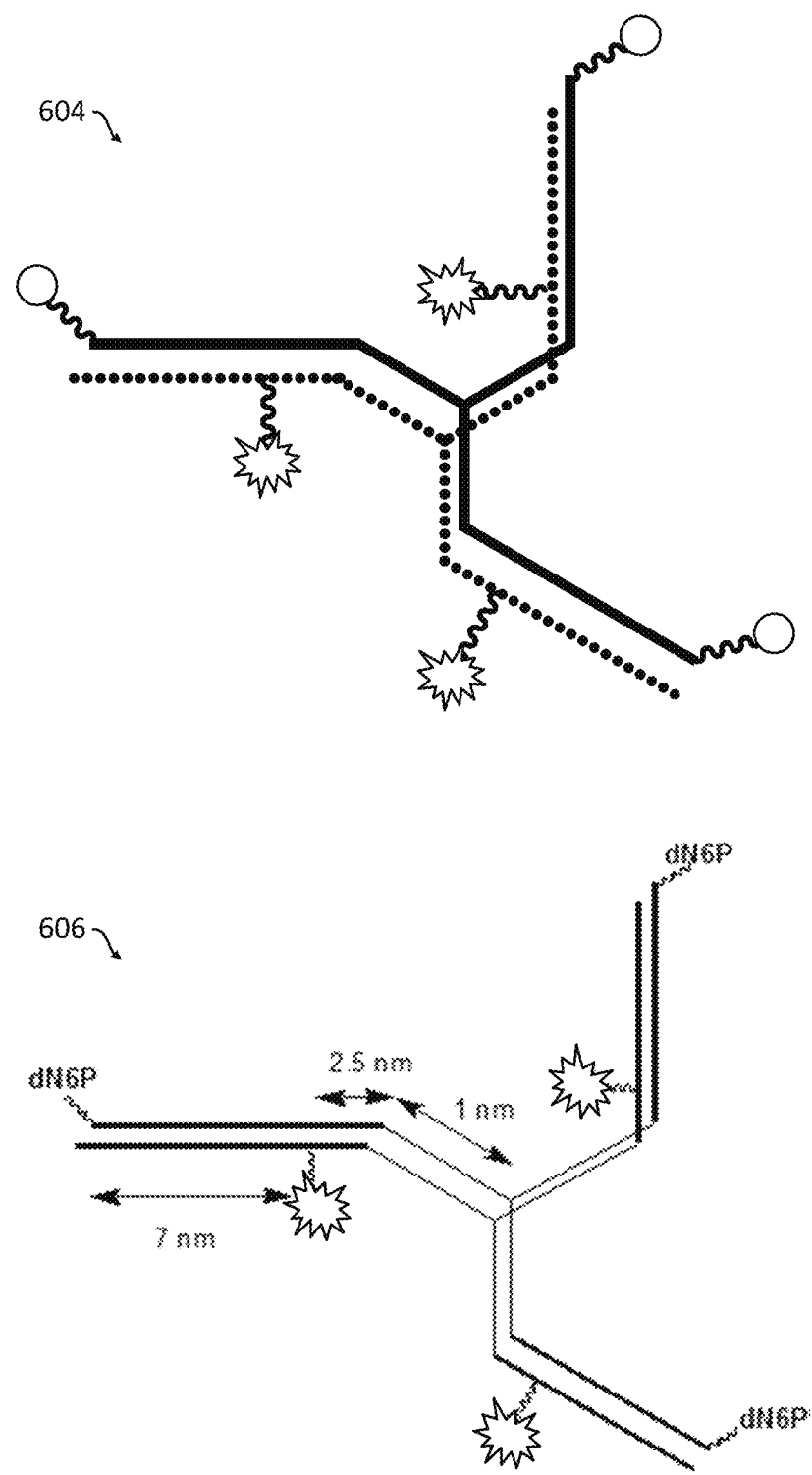

FIG. 6A generically depicts star-shaped nucleic acid linkers and provides an example of approximate size constraints that can be used in the design of star-shaped nucleic acid linkers.

Figure 6B:
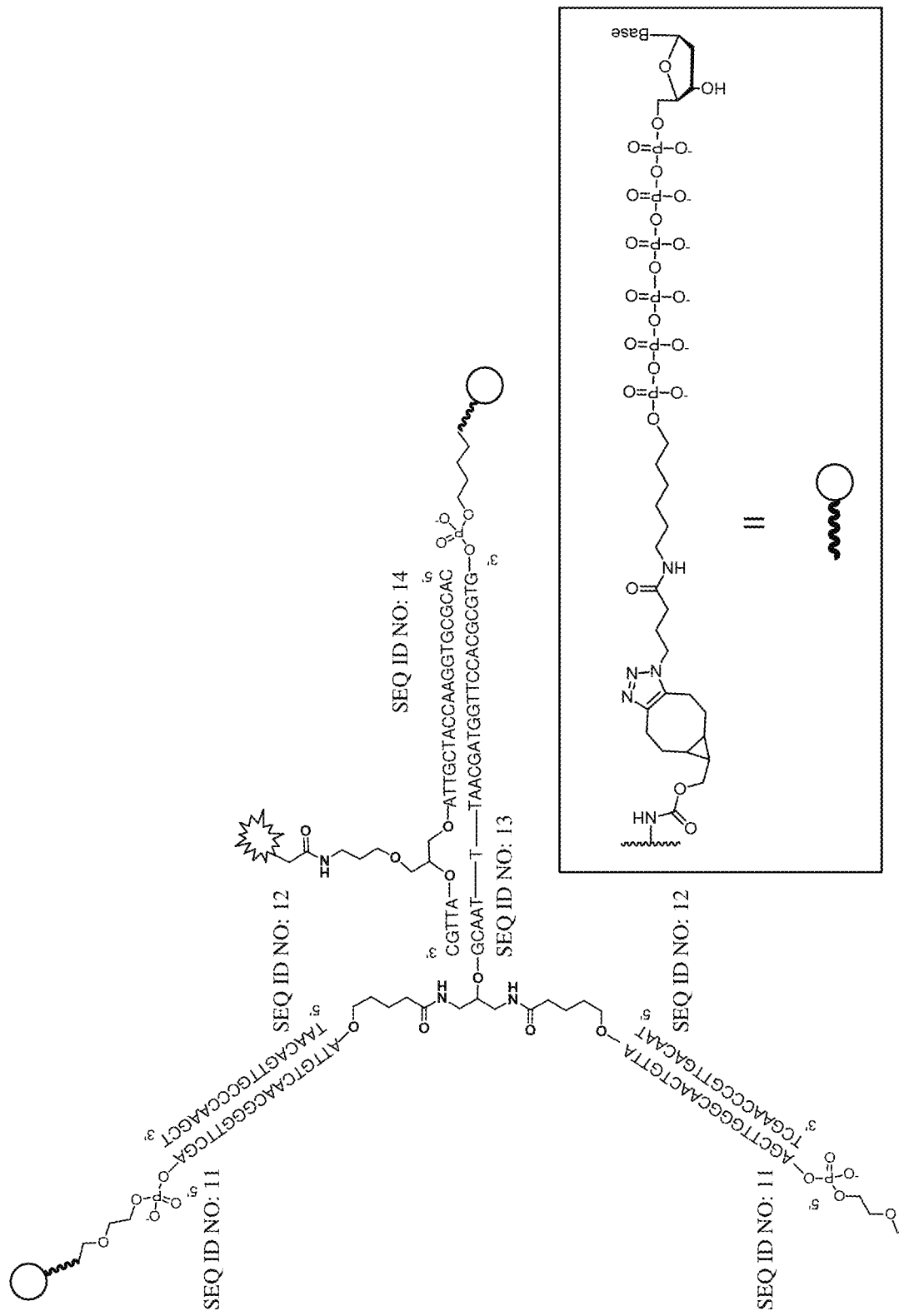

FIG. 6B is an example structure of a star-shaped nucleic acid linker.

Figure 6C:
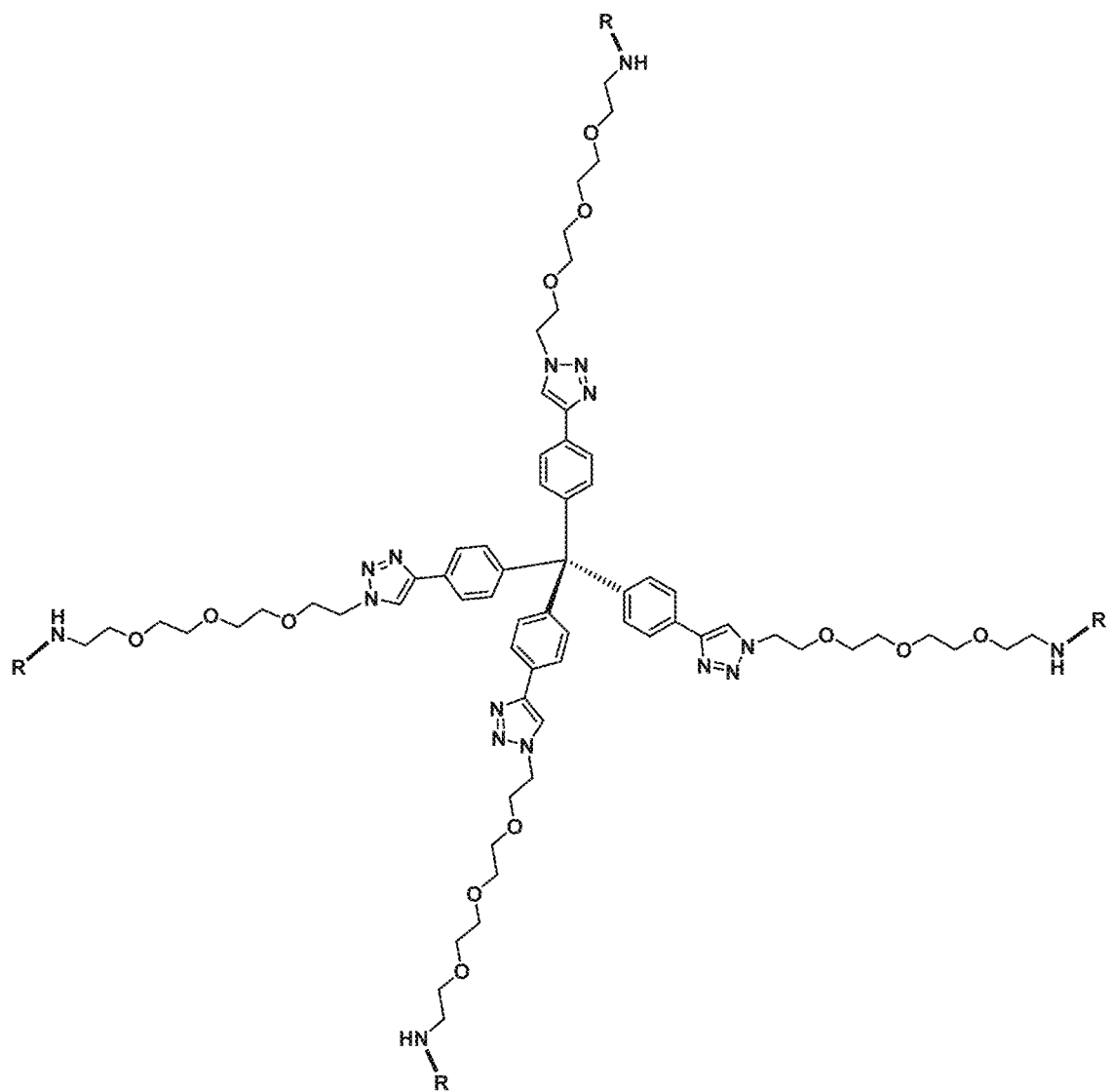
Figure 6C:
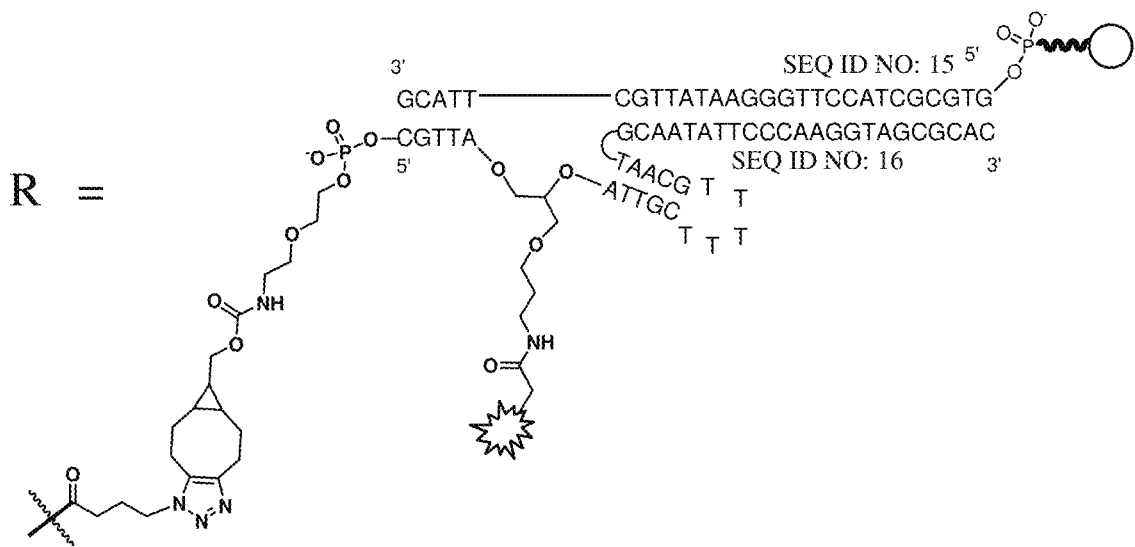
Figure 6C:
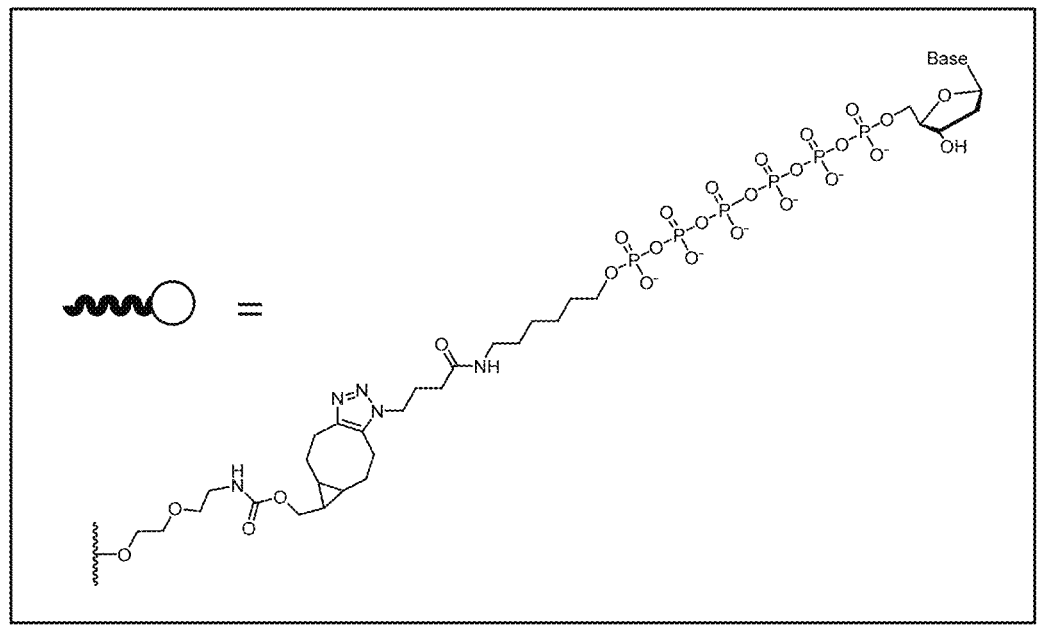

FIG. 6C is an example structure of a nucleic acid linker having a tetrahedral core.

Figure 6D:
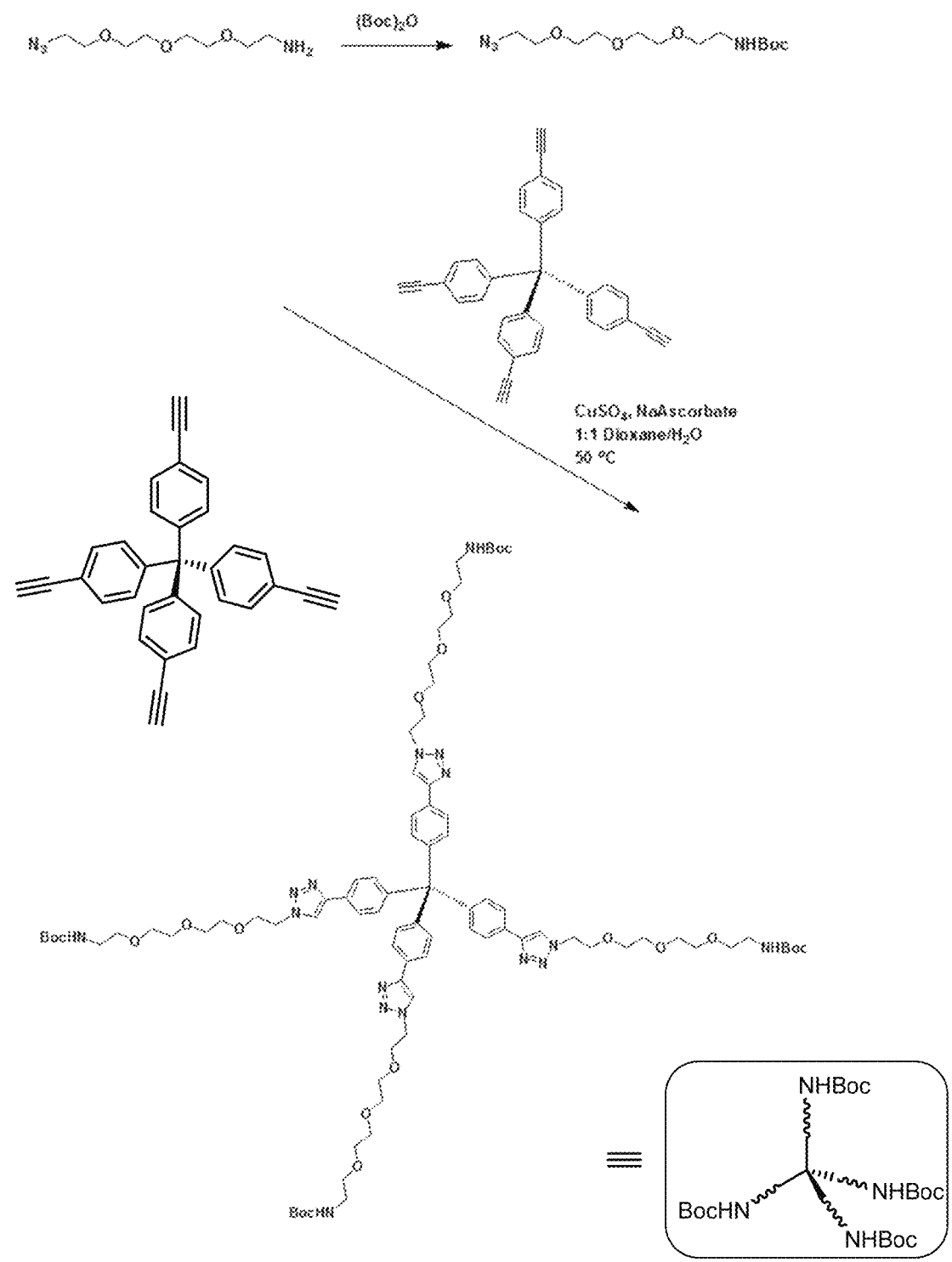
Figure 6D:
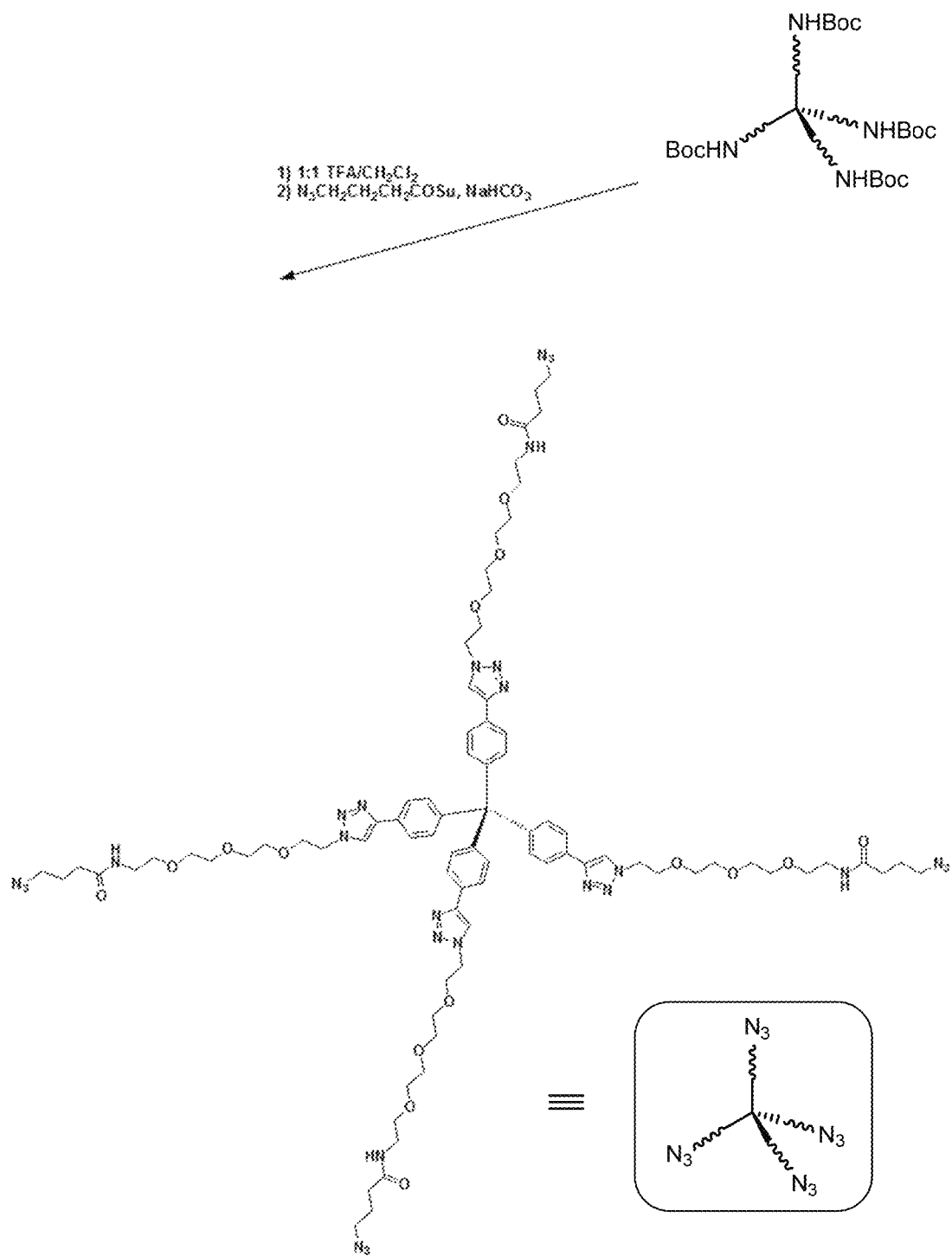

FIG. 6D depicts an example of a reaction scheme that can be used to synthesize a nucleic acid linker having a tetrahedral core.

Figure 6E:
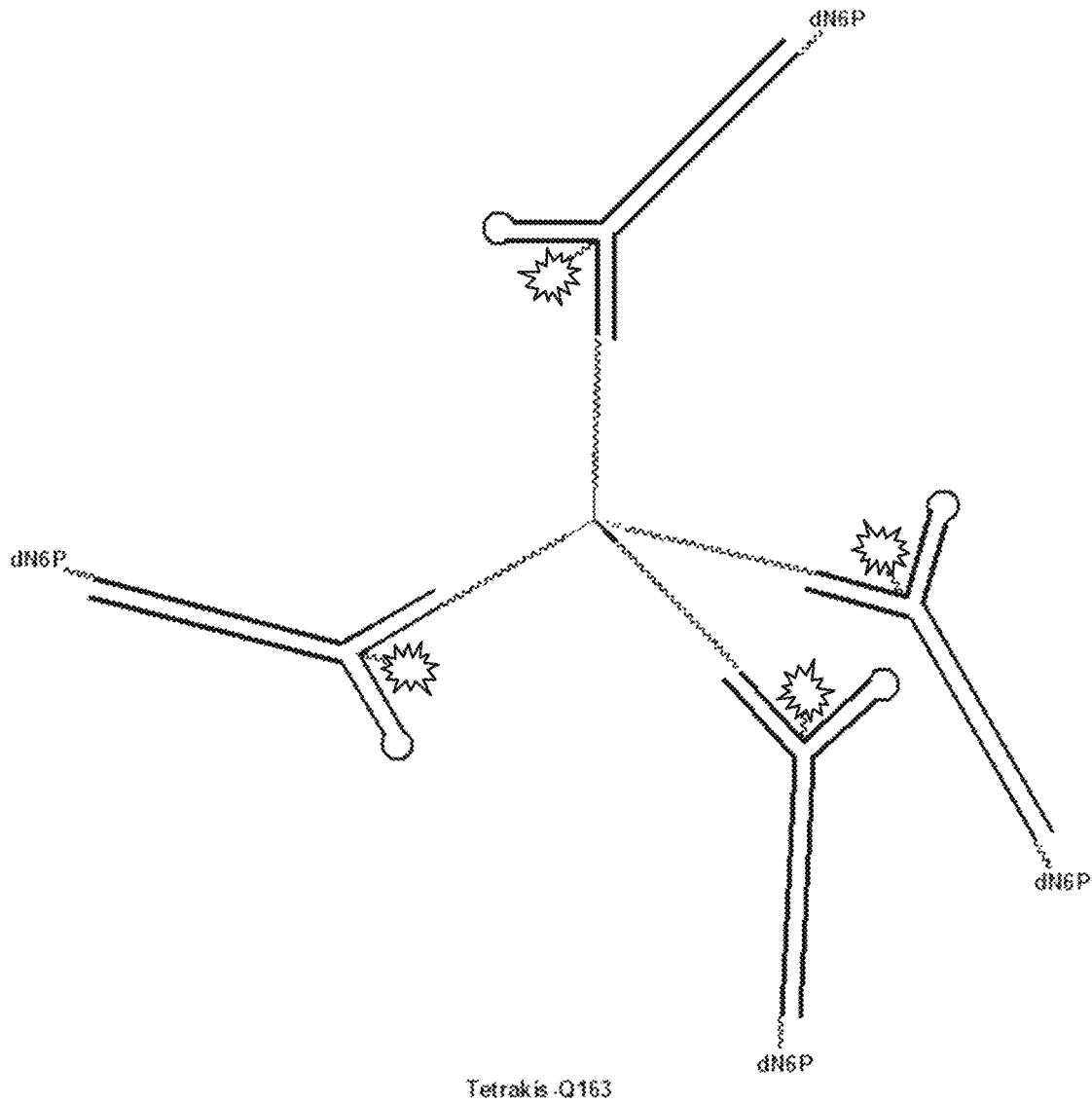

FIG. 6E generically depicts a tetrahedral-based nucleic acid linker structure having luminescent labels attached at three-way junctions.

Figure 7:
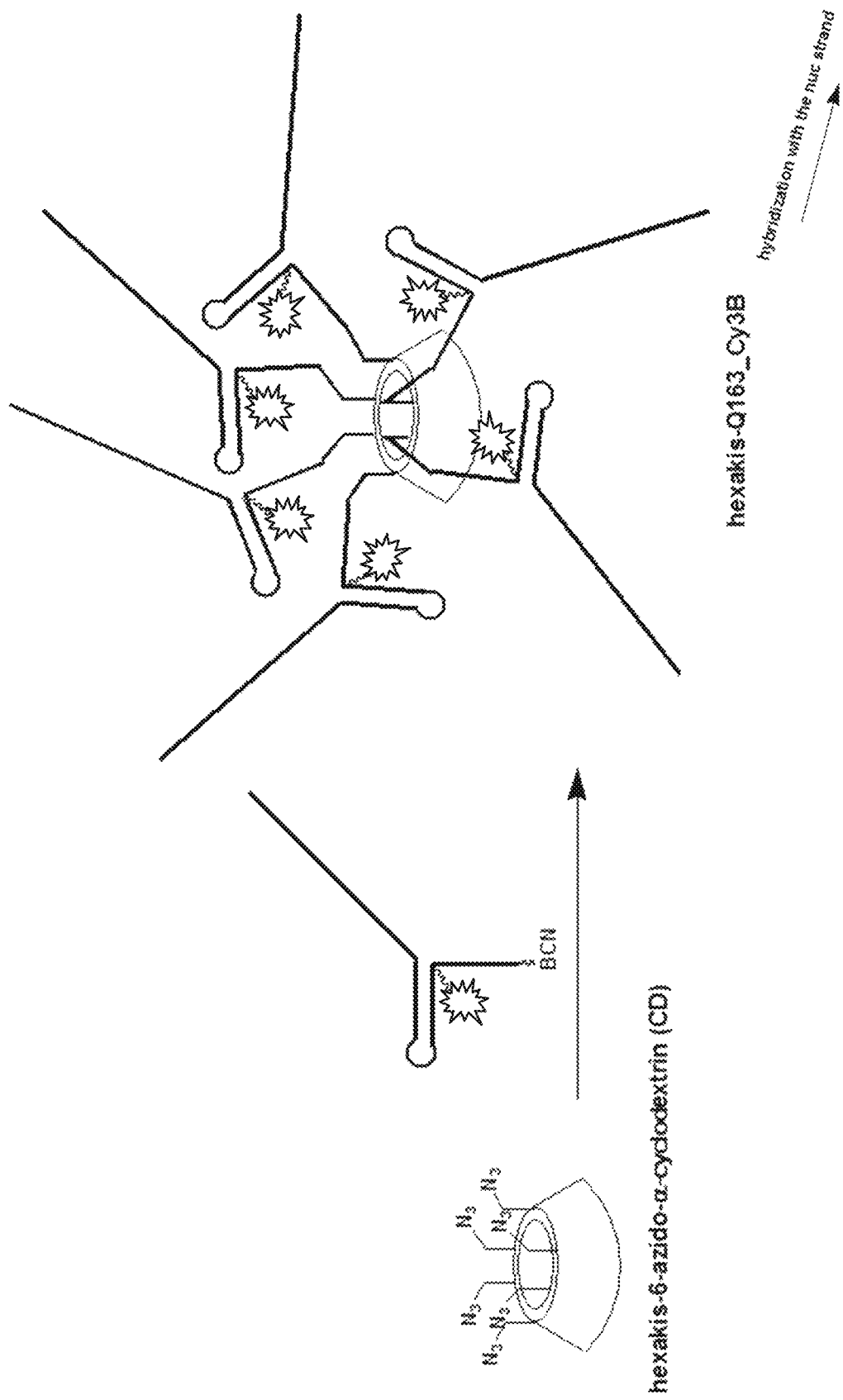

FIG. 7 generically depicts a process of generating a cyclodextrin-based nucleic acid linker having luminescent labels attached at three-way junctions.

Figure 8:
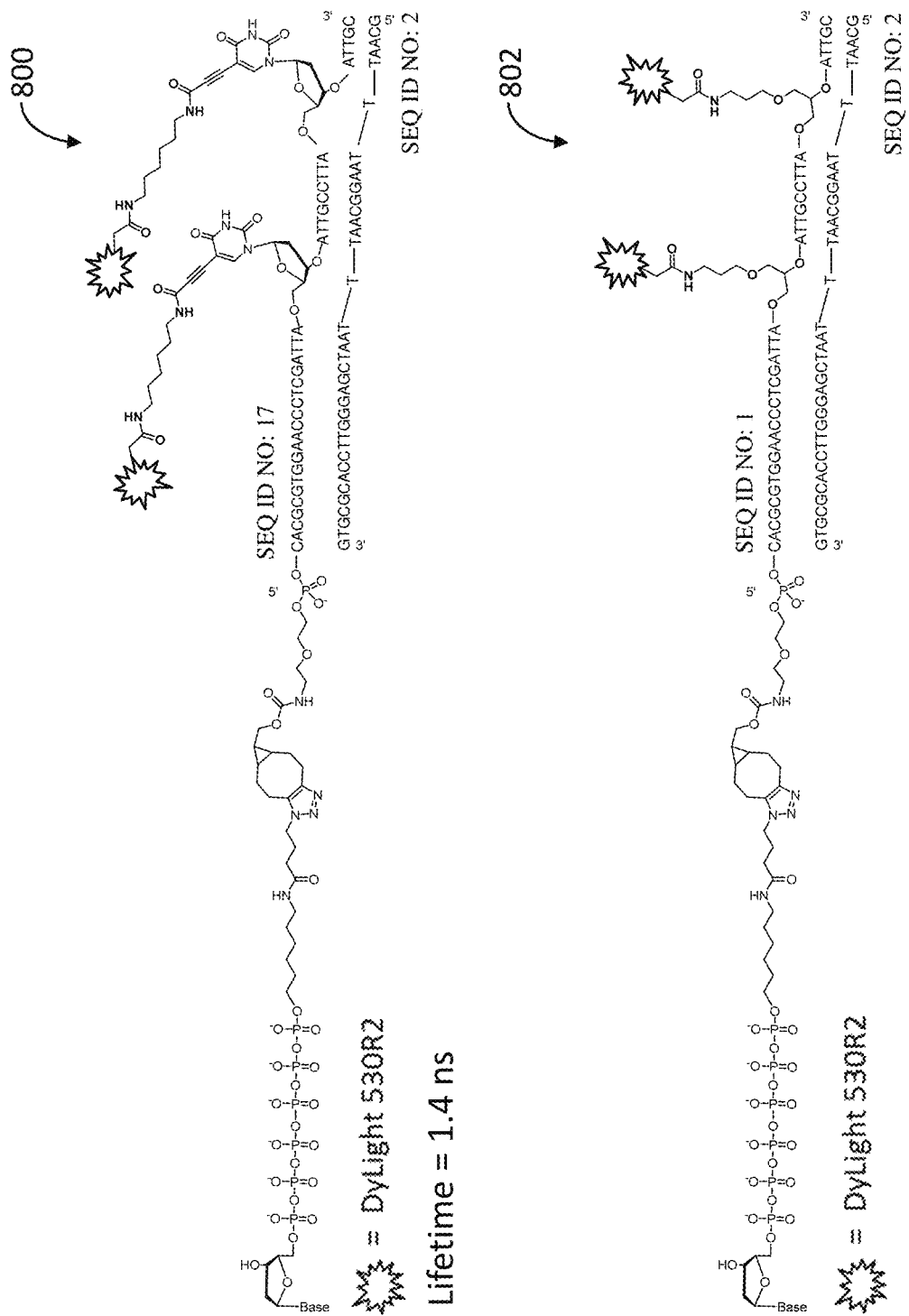

FIG. 8 depicts examples of nucleic acid linker structures used in a set of experiments to evaluate the effects of spacer length on fluorescence lifetime measurements.

Figure 9:
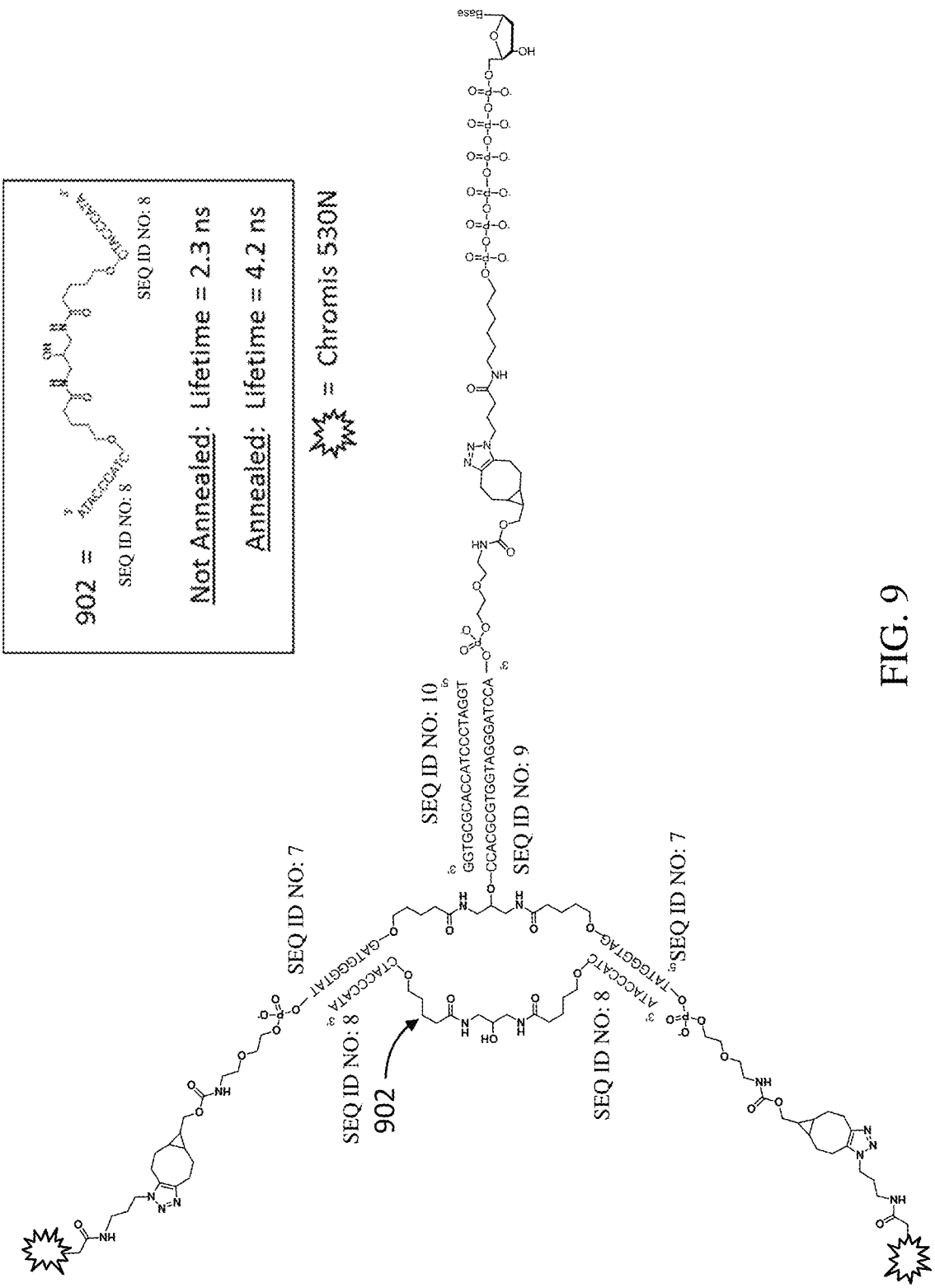

FIG. 9 depicts examples of nucleic acid linker structures used in a set of experiments to evaluate the effects of linker constraint on fluorescence lifetime measurements.

Figure 10:
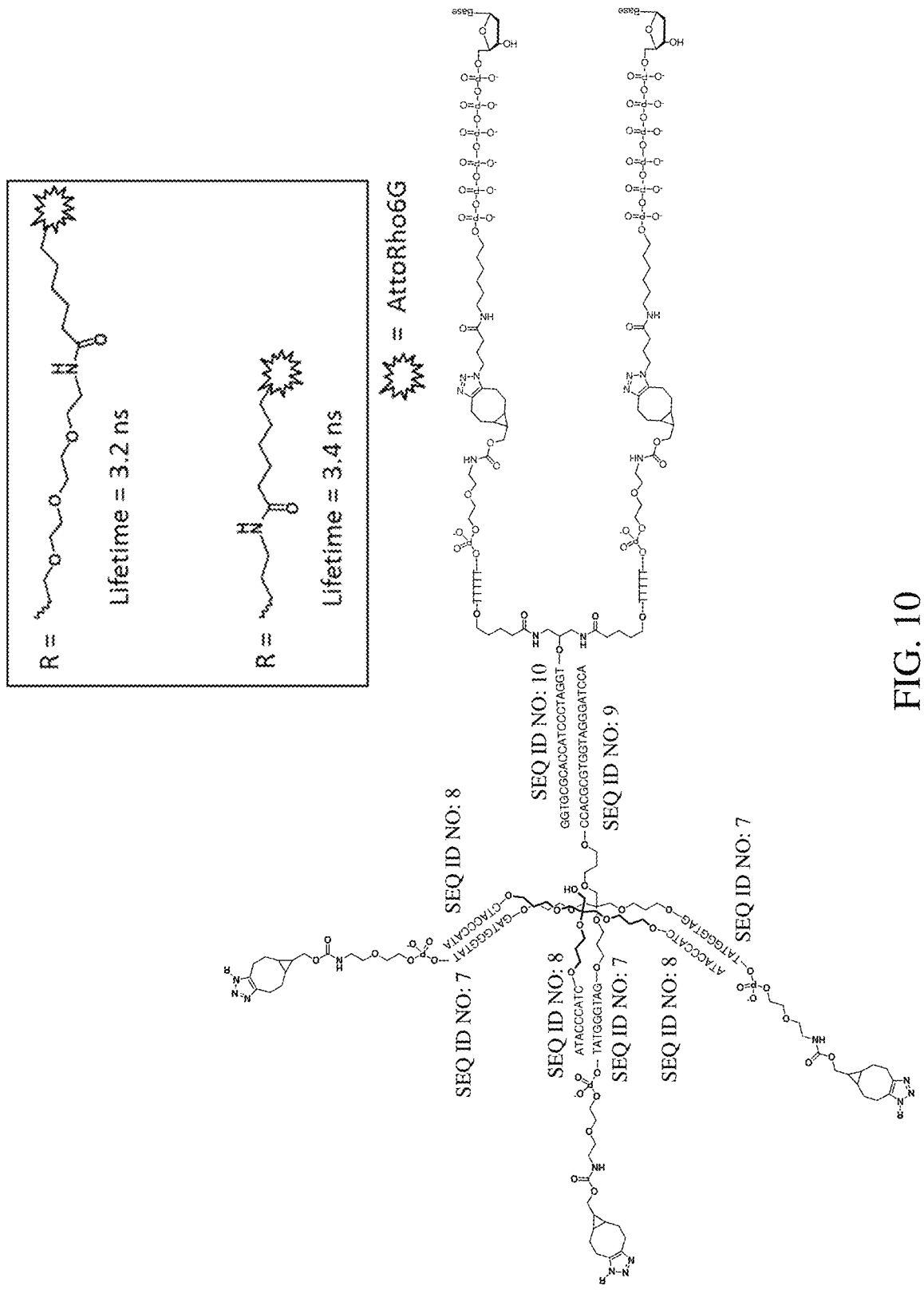

FIG. 10 depicts examples of nucleic acid linker structures used in a set of experiments to evaluate the effects of spacer length on fluorescence lifetime in constrained linkers.

DETAILED DESCRIPTION

Among other aspects, the disclosure provides luminescently labeled reactants comprising two or more labels, wherein the labels are configured to provide high intensity and/or consistent emission characteristics (e.g., consistent emission lifetimes). In some embodiments, the two or more labels are configured to avoid label-label interactions that could reduce the intensity or other emission characteristics of the emissions. In some embodiments, the two or more labels are configured to a) avoid interactions with a linker, and/or b) to each have similar interactions with a linker.

In some aspects, the disclosure provides methods and compositions related to luminescently labeled reactants having high emission intensity. In some aspects, the disclosure provides methods and compositions related to luminescently labeled reactants having high emission brightness. In some aspects, the disclosure relates to brightly labeled reactants having consistent emission lifetime. As used herein, in some embodiments, "brightness" (and variations thereof, e.g., "bright," "brightly," etc.) refers to a parameter that reports on the average emission intensity per labeled reactant molecule. Thus, in some embodiments, "emission intensity" may be used to generally refer to brightness of a composition comprising brightly labeled reactants. In some embodiments, brightness of a labeled reactant is equal to the product of its quantum yield and extinction coefficient. In some embodiments, the labeled reactants of the disclosure are engineered to maximize quantum yield and/or minimize extinction coefficient values to promote increased brightness.

The brightly labeled reactants of the disclosure are, in some embodiments, engineered to have increased emission brightness and consistent emission lifetime. In some embodiments, two labels of a reactant can interact with one another and/or a surrounding environment such that one or more emission characteristics are inconsistent between the two labels. Inconsistent emission characteristics can be problematic, in some embodiments, where single molecule detection methods rely upon these characteristics to identify a certain type of molecule. For example, in some embodiments, inconsistent emission lifetime can result in lifetime readouts that report two separate clusters of information as opposed to a single grouping of information that would be observed with consistent emission lifetime.

In some embodiments, consistent emission lifetime can involve preserving emission lifetime, e.g., having approximately unchanged emission lifetime relative to a labeled reactant having one fewer label. In some embodiments, emission lifetime of labels in a multiply-labeled reactant is unchanged relative to the same label in a singly-labeled reactant. As described herein, increasing the number of luminescent labels on a single construct to increase brightness can, in some embodiments, result in diminished emission lifetime. In some embodiments, the disclosure provides compositions engineered using specific structural constraints to separate adjacent labels by a certain minimum distance that increases brightness without affecting emission lifetime. In some embodiments, emission lifetime of a multiply-labeled construct is compared to the emission lifetime of a construct having at least one fewer luminescent label (e.g., at least one fewer of the same type of fluorophore dye). In some embodiments, emission lifetime is altered by approximately 30% or less (e.g., increased or decreased by less than 30%, less than 25%, less than 20%, less than 15%, less than 10%, less than 5%, less than 4%, less than 3%, less than 2%, less than 1%, or approximately 0%).

In some aspects, the disclosure relates to the recognition and appreciation that the detectable compositions in a sequencing reaction can be developed to eliminate the need for certain instrument components, thereby moving the technology toward more compact systems. For example, sequencing instruments generally require optical filters to filter the excitation light from causing undesirable detection events at the sensor. Optical filters used to transmit the desired luminescence and sufficiently block the excitation light can be thick, bulky, expensive, and intolerant to variations in the incidence angle of light, preventing miniaturization. The inventors, however, recognized and appreciated that using brightly labeled reactants having preserved lifetimes can reduce the need for such filtering or, in some cases, remove the need for such filters altogether. The bright reactants described herein allow less optical power (e.g., excitation energy) to be used, which reduces scattering and the requirement for filtering as a result.

Aspects of the application provide brightly labeled reactants configured according to the non-limiting diagram shown in FIG. 1A, which depicts two luminescent labels connected to a reactant 180 via a linker 100. As shown, each luminescent label is attached to the linker 100 via a spacer. The spacer, in some embodiments, forms a covalent bridge between label and linker. As such, in some embodiments, the spacer is neither part of the luminescent molecule nor is the spacer part of the linker composition (e.g., the spacer does not contain a monomeric unit of a polymeric or oligomeric linker). A first end of the spacer attaches to a linker attachment site 102, and a second end of the spacer attaches to a label attachment site 122. In some embodiments, the linker attachment site 102 can be approximated by the location of the covalent bond joining an atom of the spacer to an atom of the linker 100. In some embodiments, the linker attachment site 102 occurs at an atom that is within a contiguous chain of the linker 100. In some embodiments, the label attachment site 122 can be approximated by the location of the covalent bond joining an atom of the spacer to an atom of the label. In some embodiments, the label attachment site 122 occurs at the atom of the label that is covalently bound to the atom of the spacer. In some embodiments, the label attachment site 122 occurs at the atom of the spacer that is covalently bound to the atom of the label.

As described elsewhere herein, in some embodiments, linker constructs of the application comprise two or more luminescent labels, where adjacent luminescent labels are described as having attachment sites separated by a minimum distance $d_A$. In some embodiments, each luminescent label is separated from the next by a minimum distance $d_L$. As shown in FIG. 1A, in some embodiments, $d_L$ is the distance between label attachment sites. In some embodiments, label-label separation can be further dictated by the size of each label molecule. Accordingly, in some embodiments, luminescent labels can be described by an approximated or calculated steric volume 112 of an ellipsoid or a spheroid to obtain a measurement for the steric radius, $r_1$. In some embodiments, luminescent labels can be described by an approximated or calculated steric circumference of an ellipse or a circle to obtain a measurement for the steric radius, $r_1$. In some embodiments, steric radius (e.g., $r_1$, $r_2$) can be calculated or approximated as one-half of the longest dimension of a luminescent label. For example, in some embodiments, the chemical structure of a luminescent label is evaluated as a two-dimensional or three-dimensional structure (e.g., based on a thermodynamically-favorable molecular conformation) using software or a suitable method known in the art, and a steric radius (e.g., $r_1$, $r_2$) is determined by calculating one-half of the structure's longest dimension in two-dimensional or three-dimensional space. In some embodiments, labels are separated by minimum distance $d_L$, provided that the aggregate label radii ($r_1+r_2$) are such that the labels do not overlap.

In some embodiments, as illustrated in FIG. 1B, linker configuration and/or spacer rigidity is such that distance between attachment sites $d_A$ can be approximately the same as $d_L$ (e.g., as in construct 150). In some embodiments, linker configuration and/or spacer rigidity is such that distance between attachment sites $d_A$ can be less than minimum distance $d_L$ (e.g., as in construct 152). In some embodiments, linker configuration and/or spacer rigidity is such that distance between attachment sites $d_A$ can be greater than minimum distance $d_L$ (e.g., as in construct 154).

It should be appreciated that, in some embodiments, the concepts described herein can be implemented using any suitable molecular scaffold as a linker 100. In some embodiments, the linker is an organic compound. Examples of organic compounds suitable for use as a linker 100 include, without limitation, polyphenyls, polyalkynes, alpha helix mimetics, and peptidomimetics.

In some embodiments, the linker 100 is an oligomer, e.g., an oligomeric linker comprised of monomeric units. An oligomer, in some embodiments, comprises one or more types of monomeric units. Types of monomeric units can include, by way of example and not limitation, nucleotides (e.g., ribonucleotides, deoxyribonucleotides, and analogs and derivatives thereof), amino acids (e.g., natural and unnatural amino acids), monosaccharides, and organic compounds such as phenyl- and alkynyl-containing compounds. In some embodiments, an oligomer comprises one or more of the same type of monomeric unit. In some embodiments, oligomers comprised of one type of monomeric unit can be referred to as a polymer (e.g., a polymeric linker). In some embodiments, an oligomer comprises two or more different types of monomeric units (e.g., a mix of monomeric units).

In some embodiments, an oligomer (e.g., oligomeric linker or a polymeric linker) contains at least 5 monomeric units. In some embodiments, an oligomer contains at least 10 monomeric units. In some embodiments, an oligomer contains at least 10 and fewer than 200 monomeric units (e.g., at least 10 and fewer than 150 monomeric units, at least 10 and fewer than 100 monomeric units, at least 10 and fewer than 50 monomeric units, at least 10 and fewer than 40 monomeric units, at least 10 and fewer than 30 monomeric units, or at least 10 and fewer than 20 monomeric units).

In some embodiments, the linker (e.g., polymeric linker, oligomeric linker) is a polysaccharide. Examples of polysaccharides suitable for use as a linker 100 are known in the art (e.g., as described in Solid Support Oligosaccharide Synthesis and Combinatorial Carbohydrate Libraries, Wiley 2001).

In some embodiments, the linker (e.g., polymeric linker, oligomeric linker) is a peptide. Non-limiting examples of peptides suitable for use as a linker 100 include, without limitation, oligopeptides, cyclic peptides, and small proteins (e.g., avian pancreatic peptide-based miniature proteins, such as described in Hodges, A. M. and Schepartz, A. (2007) J. Am. Chem. Soc. 129:11024-11025). Methods of engineering geometric constraints into peptide structure are well known in the art and are envisioned to be particularly useful, e.g., to impart rigidity and promote label separation. For example, proline content of a peptide amino acid sequence can be modified to control peptide shape (see, e.g., Kritzer, J. A., et al. (2006) ChemBioChem 7:29-31). Additional non-limiting examples of useful peptide engineering techniques include peptide cyclization (see, e.g., Maltsev, O. V., et al. (2016) Angewandte Chemie 55(4):1535-1539), a-helical peptide constraint via stapling and/or H-bond surrogates (see, e.g., Douse, C. H., et al. (2014) ACS Chem. Biol. 9:2204-2209), peptide constraint via cyclic (3-sheet and (3-hairpin mimics (see, e.g., Gibbs, A. C., et al. (1998) Nat. Struc. Biol. 5:284-288).

In some embodiments, the linker (e.g., polymeric linker, oligomeric linker) is a nucleic acid. In some aspects, a brightly labeled reactant can be designed according to the diagram shown in FIG. 2A, which generically depicts two luminescent labels attached to a core nucleic acid construct. As shown, in some embodiments, at least one luminescent label 210 is attached to a nucleic acid linker 200 at an attachment site 202 via a spacer 220. In some embodiments, the nucleic acid linker 200 comprises at least two hybridized oligonucleotide strands. In some embodiments, the nucleic acid linker 200 comprises at least two luminescent labels, where each luminescent label is separated from the next by a minimum distance $d_L$. In some embodiments, at least two of the luminescent labels are attached to the same oligonucleotide strand, where each attachment site is separated from the next by a minimum distance $d_A$. In some embodiments, the luminescent labels are attached to the oligonucleotide strand via spacers, where each spacer separates a given luminescent label from its attachment site by a minimum distance $d_{AL}$.

In some embodiments, the minimum distances $d_L$, $d_A$, and $d_{AL}$ can be obtained, for example, using theoretical methods known in the art (e.g., computationally or otherwise). In some embodiments, theoretical methods can include any approach that accounts for molecular structure, such as bond lengths, bond angles and rotation, electrostatics, nucleic acid helicity, and other physical factors which might be representative of a molecule in solution. In some embodiments, distance measurements can be obtained experimentally, e.g., by crystallographic or spectroscopic means.

Aspects of the disclosure relate, at least in part, to the discovery that brightly labeled reactants (e.g., labeled nucleotides) having a nucleic acid linker can be designed according to Equation 1:

$$2(d_{AL}) - d_A < 12 \text{ Å}, \qquad \text{Equation 1}$$

where $2(d_{AL}) - d_A$ can be negative. In some embodiments, $d_A$ is greater than 17 angstroms (Å). In some embodiments, $d_A$ is at least 17 Å, but not greater than 350 Å (e.g., $d_A$ is between about 17 and 350 Å, between about 17 and 300 Å, between about 17 and 250 Å, between about 17 and 200 Å, between about 17 and 150 Å, between about 17 and 100 Å, or between about 17 and 50 Å).

In yet other aspects, labeled nucleotides of the disclosure can be designed according to Equation 2:

$$2(d_{AL})/d_A < 1. \qquad \text{Equation 2}$$

In some embodiments, $2(d_{AL})/d_A$ is less than 1, preferably less than 0.5. In some embodiments $2(d_{AL})/d_A$ is less than 0.1.

In some embodiments, labeled nucleotides of the disclosure can be designed according to Equation 3:

$$[2(d_{AL}) + LLD]/d_A < 1, \qquad \text{Equation 3}$$

where LLD is a distance that represents the longest label dimension (LLD). In some embodiments, $[2(d_{AL}) + LLD]/d_A$ is less than 0.5. In some embodiments, $[2(d_{AL}) + LLD]/d_A$ is less than 0.2. In some embodiments, $[2(d_{AL}) + LLD]/d_A$ is less than 0.1.

In some embodiments, minimum distance $d_{AL}$ is measured from an approximately central atom of a luminescent label 210 to an atom on the oligonucleotide strand to which the spacer 220 is attached. In some embodiments, minimum distance $d_{AL}$ is measured from the center of the luminescent label 210 (e.g., approximated based on the center of mass of the luminescent molecule, or some other method known in the art or described elsewhere herein) to an atom on the oligonucleotide strand to which the spacer 220 is attached. In some embodiments, minimum distance $d_{AL}$ is measured as the length of spacer 220 (e.g., measured from an atom of spacer 220 that attaches luminescent label 210 to an atom of spacer 220 that attaches to nucleic acid 200). In some embodiments, minimum distance $d_A$ is measured as the distance between atoms on the oligonucleotide backbone to which the spacers are covalently bound (e.g., between carbon atoms of abasic attachment sites). In some embodiments, minimum distance $d_A$ is measured as the distance between the labeled bases on the oligonucleotide strand (e.g., between atoms on nucleobases of basic attachment sites).

In some embodiments, minimum distance $d_L$ is measured as the distance between approximately central atoms of adjacent luminescent labels. In some embodiments, adjacent luminescent labels are separated by a distance $d_L$ of approximately 6 angstroms. In some embodiments, distance $d_L$ is at least 6 angstroms (e.g., at least 6, at least 7, at least 8, at least 9, at least 10, at least 11, or at least 12 angstroms). In some embodiments, minimum distance $d_L$ is measured as an approximation, which may or may not factor in spacer configuration, spacer flexibility, or nucleic acid flexibility.

Among other aspects, the disclosure provides general strategies for developing the distance $d_L$ between luminescent labels such that multiply-labeled reactants can be engineered to have maximized brightness without compromising emission lifetime. In some embodiments, adjacent luminescent labels of sufficient proximity can interact such that a quenching effect occurs, resulting in diminished and/or inconsistent values for emission lifetime. Accordingly, the general design strategies provided herein can, in some embodiments, involve structural constraints that limit the extent of interactions between adjacent luminescent labels.

In some embodiments, a luminescent label can interact with guanine nucleobases of a nucleic acid linker via radiative and/or non-radiative decay to effect diminished and/or inconsistent emission lifetime. In some embodiments, luminescent label attachment sites are developed by minimizing G/C content in regions surround the attachment sites. As such, in some embodiments, attachment sites are located in A/T-rich regions of an oligonucleotide strand. In some embodiments, each attachment site is at least 2 nucleotides separated from a G or C nucleotide on the oligonucleotide strand (e.g., 2, 3, 4, 5, 6, 7, 8, 9, or more than 10 nucleotides separated from a G or C nucleotide). Thus, in some embodiments, each attachment site is flanked by at least 2 consecutive nucleotides selected from A or T.

In certain embodiments, the distance between attachment sites of an oligonucleotide strand can be described by the number of intervening unlabeled bases (e.g., intervening nucleotides). In some embodiments, attachment sites on an oligonucleotide strand are separated by at least 5 unlabeled bases (e.g., at least 5, at least 6, at least 7, at least 8, at least 9, or at least 10 unlabeled bases). In some embodiments, attachment sites are separated by 6, 7, 8, or 9 unlabeled bases. In some embodiments attachment sites are separated by between 5 and 100 unlabeled bases (e.g., between 5 and 80, between 5 and 60, between 5 and 40, between 5 and 20, or between 5 and 10 unlabeled based) on the oligonucleotide strand.

In some embodiments, the design principles described herein allow for the addition of successive luminescent labels to a labeled reaction component for increasing brightness and/or luminescent intensity. In some embodiments, techniques of the present application provide multiply-labeled reaction components having brightness and/or luminescent intensity according to the formula $L_n(x)$, where $L_n$ is equal to the total number of luminescent labels on a labeled reactant and x is equal to the measured brightness or fluorescent intensity of the corresponding singly-labeled reactant. Accordingly, in some embodiments, a two-dye labeled reaction component possesses brightness and/or luminescent intensity that is doubled compared to the one-dye labeled analog. In some embodiments, a three- or four-dye labeled reaction component possesses brightness and/or luminescent intensity that is tripled or quadrupled, respectively, compared to the one-dye labeled analog. In some embodiments, the brightly labeled reactants described herein exhibit brightness and/or luminescent intensity that is at least 70%, at least 80%, at least 90%, at least 95%, at least 98%, or at least 99% of the value predicted by $L_n(x)$.

In some embodiments, the nucleic acid linkers provided herein comprise an oligonucleotide strand having at least two luminescent labels. FIG. 2B generically depicts a single-stranded nucleic acid linker 250 attached to two luminescent labels. As shown, a single-stranded linker can possess a relatively high degree of flexibility that may promote interaction between labels. In some embodiments, brightly labeled reactants having consistent and/or preserved lifetime can be generated using single-stranded linker constructs, e.g., by utilizing certain labels that do not interact to produce a quenching effect, such as cyanine-based dyes. However, for several classes of dyes, the promotion of label-label proximity due to linker flexibility may produce diminished and/or inconsistent emission lifetimes. Accordingly, in some embodiments, the labeled oligonucleotide strand is hybridized with one or more oligonucleotide strands to decrease overall nucleic acid linker flexibility.

In some embodiments, strand hybridization was used as a general design strategy to develop an appropriate distance $d_L$ between luminescent labels on a nucleic acid linker. In some embodiments, strand hybridization was used to increase rigidity in specific regions of nucleic acids (e.g., within a labeled region and/or in a region separating a labeled region from a reactant). FIG. 2B generically depicts a double-stranded nucleic acid linker 252 that includes a hybridized oligonucleotide strand to rigidify the labeled region and thereby decrease strand flexibility that might otherwise promote label-label interaction.

As illustrated by nucleic acid linker 252, in some embodiments, luminescent label movement about an attachment point can promote label-label proximity. Also as shown, in some embodiments, label movement about an attachment site can result in a label being in closer proximity to an oligonucleotide strand of the nucleic acid linker. In some embodiments, an oligonucleotide strand can interact with a luminescent label to produce inconsistent and/or diminished emission lifetime measurements. Accordingly, in some embodiments, nucleic acid linkers described herein comprise spacers having certain lengths, rigidities, sites of attachment, and/or configurations that limit the extent of label-label and/or linker-label interactions.

In some embodiments, separation distance between luminescent labels can be defined in the context of the volume of space in which the labels are present relative to one another. For example, FIG. 2B depicts a diagram 254 that illustrates an example of how distance $d_L$ can be measured. In some embodiments, each luminescent label can be defined by a steric volume 212. In some embodiments, steric volume 212 is approximated as a sphere of radius 212-$r$ or as an otherwise ellipsoidal shape. In some embodiments, each luminescent label comprises a steric volume 212 having a center point that is at least 5 angstroms separated from that of any other label (e.g., the center points of adjacent labels are separated by at least 5 angstroms). A center point of a luminescent label can be any suitable center of the label, including, e.g., a center of mass or a geometric center of the label. In some embodiments, a center point of a luminescent label can be determined by calculating or approximating radius 212-$r$, as illustrated in FIG. 2B. In some embodiments, a center point of a luminescent label can be calculated or approximated as one-half of the longest dimension of a luminescent label (e.g., as described elsewhere herein for $r_1$ and $r_2$ of FIG. 1A).

In some embodiments, distance between adjacent luminescent labels ($d_L$) can be measured as the distance between the centers of mass of the adjacent luminescent labels. Center of mass, in some embodiments, refers to the average position of all atoms in a luminescent label, weighted according to their masses. Methods of calculating center of mass of are known in the art (see, e.g., Leach, A. R. Molecular Modelling: Principles and Applications ($2^{nd}$ edition), Prentice-Hall 2001; Guenza, M. (2002) Macromolecules 35(7):2714-2722).

In some embodiments, distance between adjacent luminescent labels (dL) can be measured as the distance between the geometric centers of the adjacent luminescent labels. A geometric center of a molecule, in some embodiments, refers to the average position of all atoms of the molecule (e.g., all atoms in a luminescent label), wherein the atoms are not weighted. Thus, in some embodiments, the geometric center of a molecule refers to a point in space that is an average of the coordinates of all atoms in the molecule.

In some embodiments, steric volume 212 is calculated more precisely using any suitable method known in the art. For example, molar refractivity factors in properties that include polarizability, and can be calculated according to the equation:

$$\text{Molar Refractivity}=[(n^2-1)/(n^2+2)]\times(MW/d),$$

where n=index of refraction; MW=molecular weight; and d=density.

In some embodiments, steric volume 212 of a label can be calculated computationally to include additional and/or more complex factors. For example, Verloop steric factor provides spatial dimensions of a molecule based on bond angles, van der Waals radii, bond lengths, and possible conformations (e.g., see Harper, K. C., et al. (2012) Nature Chemistry 4, 366-374).

In some embodiments, luminescent label movement about an attachment site may be factored into the separation distance $d_L$. As shown in FIG. 2B, the range of label movement about each attachment site can be defined, in some embodiments, based on spacer length and steric volume of the label. This theoretical range of movement is illustrated by dashed lines. It should be appreciated that, in some embodiments, a variety of the compositions and design strategies described herein can advantageously limit the extent to which the range of movement approaches the overlapping region shown. For example, in some embodiments, spacer rigidity, spacer length, and attachment site separation can each be addressed in accordance with the disclosure to limit the extent to which the label is likely to approach the overlapping region. It should also be appreciated that diagram 254 is intended for illustrative purposes, e.g., as labels are not necessarily required to come into physical contact for radiative and/or non-radiative decay to occur.

In some embodiments, the range of motion of labels depicted in diagram 254 can be generally referred to as a spatial volume, e.g., an area of space having regions of varying probability that the label could be present at a point in space at a given point in time. In some embodiments, each label occupies a spatial volume that is substantially non-overlapping with that of any other luminescent label. In some embodiments, each label occupies a spatial volume that is substantially free of any other label.

In some embodiments, relative attachment sites for luminescent labels can be designed in view of the helical structure of a double-stranded linker. FIG. 2C depicts an example of a nucleic acid 260 having two labels separated by a distance, x. Nucleic acid 262 (drawn approximately to scale), is attached to two luminescent labels at attachment sites separated by roughly half as many bases as nucleic acid 260, but the relative attachment site locations along the helix result in a label separation distance through space of approximately 2x. As shown, in some embodiments, the nucleic acid linker can further limit the extent of radiative and/or non-radiative decay between labels by acting as a steric barrier between labels.

In some embodiments, the term "steric barrier" refers to a linker or a portion of a linker (e.g., a nucleic acid linker or a portion thereof) positioned between a luminescent label attached to the linker and some other attachment of the linker. Without wishing to be bound by theory, it is thought that a steric barrier can absorb, deflect, or otherwise block radiative and/or non-radiative decay emitted by the luminescent label. In some embodiments, the steric barrier prevents or limits the extent to which one or more luminescent labels interact with one or more other luminescent labels. In some embodiments, the steric barrier prevents or limits the extent to which one or more luminescent labels interact with one or more reactants. In some embodiments, the steric barrier prevents or limits the extent to which one or more luminescent labels interact with one or more molecules associated with a reactant (e.g., a polymerase bound to the reactant). Accordingly, in some embodiments, the term steric barrier can generally refer to a protective or shielding effect that is provided by some portion of a nucleic acid linker.

In some embodiments, one or more structural motifs can function as a steric barrier. For example, in some embodiments, a helix formed by a double-stranded nucleic acid linker functions as a steric barrier. In some embodiments, a stem-loop or a portion thereof (e.g., a stem, a loop) functions as a steric barrier. In some embodiments, a three-way junction (e.g., as in a nucleic acid having two or more stem-loops) functions as a steric barrier. In some embodiments, a hybridized strand having no attachments (e.g., a support strand) functions as a steric barrier. In some embodiments, a spacer functions as a steric barrier.

In some embodiments, the brightly labeled reactants described herein provide separation between luminescent labels and a reactant. In some embodiments, a nucleic acid 264 comprises a nucleoside polyphosphate 280 reactant that serves as a substrate for a polymerase 290 in a synthesis reaction. In some embodiments, labels in close proximity to a polymerase active site can induce polymerase photodamage (e.g., via non-radiative decay or otherwise), which can be detrimental to polymerase activity. As shown, nucleic acid 266 is attached to a reactant such that at least a portion of the linker is in an intervening region between the label and the reactant. As such, in some embodiments, a nucleic acid linker can function as a steric barrier to further protect the polymerase from label-induced photodamage. This effect of polymerase protection can, in some embodiments, occur through label-reactant spatial separation and/or the presence of a steric barrier between label and reactant. Polymerase protection is described in further detail in co-pending U.S. patent application Ser. No. 15/600,979), the content of which is incorporated herein by reference in its entirety.

In some embodiments, the size and configuration of nucleic acid linkers (e.g., one or more oligonucleotide strands and/or one or more spacers of a nucleic acid linker) determines the distance between a luminescent label and a nucleoside polyphosphate. In some embodiments, the distance is about 1 nm or 2 nm to about 20 nm. For example, more than 2 nm, more than 5 nm, 5-10 nm, more than 10 nm, 10-15 nm, more than 15 nm, 15-20 nm, more than 20 nm. However, the distance between the luminescent label and the nucleoside polyphosphate cannot be too long since certain detection techniques require that the luminescent label be within a defined illumination volume to be excited (e.g., when the nucleoside polyphosphate is held within the active site of a polymerase). Accordingly, in some embodiments, the overall distance is less than 30 nm, less than 25 nm, around 20 nm, or less than 20 nm.

In some embodiments, other features of the compositions described herein can be implemented to promote label-reactant separation to minimize the potential for label-induced photodamage, e.g., spacer length, spacer rigidity, attachment site location. In some embodiments, reactant connectivity to the nucleic acid linkers described herein can be modified relative to a luminescent label to promote label-reactant separation. FIG. 3A generically depicts nucleic acid linkers having same-strand or opposite strand label-reactant connectivity. In some embodiments, a nucleic acid 300 comprises two or more luminescent labels and a reactant attached to the same oligonucleotide strand. In some embodiments, same-strand connectivity results in a covalent connection between label and reactant.

In some embodiments, a nucleic acid 302 comprises two or more luminescent labels and a reactant attached to different oligonucleotide strands. In some embodiments, opposite strand connectivity results in a non-covalent connection between label and reactant. In some embodiments, opposite strand connectivity of label and reactant occurs through hybridization of a label-attached oligonucleotide strand and a reactant-attached oligonucleotide strand. As shown, in some embodiments, nucleic acid linkers of the disclosure comprise a label-reactant separation distance $d_{LR}$. In some embodiments, $d_{LR}$ is the distance between reactant and the nearest luminescent label. In some embodiments, $d_{LR}$ is measured from label attachment site to reactant attachment site. In some embodiments, $d_{LR}$ is measured from the luminescent molecule of a label to the reactant. In some embodiments, $d_{LR}$ is at least 1 nm. In some embodiments, $d_{LR}$ is between about 1 nm to about 10 nm (e.g., approximately 1 nm, 2 nm, 3 nm, 4 nm, 5 nm, 6 nm, 7 nm, 8 nm, 9 nm, 10 nm, or more than 10 nm). In some embodiments, $d_{LR}$ is between about 2 nm to about 30 nm (e.g., between about 2 and 25 nm, between about 2 and 20 nm, between about 2 and 15 nm, between about 2 and 10 nm, between about 2 and 5 nm, between about 5 and 10 nm, between about 10 and 20 nm, between about 5 and 30 nm, between about 15 and 30 nm, or between about 20 and 30 nm).

FIG. 3B depicts examples of non-limiting distance specifications used in the design of brightly labeled reactants. In some embodiments, a nucleic acid linker 304 is attached to two luminescent labels and a nucleoside hexaphosphate (e.g., a reactant) via same-strand connectivity. In some embodiments, as shown, & is approximately 1 nm and $d_{LR}$ is approximately 7 nm. In some embodiments, the brightly labeled reactants of the disclosure comprise more than two luminescent labels. For example, in some embodiments, a nucleic acid linker 306 is attached to three luminescent labels and a nucleoside hexaphosphate (e.g., a reactant) via same-strand connectivity. As shown, in some embodiments, constructs having more than two luminescent labels attached at more than two attachment sites will necessarily have more than one separation distance $d_L$. In some embodiments, each separation distance $d_L$ on a single construct can be independently designed according to the description herein. In some embodiments, each label separation distance $d_L$ can be designed to be approximately the same. For example, in some embodiments, each occurrence of separation distance $d_L$ is approximately 3.5 nm and $d_{LR}$ is approximately 7 nm.

In some embodiments, the brightly labeled reactants of the application comprise two or more luminescent labels attached via different oligonucleotide strands. For example, in some embodiments, a nucleic acid linker 308 comprises four luminescent labels attached via separate oligonucleotide strands. In some embodiments, an unlabeled oligonucleotide strand of nucleic acid linker 308 comprises a first portion that is complementary to a first oligonucleotide strand attached to two luminescent labels and a nucleoside polyphosphate. The unlabeled oligonucleotide strand further comprises a second portion that is complementary to a second oligonucleotide strand attached to two luminescent labels. As shown, in some embodiments, luminescent label attachment sites within each labeled strand are separated by 9 nucleotides. In some embodiments, separation between nearest attachment sites on non-contiguous labeled strands can be the same or different (e.g., as shown by a 10-nucleotide separation).

The non-limiting generic nucleic acid linker 304 having same-strand label-reactant connectivity was used as a basis for generating the labeled nucleoside polyphosphate shown in FIG. 3C. As shown, the nucleic acid linker of FIG. 3C comprises two hybridized oligonucleotide strands. In accordance with certain embodiments of the disclosure, two luminescent labels were attached at abasic sites within a first oligonucleotide strand of the linker. Click chemistry techniques, as described elsewhere herein as a general attachment strategy, were used to attach a nucleoside polyphosphate to the same oligonucleotide strand. A second oligonucleotide strand was hybridized to the first strand to promote constrained spatial conformations of the attached components in accordance with theory described herein. The construct of FIG. 3C was successfully used in a single molecule sequencing run with other labeled nucleoside polyphosphates (FIG. 3D). A similarly designed construct was generated having opposite-strand connectivity and is shown in FIG. 3E.

FIG. 3E depicts an example structure of a nucleic acid linker that non-covalently connects a nucleoside polyphosphate (e.g., a reactant) with luminescent labels. As shown, a first oligonucleotide strand attached to two luminescent labels at abasic attachment sites was hybridized with a second oligonucleotide strand attached to a nucleoside hexaphosphate at a terminal attachment site. In some embodiments, the design strategies provided in the present disclosure to generate brightly labeled reactants is contemplated to include alternative label conjugation strategies, such as labels integrated into a linker (e.g., integrated into an oligomeric or polymeric linker, such as an oligonucleotide strand). For example, FIG. 3F depicts an example of a nucleic acid linker having two labels attached within an oligonucleotide strand.

As shown in FIG. 3F, in some embodiments, a brightly labeled reactant comprises two luminescent labels attached within an oligonucleotide strand (e.g., integrated into the strand). In some embodiments, such conjugation strategies can be implemented with luminescent molecules that do not interact via radiative and/or non-radiative decay, such as cyanine-based dyes (e.g., as shown in FIG. 3F, boxed area). In some embodiments, the number of luminescent molecules attached within an oligonucleotide strand may be limited only by the size of the oligonucleotide strand. Thus, in some embodiments, a brightly labeled reactant comprises more than two luminescent labels (e.g., two, three, four, five, six, or more than six luminescent labels) attached within an oligonucleotide strand. The construct depicted in FIG. 3F was successfully utilized in a sequencing run with three other brightly labeled nucleoside polyphosphates (FIG. 3G).

The disclosure relates, in some aspects, to the discovery that nucleic acid linkers can be engineered having structurally-constrained conformations that provide scaffolds for brightly labeled reactants having consistent and/or preserved emission lifetime. As described herein, in some embodiments, oligonucleotide strand hybridization is one general strategy that promotes constrained conformations for purposes of label separation. In some embodiments, oligonucleotide strand hybridization involves hybridization of different oligonucleotide strands. In some embodiments, oligonucleotide strand hybridization involves self-strand hybridization (e.g., self-hybridizing within a single strand). In some embodiments, self-strand hybridization may limit nucleic acid linker flexibility, as described elsewhere herein with regard to separate strand hybridization. In some embodiments, self-strand hybridization is used to form one or more stem-loop structures in a nucleic acid linker.

A stem-loop, or hairpin loop, is an unpaired loop of nucleotides on an oligonucleotide strand that is formed when the oligonucleotide strand folds and forms base pairs with another section of the same strand. In some embodiments, the unpaired loop of a stem-loop comprises three to ten nucleotides. Accordingly, a stem-loop can be formed by two regions of an oligonucleotide strand having inverted complementary sequences that hybridize to form a stem, where the two regions are separated by the three to ten nucleotides that form the unpaired loop. In some embodiments, the stem can be designed to have one or more G/C nucleotides, which can provide added stability with the addition hydrogen bonding interaction that forms compared to A/T nucleotides. In some embodiments, the stem comprises G/C nucleotides immediately adjacent to an unpaired loop sequence. In some embodiments, the stem comprises G/C nucleotides within the first 2, 3, 4, or 5 nucleotides adjacent to an unpaired loop sequence.

In some embodiments, an unpaired loop of a stem-loop nucleic acid linker comprises one or more luminescent labels. Thus, in some embodiments, one or more label attachment sites are present in an unpaired loop. In some embodiments, an attachment site occurs at an abasic site in the unpaired loop. In some embodiments, an attachment site occurs at a base of the unpaired loop. In some embodiments, a loop comprises an A/T/U-rich sequence, e.g., due to a quenching effect observed with guanine, as described elsewhere herein. In some embodiments, the attachment site occurs at an A, T, or U nucleotide in the unpaired loop. In some embodiments, at least four consecutive A, T, or U nucleotides occur on either side of an attachment site. In some embodiments, an unpaired loop comprises less than 33% G/C content (e.g., less than 30%, less than 20%, less than 10%, or 0% G/C content).

In some embodiments, a luminescent label is attached to an unpaired loop of a stem-loop (e.g., the label attachment site occurs within the loop). For example, FIG. 4A generically depicts an example of a labeled reactant having a stem-loop nucleic acid linker 400. As shown, in some embodiments, a first oligonucleotide strand 410 self-hybridizes to form a stem-loop. In some embodiments, the self-hybridized portion of the oligonucleotide strand forms a stem 412 of the stem-loop. In some embodiments, self-strand hybridization results in the formation of a loop 414 of a stem-loop (e.g., an unpaired loop). In some embodiments, the first oligonucleotide strand 410 is further hybridized with a second oligonucleotide strand 420 attached to a reactant. Thus, in some embodiments, a stem-loop nucleic acid linker non-covalently connects a luminescent label to a reactant via opposite strand connectivity. It should be appreciated that, in some embodiments, a self-hybridized oligonucleotide strand (e.g., a strand having a stem-loop) attached to a luminescent label can be attached to one or more reactants via same-strand connectivity.

In some embodiments, two or more luminescent labels are attached to a stem-loop nucleic acid linker. For example, in some embodiments, a stem-loop nucleic acid linker 402 is attached to two luminescent labels. As shown, in some embodiments, attachment sites for the two luminescent labels occur within the loop of the stem-loop. In some embodiments, the stability provided by the self-hybridized stem region results in the loop region having a relatively low level of flexibility. In some embodiments, luminescent label attachment sites within an unpaired loop can be designed to promote a favorable label-label spatial separation and/or a favorable label-reactant spatial separation. The example provided by the non-limiting stem-loop nucleic acid linker 402 depicts label attachment sites that are separated from one another by a distance approximating the diameter of the loop. In some embodiments, this design can maximize label-label separation through space. In some embodiments, this design further limits the extent of label-label interaction through a steric barrier effect provided by the loop, as described elsewhere herein. In some embodiments, a stem-loop nucleic acid linker comprises two or more stem-loops (FIG. 4B).

As shown in FIG. 4B, in some embodiments, a stem-loop nucleic acid linker 404 comprises two stem-loops. In some embodiments, formation of two stem-loops results in a nucleic acid linker having a Y-shape such that a three-way junction 410 is formed. In some embodiments, three-way junctions are contemplated as a general design strategy due to the relative stability and geometrically constrained conformation that results from these features. In some embodiments, a stem-loop nucleic acid linker 404 comprises one luminescent label attached to each loop. In some embodiments, a stem-loop nucleic acid 404 non-covalently connects a luminescent label and a reactant through opposite strand connectivity, e.g., one or more labels attached to a first oligonucleotide strand hybridized with a second oligonucleotide strand attached to one or more reactants. In some embodiments, a stem-loop nucleic acid 406 connects a luminescent label and a reactant via same-strand connectivity (e.g., one or more labels and one or more reactants attached to the same oligonucleotide strand). Stem-loop nucleic acid 406 depicts an example of non-limiting distance specifications used in the design of brightly labeled reactants having a three-way junction. For example, these approximate distances were used as a basis for generating the labeled nucleoside polyphosphate shown in FIG. 4C. The construct of FIG. 4C was successfully used in a single molecule sequencing run with other labeled nucleoside polyphosphates (FIG. 4D).

In some embodiments, one or more luminescent labels are attached to a stem of a stem-loop. In some embodiments, a stem-loop of a nucleic acid linker does not comprise a luminescent label. In some embodiments, a stem-loop of a nucleic acid linker comprises an unpaired region within the stem (e.g., a "bulge loop"). In some embodiments, one or more unlabeled structural motifs, such as stem-loops, are included in the nucleic acid linker (e.g., in a position on the nucleic acid linker such that a that is between the one or more luminescent labels and the one or more nucleoside polyphosphates). In such embodiments, the one or more unlabeled structural motifs can provide a steric barrier effect, as described elsewhere herein.

In some embodiments, a stem-loop nucleic acid linker comprises a first oligonucleotide strand attached to a luminescent label. In some embodiments, the luminescent label is attached at an attachment site on the first oligonucleotide strand via a spacer. In some embodiments, the first oligonucleotide strand forms a stem-loop secondary structure having a stem and a loop (e.g., an unpaired loop). In some embodiments, the loop comprises the attachment site. In some embodiments, the nucleic acid linker comprises a second oligonucleotide strand hybridized with the first oligonucleotide strand. In some embodiments, the second oligonucleotide strand is attached to a nucleoside polyphosphate. In some embodiments, the nucleoside polyphosphate is attached to the second oligonucleotide strand via a spacer. In some embodiments, the first oligonucleotide strand is of the structure:

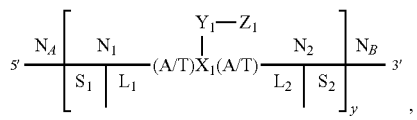

wherein $N_A$ and $N_B$ are each a consecutive sequence of 5 to 40 nucleotides independently selected from A, U, T, G, and C, wherein the second oligonucleotide strand is hybridized to either a 5' portion of $N_A$ or a 3' portion of $N_B$; brackets denote a region that forms y stem-loops, each stem-loop having a stem and a loop, wherein y is 1 to 3; $N_1$ and $N_2$ are each a consecutive sequence of 5 to 20 nucleotides independently selected from A, U, T, G, and C, wherein: a 5' portion of $N_1$ ($S_1$) and a 3' portion of $N_2$ ($S_2$) are reverse complementary or partially reverse complementary and are capable of hybridizing with one another to form the stem motif; a 3' portion of $N_1$ ($L_1$), a 5' portion of $N_2$ ($L_2$), and an intervening region form the loop motif when $S_1$ and $S_2$ hybridize to form the stem motif; (A/T) is a nucleotide selected from A, T, and U; $X_1$ is the attachment site on the second oligonucleotide strand; $Y_1$ is the first linker; and $Z_1$ is the luminescent label.

As described herein, aspects of the disclosure relate to geometrically constrained linker configurations for connecting one or more luminescent labels to one or more reactants (e.g., one or more nucleoside polyphosphates). In some embodiments, a geometrically constrained configuration refers to a nucleic acid linker having two or more luminescent labels, where the luminescent labels are spatially separated by a symmetrical configuration. In some aspects, the brightly labeled reactants of the disclosure comprise nucleic acid linkers resembling a tree-shaped configuration as depicted in FIG. 5A. In some embodiments, tree-shaped linker 500 comprises a tris-labeled nucleic acid linker connected to a reactant (e.g., a nucleoside polyphosphate). As shown, in some embodiments, tree-shaped linker 500 comprises three main oligonucleotide components. In some embodiments, a first oligonucleotide component 510 comprises four oligonucleotide strands covalently attached via a branched linker. In some embodiments, three of the oligonucleotide strands of component 510 are each attached to a luminescent label (e.g., via terminal attachment or other conjugation strategy described herein). Accordingly, in some embodiments, the three labeled oligonucleotide strands of component 510 are generally referred to as a labeled portion of component 510. In some embodiments, a fourth oligonucleotide strand of component 510 is unlabeled. In some embodiments, the fourth oligonucleotide strand is hybridized with a second oligonucleotide component 520. In some embodiments, the second oligonucleotide component 520 of nucleic acid linker 500 is attached to a reactant (e.g., via terminal attachment or other conjugation strategy described herein). In some embodiments, a third oligonucleotide component 530 is hybridized with the three oligonucleotide strands of the labeled portion of component 510. In some embodiments, the third oligonucleotide component 530 is referred to as a support strand, as its hybridization with component 510 provides structural rigidity in the labeled region to promote spatial separation of the luminescent labels.

As should be appreciated, any of the linker design strategies described herein can be applied to a tree-shaped nucleic acid linker or any other nucleic acid linker configuration contemplated by the disclosure (e.g., strand connectivity, spacer properties and spacer configurations, label-label separation, label-reactant separation, three-way junctions, etc.). Tree-shaped nucleic acid 502 depicts an example of non-limiting distance specifications used in the design of brightly labeled reactants having a tree-shaped nucleic acid linker. As an illustrative example, these approximate distances were used as a basis for generating the labeled nucleoside polyphosphate shown in FIG. 5B. As shown, in some embodiments, a tree-shaped nucleic acid can comprise more than one reactant (e.g., two nucleoside polyphosphates, or more than two nucleoside polyphosphates).

In some embodiments, a tree-shaped nucleic acid linker is described in terms of first and second oligonucleotide strands that comprise the hybridized portion having a reactant. For example, in some embodiments, a tree-shaped nucleic acid linker comprises a first oligonucleotide strand attached to two or more branching oligonucleotide strands at a terminal end of the first oligonucleotide via a coupling compound (e.g., a branched coupler). In some embodiments, each branching oligonucleotide strand is attached to a luminescent label. In some embodiments, the first oligonucleotide strand is hybridized with a second oligonucleotide strand attached to a reactant (e.g. a nucleoside polyphosphate). In some embodiments, a third oligonucleotide strand (e.g., a third oligonucleotide component) is hybridized with the two or more branching oligonucleotide strands. In some embodiments, the coupling compound is of the below structure:

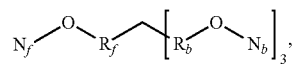

wherein $N_f$ is the first oligonucleotide strand; $N_b$ is a branching oligonucleotide strand; $R_f$ and $R_b$ are each, independent from one another, a bond or a linking group selected from the group consisting of substituted or unsubstituted alkylene; substituted or unsubstituted alkenylene; substituted or unsubstituted alkynylene; substituted or unsubstituted heteroalkylene; substituted or unsubstituted heteroalkenylene; substituted or unsubstituted heteroalkynylene; substituted or unsubstituted heterocyclylene; substituted or unsubstituted carbocyclylene; substituted or unsubstituted arylene; substituted or unsubstituted heteroarylene; and combinations thereof; and each instance of O is an oxygen atom of either a 5' phosphate group or a 3' hydroxyl group of an adjacent oligonucleotide strand.

In some aspects, the disclosure provides brightly labeled reactants having star-shaped nucleic acid linkers. As shown in FIG. 6A, star-shaped nucleic acid linkers can provide symmetrically-arranged reactants at an external region of the linker and one or more luminescent labels nearer to a core region of the configuration. In this way, in some embodiments, reactants may be more susceptible to reacting, e.g., with a polymerase. In some embodiments, the nucleotide content surrounding the luminescent label attachment sites near the core region are selected according to specifications described herein (e.g., low G/C content to avoid a quenching effect between a label and the linker). In some embodiments, a star-shaped nucleic acid linker 600 comprises a Y-shaped oligonucleotide component having three oligonucleotide strands attached via a branched linker. In some embodiments, each of the three oligonucleotide strands of the Y-shaped oligonucleotide component is attached (e.g., terminally) to a reactant. In some embodiments, each of the three oligonucleotide strands of the Y-shaped oligonucleotide component is hybridized with an oligonucleotide strand. In some embodiments, one of the hybridized oligonucleotide strands is attached to a luminescent label. In some embodiments, however, two or three of the hybridized oligonucleotide strands are each attached to a luminescent label.

In some embodiments, the Y-shaped oligonucleotide component of a star-shaped nucleic acid linker is attached to more than three reactants. For example, in some embodiments, a brightly labeled reactant having a star-shaped nucleic acid linker 602 comprises two reactants at each of two oligonucleotide strands of the Y-shaped oligonucleotide component. In some embodiments, the two reactants are attached to strands of the Y-shaped oligonucleotide component that are hybridized with unlabeled strands, as shown.

In some embodiments, a star-shaped nucleic acid linker comprises a labeled oligonucleotide component and a reactant oligonucleotide component, where each oligonucleotide component comprises a Y-shaped oligonucleotide. For example, in some embodiments, a star-shaped nucleic acid linker 604 comprises a first Y-shaped oligonucleotide component attached to three luminescent labels. In some embodiments, each luminescent label is attached to each oligonucleotide strand of the first Y-shaped component. In some embodiments, as shown, each luminescent label is attached near a core region of the first Y-shaped oligonucleotide component. In some embodiments, star-shaped nucleic acid linker 604 is hybridized with a second Y-shaped oligonucleotide component attached to three reactants. In some embodiments, each reactant is attached to each oligonucleotide strand of the second Y-shaped component. In some embodiments, as shown, each reactant is attached at an external region of the first Y-shaped oligonucleotide component (e.g., via terminal attachment sites). Star-shaped nucleic acid 606 depicts an example of non-limiting distance specifications used in the design of brightly labeled reactants having a star-shaped nucleic acid linker. An example structure of a brightly labeled reactant having a star-shaped nucleic acid linker generated in accordance with the disclosure is shown in FIG. 6B.

In some embodiments, a star-shaped nucleic acid linker can be described in terms of a covalent coupling compound used in a Y-shaped oligonucleotide component of the linker. For example, in some embodiments, a brightly labeled reactant having a star-shaped nucleic acid linker comprises a first oligonucleotide component that comprises three or more oligonucleotide strands extending from a covalent coupling compound. In some embodiments, at least one of the oligonucleotide strands is attached to a reactant (e.g., a nucleoside polyphosphate). In some embodiments, two or more (e.g., 2, 3, 4, 5 or more) of the oligonucleotide strands of the first oligonucleotide component are each attached to one or more reactants. In some embodiments, the first oligonucleotide component is hybridized with a second oligonucleotide component. In some embodiments the second oligonucleotide component comprises at least one oligonucleotide strand attached to a luminescent label. In some embodiments, the second oligonucleotide component comprises three or more oligonucleotide strands extending from a covalent coupling compound. In some embodiments, two or more (e.g., 2, 3, 4, 5 or more) of the oligonucleotide strands of the second oligonucleotide component are each attached to a luminescent label.

In some aspects, the brightly labeled reactants of the disclosure comprise a nucleic acid linker having a tetrahedral core. As illustrated by the example structure of FIG. 6C, a tetrahedral core refers to a four-way covalent coupling compound that promotes a symmetrically-constrained spatial arrangement of one or more luminescent labels and one or more nucleoside polyphosphates. FIG. 6D depicts an example of a reaction scheme that can be used to synthesize the example structure shown in FIG. 6C. In some embodiments, a tetrahedral core is contemplated for use in combination with any of one or more of the brightly labeled reactant design strategies described herein. As an example, the symmetrically-constrained benefits provided by a tetrahedral core was implemented with three-way junctions described herein to generate the brightly labeled reactant shown in FIG. 6E. As shown, in some embodiments, attachment of a luminescent label at or near a three-way junction can advantageously provide a steric effect, as described elsewhere herein.

In some embodiments, the disclosure contemplates further symmetrically-constrained configurations using core chemical couplers that allow for symmetrical attachment. In some embodiments, for example, a brightly labeled reactant comprises a cyclodextrin-based core. An example synthetic scheme for generating a cyclodextrin-based nucleic acid linker having three-way junctions is shown in FIG. 7. An example structure of a cyclodextrin coupling compound is provided in Table 1 along with examples of other coupling compounds that may be used for covalent linkage of three or more oligonucleotide strands in accordance with embodiments described herein.

TABLE 1
Examples of coupling compounds for linking oligonucleotide strands
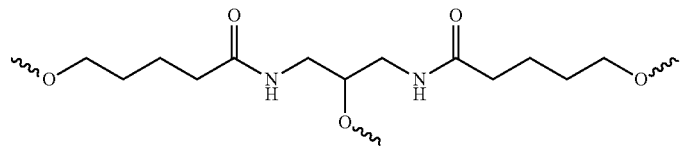
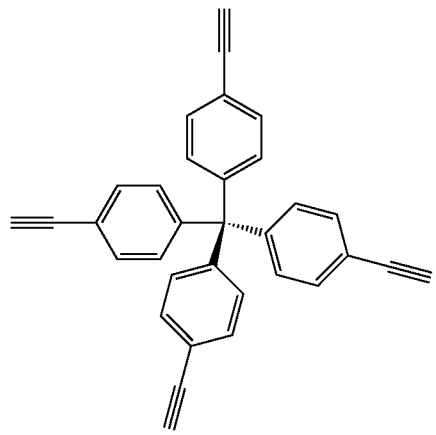
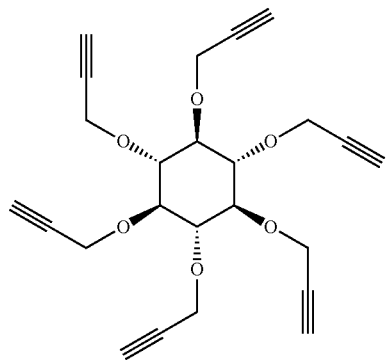 [SMILES: C#CCO[C@H]1[C@H](OCC#C)[C@@H](OCC#C)[C@H](OCC#C)[C@@H](OCC#C)[C@@H]1OCC#C]
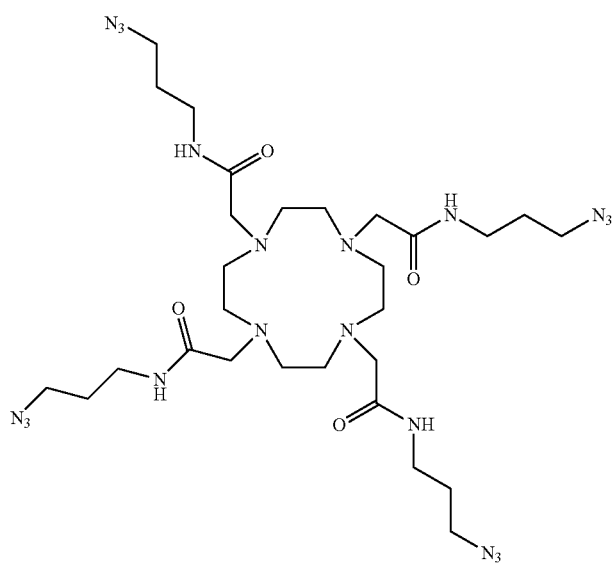 [SMILES: [N-]=[N+]=NCCCNC(=O)CN1CCN(CC(=O)NCCCN=[N+]=[N-])CCN(CC(=O)NCCCN=[N+]=[N-])CCN(CC(=O)NCCCN=[N+]=[N-])CC1]

Spacers

As described herein, in some embodiments, luminescent labels and/or reactants can be attached to a nucleic acid linker via a spacer. In some embodiments, the spacer attaches to an oligonucleotide strand of the nucleic acid linker at an attachment site. In some embodiments, the attachment site occurs at a terminal site on the oligonucleotide strand (e.g., at a 5' or 3' end). Examples of terminal attachment sites are provided in the instant application, e.g., as shown in FIGS. 3C, 3E, 4C, 6B, 6C, 8, 9, and 10 (terminal attachment of nucleotides), and in FIGS. 5B, 9, and 10 (terminal attachment of luminescent labels). In some embodiments, the attachment site occurs at an abasic site within the oligonucleotide strand (e.g., at a site that lacks but is adjacent to nucleotides). Examples of abasic attachment sites are provided in the instant application, e.g., as shown in FIGS. 3C, 3E, 6B, 6C, and 8 (abasic attachment of luminescent labels). In some embodiments, the attachment site occurs at a basic site on the oligonucleotide strand (e.g., attached to a nucleotide, such as the nucleobase, sugar, or phosphate of a nucleotide on the strand). Examples of basic attachment sites are provided in the instant application, e.g., as shown in FIGS. 4C and 8 (basic attachment of luminescent labels).

In some embodiments, a spacer comprises a plurality of thymidine nucleotides. In some embodiments, the spacer comprises a branched spacer, e.g., a branched thymidine spacer. In some embodiments, the branched spacer comprises a branched thymidine spacer. For example, in some embodiments, each nucleoside polyphosphate comprises a thymidine spacer of the formula Nu-T(T)$_n$T-R, where Nu represents a nucleoside polyphosphate, T represents a thymidine nucleotide, n is an integer with a value between 1 and 30, and R represents a point of convergence connecting one or more additional nucleoside polyphosphates. In some embodiments, the point of convergence is further attached directly to an oligonucleotide strand of the nucleic acid. In some embodiments, the point of convergence is further attached indirectly to the oligonucleotide strand, e.g., through further thymidine linkers and/or further points of convergence. An example of a branched thymidine spacer is shown in FIG. 5B, which depicts two nucleoside polyphosphates having thymidine spacers and a point of convergence that is further attached directly to an oligonucleotide strand.

In some embodiments, a spacer contains one or more points of divergence so that two or more (e.g., 2, 3, 4, 5, 6, 7, 8, 9, 10, or more) nucleoside polyphosphates are connected to each luminescent label, two or more (e.g., 2, 3, 4, 5, 6, 7, 8, 9, 10, or more) luminescent labels are connected to each nucleoside polyphosphate, or two or more (e.g., 2, 3, 4, 5, 6, 7, 8, 9, 10, or more) nucleoside polyphosphates are connected to two or more (e.g., 2, 3, 4, 5, 6, 7, 8, 9, 10, or more) luminescent labels.

In some embodiments, the spacer is attached at a terminal site on an oligonucleotide strand of a nucleic acid linker. In some embodiments, a luminescent label and/or a reactant is attached at either a 5' or 3' end of an oligonucleotide strand via the generic spacer shown below:

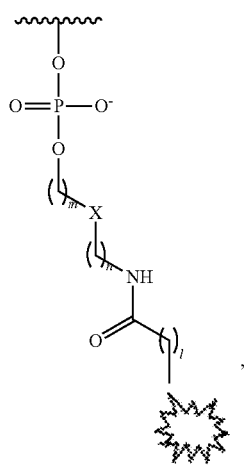

where ✦ is a luminescent label (or, in an alternative embodiment, a reactant); m>1; n>1; and m+n<10.

In some embodiments, the spacer is attached at an internal abasic site within an oligonucleotide strand of a nucleic acid linker. In some embodiments, a luminescent label and/or a reactant is attached at an internal abasic site on an oligonucleotide strand via the generic spacer shown below:

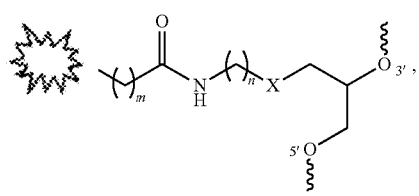

where ✦ is a luminescent label (or, in an alternative embodiment, a reactant); n>1; and X=CH$_2$ or O.

Examples of spacers for luminescent label attachment (e.g., via terminal, internal abasic, or basic attachment sites) are provided in Table 2 and shown below. Although spacer structures may be shown having luminescent labels, it should be appreciated that, in some embodiments, a reactant can be substituted such that any of the spacer structures provided herein can be used to attach a reactant (e.g., a nucleoside polyphosphate) to a nucleic acid linker.

In some embodiments, a luminescent label and/or a reactant is attached at an internal abasic site on an oligonucleotide strand via the glycolamine spacer shown below:

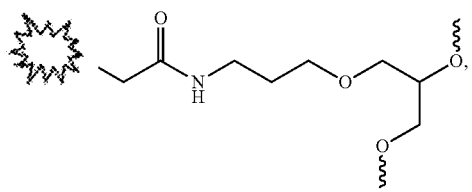

where ✦ is a luminescent label (or, in an alternative embodiment, a reactant).

In some embodiments, a luminescent label and/or a reactant is attached at an internal abasic site on an oligonucleotide strand via the serinolamine spacer shown below:

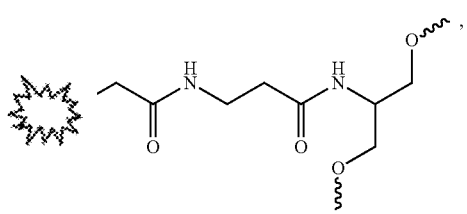

where ⚛ is a luminescent label (or, in an alternative embodiment, a reactant).

In some embodiments, a luminescent label and/or a reactant is attached at an internal basic site on an oligonucleotide strand via the C6-amino-T spacer shown below:

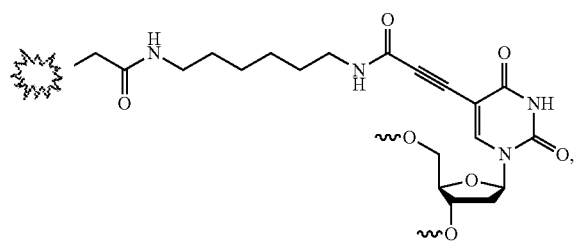

where ⚛ is a luminescent label (or, in an alternative embodiment, a reactant).

In some embodiments, a luminescent label and/or a reactant is attached at an internal basic site on an oligonucleotide strand via the C2-amino-T spacer shown below:

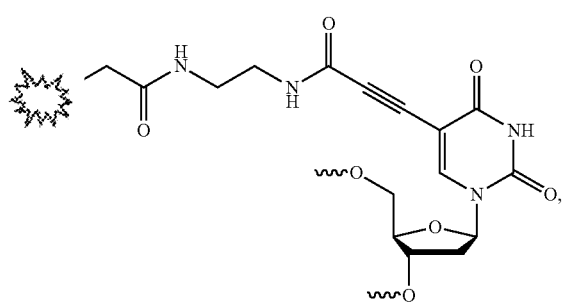

where ⚛ is a luminescent label (or, in an alternative embodiment, a reactant).

In some embodiments, a luminescent label and/or a reactant is attached at an internal basic site on an oligonucleotide strand via the C8-alkyne-dT spacer shown below:

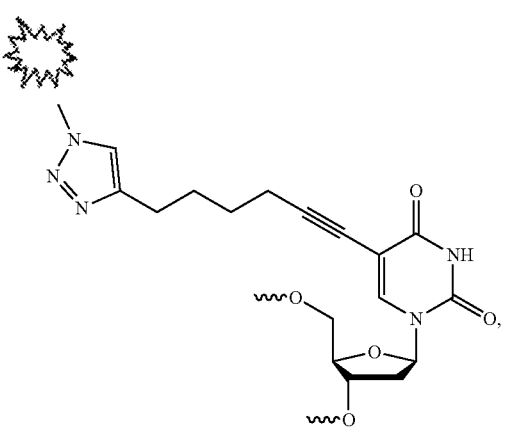

where ⚛ is a luminescent label (or, in an alternative embodiment, a reactant).

In some embodiments, one or more luminescent labels and/or one or more reactants (e.g., one or more nucleoside polyphosphates) can be attached to a nucleic acid linker using chemical coupling techniques known in the art. For example, in some embodiments, click chemistry techniques (e.g., copper-catalyzed, strain-promoted, copper-free click chemistry, etc.) can be used to attach the one or more luminescent labels and the one or more nucleoside polyphosphates to the nucleic acid. In some embodiments, a nucleoside polyphosphate is coupled to a nucleic acid linker via an azide-conjugated dN6P (e.g., dN6P-N$_3$), according to the generic structure shown below:

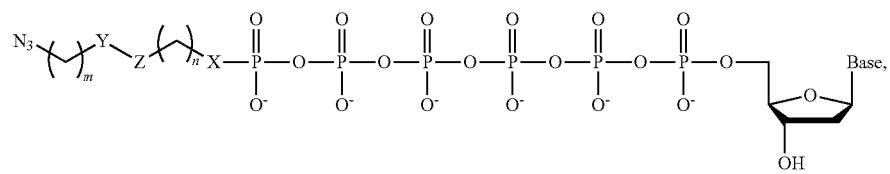

where Base is a nucleobase selected from adenine, cytosine, guanine, thymine, uracil, and derivatives thereof; —Y—Z—=-CH$_2$CH$_2$—, —CONH—, or —NHCO—; and X=NH or O. For example, in some embodiments, an azide-conjugated dN6P (e.g., dN6P-N$_3$) and/or an azide-conjugated luminescent label (e.g., dye-N$_3$) is attached to a nucleic acid linker in a copper-catalyzed reaction by contacting the azide of dN6P-N$_3$ or dye-N$_3$ with a terminal alkyne of an alkyne-conjugated nucleic acid linker under suitable reaction conditions to form a triazole linkage between the nucleic acid linker and dN6P or dye. In some embodiments, an azide-conjugated dN6P (e.g., dN6P-N$_3$) and/or an azide-conjugated luminescent label (e.g., dye-N$_3$) is attached to a nucleic acid linker in a copper-free reaction by contacting the azide of dN6P-N$_3$ or dye-N$_3$ with an internal alkyne of a cyclooctyne-conjugated nucleic acid linker under suitable reaction conditions to form a multicyclic linkage between the nucleic acid linker and dN6P or dye. Cyclooctyne modification of a nucleic acid linker can be accomplished using cyclooctyne reagents suitable for generating copper-free click chemistry moieties known in the art. For example, a cyclooctyne-modified nucleic acid linker is prepared by contacting a suitable cyclooctyne reagent (e.g., (1R,8S,9s)-Bicyclo[6.1.0]non yn-9-ylmethyl N-succinimidyl carbonate) with a terminal amine of a nucleic acid linker.

Accordingly, in some embodiments, a spacer includes a coupled group (e.g., BCN, tetrazine, tetrazole, and other products generated via the coupling of reactive moieties suitable for click reactions and similar coupling techniques). In some embodiments, the spacer is of the formula:

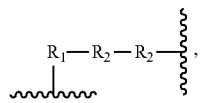

wherein R$_1$ is a first linking group and is attached to the attachment site on the first oligonucleotide strand; R$_2$ is a second linking group and comprises a coupled moiety formed in a coupling reaction performed to covalently join R$_1$ and R$_3$; and R$_3$ is a third linking group and is attached to the luminescent label.

In some embodiments, the spacer is of a formula selected from:

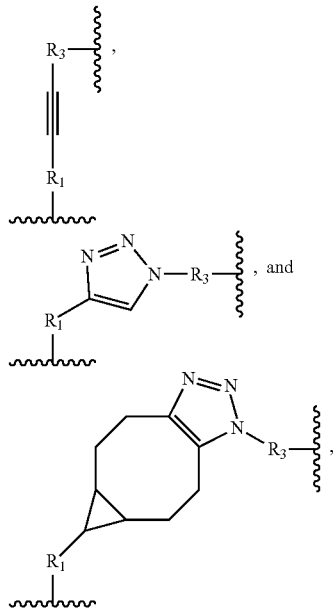

wherein R$_1$ and R$_3$ are each independently a bond or a linking group selected from the group consisting of substituted or unsubstituted alkylene; substituted or unsubstituted alkenylene; substituted or unsubstituted alkynylene; substituted or unsubstituted heteroalkylene; substituted or unsubstituted heteroalkenylene; substituted or unsubstituted heteroalkynylene; substituted or unsubstituted heterocyclylene; substituted or unsubstituted carbocyclylene; substituted or unsubstituted arylene; substituted or unsubstituted heteroarylene; and combinations thereof.

In some embodiments, examples of spacers generated using click chemistry are provided in Table 2, where ![] is a luminescent label (or, in an alternative embodiment, a reactant).

TABLE 2

Examples of clicked spacers

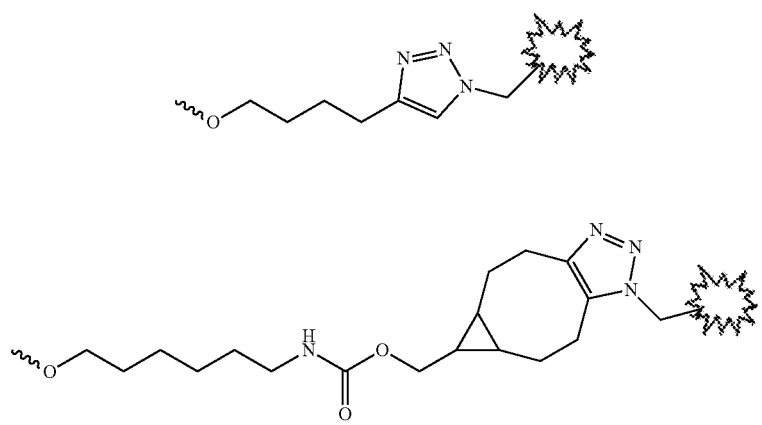

TABLE 2-continued

Examples of clicked spacers

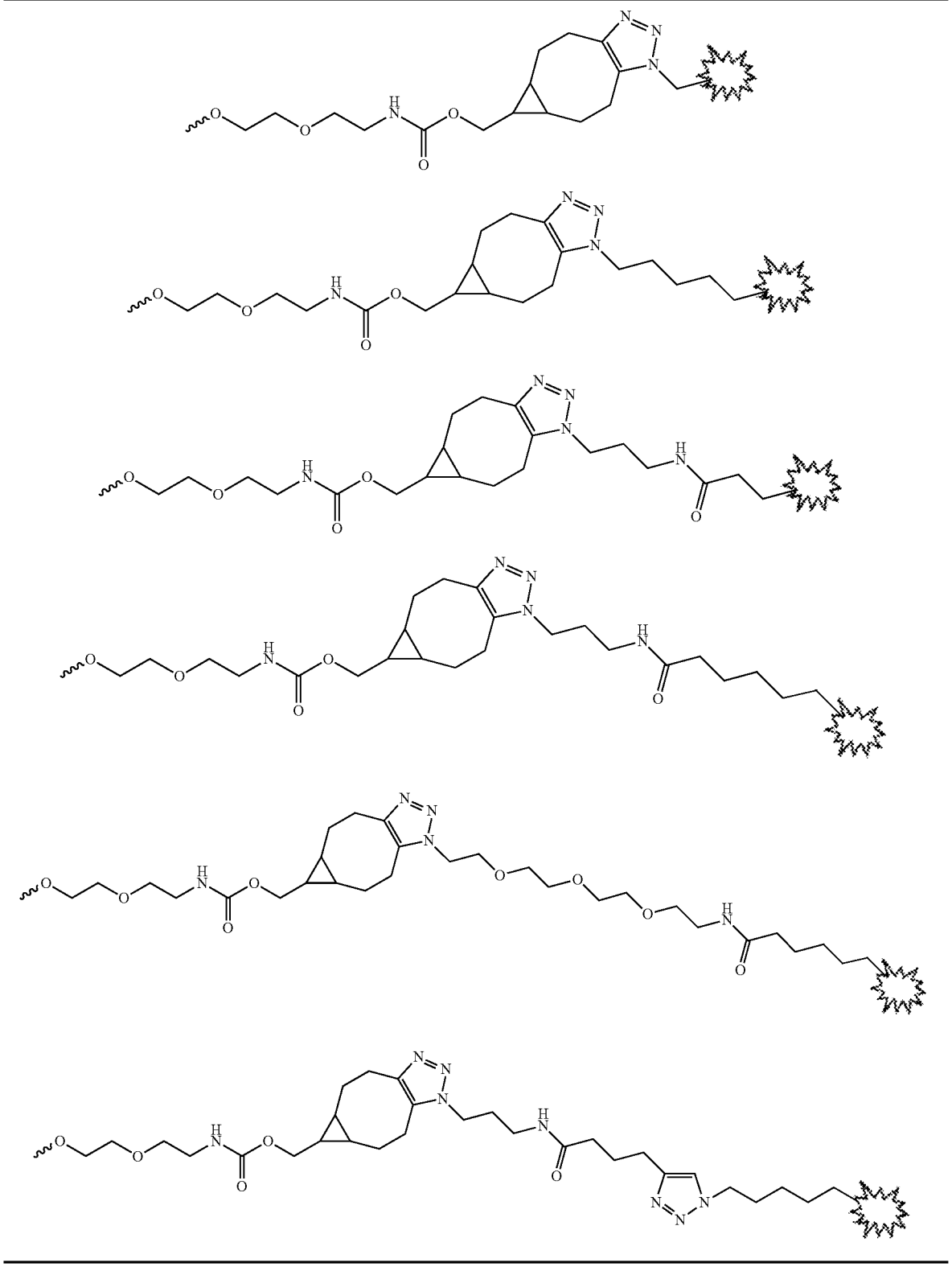

As used herein, a "nucleic acid linker" generally refers to a nucleic acid connecting one or more luminescent labels to one or more nucleoside polyphosphates. In some embodiments, a nucleic acid linker can generally refer to a construct having any number of oligonucleotide strands connected through covalent attachment or through base-pairing (e.g., hybridization). In some embodiments, a linker may be alternatively referred to as a "core" or a "base" construct to which different functional components (e.g., one or more luminescent labels, one or more nucleoside polyphosphates) can be attached. The term "construct" is, in some embodiments, used throughout in various contexts to generally refer to a linker, and may or may not encompass the various other components described herein (e.g., spacer, label, nucleoside polyphosphate, etc.).

In some embodiments, the nucleic acid linkers described herein are not attached to a particle of material (e.g., are not attached to a particle of metallic, magnetic, polymeric, or other material). In some embodiments, a nucleic acid linker is a linear molecule (e.g., a "rod-shaped" nucleic acid). In some embodiments, a nucleic acid linker is a circular molecule. In some embodiments, a nucleic acid linker is single-stranded (e.g., with or without stem-loop structures). In some embodiments, a nucleic acid linker is double-stranded (e.g., with or without stem loop structures). In some embodiments, the two strands of a double stranded nucleic acid linker are hybridized (due to complementary sequences) and not covalently attached. However, in some embodiments, one or more covalent bonds may be introduced (e.g., using one or more chemical linkers) to covalently attach two strands of a double stranded linker. In some embodiments, a nucleic acid linker may include one or more additional moieties as described herein. In some embodiments, a nucleic acid linker includes i) one or more additional moieties within or at the end(s) of the sugar phosphate backbone, ii) one or more modifications (e.g., one or more modified bases or sugars), or a combination of i) and ii). However, in some embodiments a nucleic acid linker does not include i), ii), or either of i) or ii).

It should be understood that, in the context of a nucleic acid linker, a "nucleotide" or "nucleoside polyphosphate" attached thereto refers to the one or more nucleotides (e.g., nucleoside polyphosphates) that are configured to be incorporated into a growing nucleic acid strand (e.g., during a sequencing reaction). In some embodiments, the one or more nucleotides comprise one or more nucleoside mono-phosphates or nucleoside polyphosphates. Examples of nucleoside polyphosphates include, in some embodiments, nucleoside di- or triphosphates, or nucleosides with more than three 5' phosphates, such as nucleoside hexaphosphates. Accordingly, in some embodiments, a "labeled nucleotide" refers to a nucleoside polyphosphate connected to one or more luminescent labels through a linker of the application, where the nucleoside polyphosphate acts as a substrate for a polymerase enzyme under nucleic acid synthesis reaction conditions. In some embodiments, the nucleoside polyphosphate comprises at least a diphosphate group or a triphosphate group which can be acted upon by a suitable polymerase enzyme in a phosphoryl transfer reaction (e.g., transfer of the a-phosphate of the nucleoside polyphosphate from its (3-phosphate to the 3' hydroxyl group of a growing nucleic acid strand).

In some embodiments, the one or more nucleoside phosphates (e.g., nucleoside polyphosphates) may be attached through a terminal phosphate to an oligonucleotide (e.g., a labeled or an unlabeled oligonucleotide strand) that forms part of a linker of the application, which can function as a protecting molecule that protects a polymerase from label-induced photodamage (e.g., as described elsewhere in this application). In some embodiments of any of the compositions or methods described in this application, a phosphate portion (e.g., a polyphosphate portion) of a nucleoside phosphate (e.g., of a nucleoside polyphosphate) includes one or more phosphates (e.g., 1, 2, 3, 4, 5, 6, 7, 8, 9, 10, or more phosphate groups) or variants thereof. For example, in some embodiments, a phosphate portion (e.g., a polyphosphate portion) of a nucleoside phosphate (e.g., of a nucleoside polyphosphate) can include a phosphate ester, a thioester, a phosphoramidate, an alkyl phosphonate linkage, other suitable linkage, or more than one such modifications, or a combination of two or more thereof. In some embodiments, the labeled and unlabeled strands of a nucleic acid linker are substantially complementary to one another (e.g., over the length of a dimerization domain wherein the strands within the dimerization domain can have, for example, at least 60%, at least 70%, at least 75%, at least 80%, at least 85%, at least 90%, at least 95%, at least 98%, at least 99%, or 100% complementary to one another).

A nucleoside polyphosphate can have n phosphate groups, where n is a number that is greater than or equal to 2, 3, 4, 5, 6, 7, 8, 9, or 10. Examples of nucleoside polyphosphates include nucleoside diphosphate and nucleoside triphosphate. A labeled nucleotide can be a terminal phosphate labeled nucleoside polyphosphate, such that a terminal phosphate of the nucleoside polyphosphate is attached to a linker (e.g., a nucleic acid linker) that comprises one or more luminescent labels, thereby forming a labeled nucleoside polyphosphate. Such label can be a luminescent (e.g., fluorescent or chemi-luminescent) label, a fluorogenic label, a colored label, a chromogenic label, a mass tag, an electrostatic label, or an electrochemical label. A label (or marker) can be coupled to a terminal phosphate through a linker, such as a spacer as described herein. The linker (e.g., spacer) can include, for example, at least one or a plurality of hydroxyl groups, sulfhydryl groups, amino groups or haloalkyl groups, which may be suitable for forming, for example, a phosphate ester, a thioester, a phosphoramidate or an alkyl phosphonate linkage at the terminal phosphate of a natural or modified nucleotide. A linker (e.g., a spacer) can be cleavable so as to separate a label from the terminal phosphate, such as with the aid of a polymerization enzyme. Examples of nucleotides and linkers (e.g., spacers) are provided in U.S. Pat. No. 7,041,812, which is entirely incorporated herein by reference.

A nucleotide (e.g., a nucleoside polyphosphate) can comprise any of an adenine (A), cytosine (C), guanine (G), thymine (T), and uracil (U), or variants thereof. A nucleotide (e.g., a nucleoside polyphosphate) can comprise a methyl-ated nucleobase. For example, a methylated nucleotide can be a nucleotide that comprises one or more methyl groups attached to the nucleobase (e.g., attached directly to a ring of the nucleobase, attached to a substituent of a ring of the nucleobase). Exemplary methylated nucleobases include 1-methylthymine, 1-methyluracil, 3-methyluracil, 3-methyl-cytosine, 5-methylcytosine, 1-methyladenine, 2-methylad-enine, 7-methyladenine, $N_6$-methyladenine, N6,N6-dimeth-yladenine, 1-methylguanine, 7-methylguanine, N2-methylguanine, and N2,N2-dimethylguanine.

The term "nucleic acid," as used herein, generally refers to a molecule comprising one or more nucleic acid subunits. A nucleic acid may include one or more subunits selected from adenine (A), cytosine (C), guanine (G), thymine (T), and uracil (U), or variants thereof. In some examples, a nucleic acid is deoxyribonucleic acid (DNA) or ribonucleic acid (RNA), or derivatives thereof. In some embodiments, the nucleic acid is a modified nucleic acid, including, without limitation, a locked nucleic acid (LNA), a peptide nucleic acid (PNA), a triazole-linked nucleic acid, a 2'-F-modified nucleic acid, and derivatives and analogs thereof.

A nucleic acid may be single-stranded or double stranded. In some embodiments, a nucleic acid generally refers to any polymer of nucleotides.

In some embodiments, the disclosure provides new compositions for identifying single molecules based on one or more luminescent properties of those molecules. In some embodiments, a molecule (e.g., a luminescently labeled nucleoside polyphosphate) is identified based on its brightness, luminescent lifetime, absorption spectra, emission spectra, luminescent quantum yield, luminescent intensity, or a combination of two or more thereof. Identifying may mean assigning the exact molecular identity of a molecule, or may mean distinguishing or differentiating the particular molecule from a set of possible molecules. In some embodiments, a plurality of single molecules can be distinguished from each other based on different brightnesses, luminescent lifetimes, absorption spectra, emission spectra, luminescent quantum yields, luminescent intensities, or combinations of two or more thereof. In some embodiments, a single molecule is identified (e.g., distinguished from other molecules) by exposing the molecule to a series of separate light pulses and evaluating the timing or other properties of each photon that is emitted from the molecule. In some embodiments, information for a plurality of photons emitted sequentially from a single molecule is aggregated and evaluated to identify the molecule. In some embodiments, a luminescent lifetime of a molecule is determined from a plurality of photons that are emitted sequentially from the molecule, and the luminescent lifetime can be used to identify the molecule. In some embodiments, a luminescent intensity of a molecule is determined from a plurality of photons that are emitted sequentially from the molecule, and the luminescent intensity can be used to identify the molecule. In some embodiments, a luminescent lifetime and luminescent intensity of a molecule is determined from a plurality of photons that are emitted sequentially from the molecule, and the luminescent lifetime and luminescent intensity can be used to identify the molecule.

Accordingly, in some aspects of the application, a reaction sample is exposed to a plurality of separate light pulses and a series of emitted photons are detected and analyzed. In some embodiments, the series of emitted photons provides information about a single molecule that is present and that does not change in the reaction sample over the time of the experiment. However, in some embodiments, the series of emitted photons provides information about a series of different molecules that are present at different times in the reaction sample (e.g., as a reaction or process progresses).

Luminescent Labels

As used herein, a "luminescent label" is a molecule that absorbs one or more photons and may subsequently emit one or more photons after one or more time durations. In some embodiments, the term may be used to generally refer to a non-reactant portion of a labeled reactant (e.g., a luminescent label can include a fluorophore and at least a portion of a spacer). In some embodiments, the term refers specifically to the molecule that absorbs and/or emits photons (e.g., the fluorophore). In some embodiments, the term is used interchangeably with "luminescent molecule" depending on context. In some embodiments, the luminescent label is a fluorophore (e.g., a "dye" or "fluorophore dye", as used herein interchangeably). In some embodiments, the luminescent label is a rhodamine-based molecule. In some embodiments, the luminescent label is a cyanine-based molecule. In some embodiments, the luminescent label is a BODIPY®-based molecule.

Typically, the luminescent label comprises an aromatic or heteroaromatic compound and can be a pyrene, anthracene, naphthalene, acridine, stilbene, indole, benzindole, oxazole, carbazole, thiazole, benzothiazole, phenanthridine, phenoxazine, porphyrin, quinoline, ethidium, benzamide, cyanine, carbocyanine, salicylate, anthranilate, coumarin, fluoroscein, rhodamine or other like compound. Examples of dyes include xanthene dyes, such as fluorescein or rhodamine dyes, including 5-carboxyfluorescein (FAM), 2'7'-dimethoxy-4'5'-dichloro-6-carboxyfluorescein (JOE), tetrachlorofluorescein (TET), 6-carboxyrhodamine (R6G), N,N,N',N'-tetramethyl-6-carboxyrhodamine (TAMRA™), 6-carboxy-X-rhodamine (ROX). Examples of dyes also include naphthylamine dyes that have an amino group in the alpha or beta position. For example, naphthylamino compounds include 1-dimethylaminonaphthyl-5-sulfonate, 1-anilino-8-naphthalene sulfonate and 2-p-toluidinyl-6-naphthalene sulfonate, 5-(2'-aminoethyl)aminonaphthalene-1-sulfonic acid (EDANS). Other examples of dyes include coumarins, such as 3-phenyl-7-isocyanatocoumarin; acridines, such as 9-isothiocyanatoacridine and acridine orange; N-(p-(2-benzoxazolyl)phenyl)maleimide; cyanines, such as indodicarbocyanine 3 (Cy®3), (2Z)-2-[(E)-3-[3-(5-carboxypentyl)-1,1-dimethyl-6,8-disulfobenzo[e]indol-3-ium-2-yl]prop-2-enylidene]-3-ethyl-1,1-dimethyl-8-(trioxidanylsulfanyl)benzo[e]indole-6-sulfonate (Cy®3.5), 2-[2-[(2,5-dioxopyrrolidin-1-yl)oxy]-2-oxoethyl}-16,16,18,18-tetramethyl-6,7,7a,8a,9,10,16,18-octahydrobenzo[2",3"]indolizino[8",7":5',6']pyrano[3',2':3,4]pyrido[1,2-a]indol-5-ium-14-sulfonate (Cy®3B), indodicarbocyanine 5 (Cy®5), indodicarbocyanine 5.5 (Cy®5.5), 3-(-carboxy-pentyl)-3'-ethyl-5,5'-dimethyloxacarbocyanine (CyA); 1H,5H,11H,15H-Xantheno[2,3,4-ij:5,6,7-i'j']diquinolizin- 18-ium, 9-[2 (or 4)-[[[6-(2,5-dioxo-1-pyrrolidinyl)oxy]-6-oxohexyl]amino]sulfonyl]-4(or 2)-sulfophenyl]-2,3,6,7,12,13,16,17-octahydro-inner salt (TR or Texas Red® (5-chlorosulfonyl-2-(3-oxa-23-aza-9-azoniaheptacyclo[17.7.1.1$^{5,9}$.0$^{2,17}$.0$^{4,}$ $_{15}$.0$^{23,27}$.0$^{13,28}$]octacosa-1(27),2(17),4,9(28),13,15,18-heptaen-16-yl)benzenesulfonate)); BODIPY® dyes; benzoxazoles; stilbenes; pyrenes; and the like.

In certain embodiments, the luminescent label is a dye selected from Table 3. The dyes listed in Table 3 are non-limiting, and the luminescent labels of the application may include dyes not listed in Table 3. In certain embodiments, the luminescent labels of one or more luminescently labeled nucleotides is selected from Table 3. In certain embodiments, the luminescent labels of four or more luminescently labeled nucleotides is selected from Table 3.

TABLE 3

| Examples of fluorophores Fluorophores | | |
|---|---|---|
| 5/6-Carboxyrhodamine 6G | Chromis 678C | DyLight ® 655-B1 |
| 5-Carboxyrhodamine 6G (9-[2-carboxy-4-[[(2,5-dioxo-1-pyrrolidinyl)oxy]carbonyl]phenyl]-3,6-bis(ethylamino)-2,7-dimethyl-xanthene) | Chromis 678Z | DyLight ® 655-B2 |

TABLE 3-continued

| Examples of fluorophores Fluorophores | | |
|---|---|---|
| 6-Carboxyrhodamine 6G (9-[5-carboxy-2-(ethoxycarbonyl)phenyl]-3,6-bis(ethylamino)-2,7-dimethylxanthenium chloride) | Chromis 770A | DyLight ® 655-B3 |
| 6-TAMRA ™ (6-carboxytetramethylrhodamine) | Chromis 770C | DyLight ® 655-B4 |
| Alexa Fluor ® 350 (7-amino-3-[2-(2,5-dioxopyrrolidin-1-yl)oxy-2-oxoethyl]-4-methyl-2-oxochromene-6-sulfonic acid) | Chromis 800A | DyLight ® 662Q |
| Alexa Fluor ® 405 (8-[2-[4-(2,5-dioxopyrrolidin-1-yl)oxycarbonylpiperidin-1-yl]-2-oxoethoxy]pyrene-1,3,6-trisulfonate) | Chromis 800C | DyLight ® 675-B1 |
| Alexa Fluor ® 430 ([9-[6-(2,5-dioxopyrrolidin-1-yl)oxy-6-oxohexyl]-8,8-dimethyl-2-oxo-4-(trifluoromethyl)pyrano[3,2-g]quinolin-6-yl]methanesulfonate) | Chromis 830A | DyLight ® 675-B2 |
| Alexa Fluor ® 480 (3-(3-amino-6-imino-4,5-disulfonatoxanthen-9-yl)-4-carboxybenzoate) | Chromis 830C | DyLight ® 675-B3 |
| Alexa Fluor ® 488 (3-amino-6-azaniumylidene-9-(2-carboxyphenyl)xanthene-4,5-disulfonate) | Cy ® 3 (indodicarbocyanine 3) | DyLight ® 675-B4 |
| Alexa Fluor ® 514 (9-azaniumylidene-6-[2-carboxy-5-(2,5-dioxopyrrolidin-1-yl)oxycarbonylphenyl]-2,2,4-trimethyl-12-sulfo-3,4-dihydro-1H-chromeno[3,2-g]quinoline-10-sulfonate) | Cy ® 3.5 ((2Z)-2-[(E)-3-[3-(5-carboxypentyl)-1,1-dimethyl-6,8-disulfobenzo[e]indol-3-ium-2-yl]prop-2-enylidene]-3-ethyl-1,1-dimethyl-8-(trioxidanylsulfanyl)benzo[e]indole-6-sulfonate) | DyLight ® 679-C5 |
| Alexa Fluor ® 532 (5-(4-{[(2,5-dioxopyrrolidin-1-yl)oxy]carbonyl}phenyl)-2,3,3,7,7,8-hexamethyl-2,3,7,8-tetrahydro-1H-pyrano[3,2-f:5,6-f']diindole-10,12-disulfonic acid) | Cy ® 3B (2-{2-[(2,5-dioxopyrrolidin-1-yl)oxy]-2-oxoethyl}-16,16,18,18-tetramethyl-6,7,7a,8a,9,10,16,18-octahydrobenzo[2'',3'']indolizino[8'',7'':5',6']pyrano[3',2':3,4]pyrido[1,2-a]indol-5-ium-14-sulfonate) | DyLight ® 680 |
| Alexa Fluor ® 546 (sodium 6-(2-carboxy-3,4,6-trichloro-5-{[2-({6-[(2,5-dioxopyrrolidin-1-yl)oxy]-6-oxohexyl}amino)-2-oxoethyl]thio}phenyl)-2,2,4,8,10,10-hexamethyl-3,4,5a,8,9,10,11,12a-octahydro-2H-pyrano[3,2-g:5,6-g']diquinolin-1-ium-12,14-disulfonate) | Cy ® 5 (indodicarbocyanine 5) | DyLight ® 683Q |
| Alexa Fluor ® 555 (4-(3-amino-6-imino-4,5-disulfoxanthen-9-yl)benzene-1,3-dicarboxylic acid) | Dyomics ®-350 | DyLight ® 690-B1 |
| Alexa Fluor ® 568 ([13-[2-carboxy-4-(2,5-dioxopyrrolidin-1-yl)oxycarbonylphenyl]-7,7,19,19-tetramethyl-17-(sulfomethyl)-2-oxa-20-aza-6-azoniapentacyclo[12.8.0.0$^{3,12}$.0$^{5,10}$.0$^{16,21}$]docosa-1(14),3,5,8,10,12,15,17,21-nonaen-9-yl]methanesulfonate) | Dyomics ®-350XL | DyLight ® 690-B2 |
| Alexa Fluor ® 594 ([13-[2-carboxy-4-(2,5-dioxopyrrolidin-1-yl)oxycarbonylphenyl]- | Dyomics ®-360XL | DyLight ® 696Q |

TABLE 3-continued

Examples of fluorophores
Fluorophores

| | | |
|---|---|---|
| 6,7,7,19,19,20-hexamethyl-17-(sulfomethyl)-2-oxa-20-aza-6-azoniapentacyclo[12.8.0.0$^{3,12}$.0$^{5,10}$.0$^{16,21}$]docosa-1(14),3,5,8,10,12,15,17,21-nonaen-9-yl]methanesulfonate) | | |
| Alexa Fluor ® 610-X (2,3,5-trichloro-4-[2-[[6-(2,5-dioxopyrrolidin-1-yl)oxy-6-oxohexyl]amino]-2-oxoethyl]sulfanyl-6-[6,7,7,19,19,20-hexamethyl-9,17-bis(sulfonatomethyl)-2-oxa-20-aza-6-azoniapentacyclo[12.8.0.0$^{3,12}$.0$^{5,10}$.0$^{16,21}$]docosa-1(14),3,5,8,10,12,15,17,21-nonaen-13-yl]benzoate;triethylazanium) | Dyomics ®-370XL | DyLight ® 700-B1 |
| Alexa Fluor ® 633 | Dyomics ®-375XL | DyLight ® 700-B1 |
| Alexa Fluor ® 647 (2-[5-[3,3-dimethyl-5-sulfo-1-(3-sulfopropyl)indol-1-ium-2-yl]penta-2,4-dienylidene]-3-methyl-3-[5-oxo-5-(6-phosphonooxyhexylamino)pentyl]-1-(3-sulfopropyl)indole-5-sulfonic acid) | Dyomics ®-380XL | DyLight ® 730-B1 |
| Alexa Fluor ® 660 | Dyomics ®-390XL | DyLight ® 730-B2 |
| Alexa Fluor ® 680 | Dyomics ®-405 | DyLight ® 730-B3 |
| Alexa Fluor ® 700 | Dyomics ®-415 | DyLight ® 730-B4 |
| Alexa Fluor ® 750 | Dyomics ®-430 | DyLight ® 747 |
| Alexa Fluor ® 790 | Dyomics ®-431 | DyLight ® 747-B1 |
| AMCA (aminomethylcoumarin acetate) | Dyomics ®-478 | DyLight ® 747-B2 |
| ATTO ™ 390 (4-(4,6,8,8-tetramethyl-2-oxo-6,7-dihydropyrano[3, 2-g]quinolin-9-yl)butanoic acid) | Dyomics ®-480XL | DyLight ® 747-B3 |
| ATTO ™ 425 (4-(3-ethoxycarbonyl-6,8,8-trimethyl-2-oxo-6,7-dihydropyrano[3,2-g]quinolin-9-yl)butanoic acid) | Dyomics ®-481XL | DyLight ® 747-B4 |
| ATTO ™ 465 (4-(3-amino-6-iminoacridin-10-yl)butanoic acid) | Dyomics ®-485XL | DyLight ® 755 |
| ATTO ™ 488 ([6-amino-9-[2-(3-carboxypropylcarbamoyl)phenyl]-4,5-disulfoxanthen-3-ylidene]azanium) | Dyomics ®-490 | DyLight ® 766Q |
| ATTO ™ 495 (4-[3,6-bis(dimethylamino)acridin-10-ium-10-yl]butanoic acid) | Dyomics ®-495 | DyLight ® 775-B2 |
| ATTO ™ 514 | Dyomics ®-505 | DyLight ® 775-B3 |
| ATTO ™ 520 ([9-(2-carboxyethyl)-6-(ethylamino)-2,7-dimethylxanthen-3-ylidene]-ethylazanium) | Dyomics ®-510XL | DyLight ® 775-B4 |
| ATTO ™ 532 | Dyomics ®-511XL | DyLight ® 780-B1 |
| ATTO ™ 542 | Dyomics ®-520XL | DyLight ® 780-B2 |
| ATTO ™ 550 | Dyomics ®-521XL | DyLight ® 780-B3 |
| ATTO ™ 565 (2-(6,20-diethyl-2-oxa-20-aza-6-azoniapentacyclo[12.8.0.0$^{3,12}$.0$^{5,10}$.0$^{16,21}$]docosa-1(14)3,5,10,12,15,21-heptaen-13-yl)terephthalic acid) | Dyomics ®-530 | DyLight ® 800 |

TABLE 3-continued

Examples of fluorophores
Fluorophores

| | | |
|---|---|---|
| ATTO ™ 590 (4-(6,20-diethyl-7,7,9,17,19,19-hexamethyl-2-oxa-20-aza-6-azoniapentacyclo[12.8.0.0$^{3,12}$.0$^{5,10}$.0$^{16,21}$]docosa-1(14)3,5,8,10,12,15,17,21-nonaen-13-yl)benzene-1,3-dicarboxylic acid) | Dyomics ®-547 | DyLight ® 830-B2 |
| ATTO ™ 610 (4-[9-(dimethylamino)-11,11-dimethyl-3,4-dihydro-2H-naphtho[2,3-g]quinolin-1-ium-1-yl]butanoic acid) | Dyomics ®-547P1 | eFluor ® 450 |
| ATTO ™ 620 (N-(10-(2-((3-carboxypropyl)(methyl)carbamoyl)phenyl)-7-(dimethylamino)-9,9-dimethylanthracen-2(9H)-ylidene)-N-methylmethanaminium) | Dyomics ®-548 | Eosin (2-(2,4,5,7-tetrabromo-3-oxido-6-oxoxanthen-9-yl)benzoate) |
| ATTO ™ 633 | Dyomics ®-549 | FITC (3',6'-dihydroxy-6-isothiocyanatospiro[2-benzofuran-3,9'-xanthene]-1-one) |
| ATTO ™ 647 (11-(3-carboxypropyl)-1-ethyl-2,2,8,10,10,13,13-heptamethyl-4-(sulfomethyl)-2,8,9,10,11,13-hexahydrobenzo[1,2-g:5,4-g']diquinolin-1-ium) | Dyomics ®-549P1 | Fluorescein (2-(6-hydroxy-3-oxo-3H-xanthen-9-yl)benzoic acid) |
| ATTO ™ 647N ((2-(7-Ethyl-3,3,8,8,10-pentamethyl-7-aza-21-azoniahexacyclo[15.7.1.0$^{2,15}$.0$^{4,13}$.0$^{6,11}$.0$^{21,25}$]pentacosa-1,4(13),5,11,14,16,18,21(25)-octaen-14-yl)-N-methyl-N-(4-oxopentyl)benzamide) | Dyomics ®-550 | HiLyte ™ Fluor 405 |
| ATTO ™ 655 ([6-(3-carboxypropyl)-20-ethyl-7,7-dimethyl-2-oxa-6,13-diaza-20-azoniapentacyclo[12.8.0.0$^{3,12}$.0$^{5,10}$.0$^{16,21}$]docosa-1(22),3(12),4,10,13,15,20-heptaen-9-yl]methanesulfonate) | Dyomics ®-554 | HiLyte ™ Fluor 488 |
| ATTO ™ 665 | Dyomics ®-555 | HiLyte ™ Fluor 532 |
| ATTO ™ 680 ([6-(3-carboxypropyl)-20-ethyl-7,7-dimethyl-2-oxa-6,13-diaza-20-azoniapentacyclo[12.8.0.0$^{3,12}$.0$^{5,10}$.0$^{16,21}$]docosa-1(22),3(12),4,8,10,13,15,20-octaen-9-yl]methanesulfonate) | Dyomics ®-556 | HiLyte ™ Fluor 555 |
| ATTO ™ 700 ((11-(3-carboxypropyl)-1-ethyl-2,2,4,10,10-pentamethyl-10,11-dihydro-2H-dipyrido[3,2-b:2',3'-i]phenoxazin-1-ium-8-yl)methanesulfonate) | Dyomics ®-560 | HiLyte ™ Fluor 594 |
| ATTO ™ 725 | Dyomics ®-590 | HiLyte™ Fluor 647 |
| ATTO ™ 740 | Dyomics ®-591 | HiLyte™ Fluor 680 |
| ATTO ™ Oxa12 | Dyomics ®-594 | HiLyte™ Fluor 750 |
| ATTO ™ Rho101 | Dyomics ®-601XL | IRDye ® 680LT (sodium 2-((1E,3Z,5Z)-3-(3-(4-carboxybutyl)phenyl)-5-(1,1-dimethyl-6,8-disulfonato-3-(3-sulfonatopropyl)-1,3-dihydro-2H-benzo[e]indol-2-ylidene)penta-1,3-dien-1-yl)-1,1-dimethyl-3-(3-sulfonatopropyl)-1H-benzo[e]indol-3-ium-6,8-disulfonate) |

TABLE 3-continued

Examples of fluorophores
Fluorophores

| | | |
|---|---|---|
| ATTO ™ Rho11 (6-(2-((3-carboxypropyl)(methyl)carbamoyl)phenyl)-1,11-diethyl-3,4,8,9,10,11-hexahydro-2H-pyrano[3,2-g:5,6-g']diquinolin-1-ium) | Dyomics ®-605 | IRDye ® 750 (tetrasodium mono(2-((E)-2-((E)-3'-(4-carboxybutyl)-6-(2-((E)-3,3-dimethyl-5-sulfonato-1-(4-sulfonatobutyl)indolin-2-ylidene)ethylidene)-3,4,5,6-tetrahydro-[1,1'-biphenyl]-2-yl)vinyl)-3,3-dimethyl-1-(4-sulfonatobutyl)-3H-indol-1-ium-5-sulfonate) |
| ATTO ™ Rho12 (6-(2-((3-carboxypropyl)(methyl)carbamoyl)phenyl)-1,11-diethyl-2,2,4,8,10,10-hexamethyl-3,4,8,9,10,11-hexahydro-2H-pyrano[3,2-g:5,6-g']diquinolin-1-ium) | Dyomics ®-610 | IRDye ® 800CW (tetrasodium mono(2-((E)-2-((E)-3-(2-((E)-1-(5-carboxypentyl)-3,3-dimethyl-5-sulfonatoindolin-2-ylidene)ethylidene)-2-(4-sulfonatophenoxy)cyclohex-1-en-1-yl)vinyl)-3,3-dimethyl-1-(4-sulfonatobutyl)-3H-indol-1-ium-5-sulfonate) |
| ATTO ™ Rho13 (6-(2-((3-carboxypropyl)(methyl)carbamoyl)phenyl)-1,11-diethyl-2,2,4,8,10,10-hexamethyl-10,11-dihydro-2H-pyrano[3,2-g:5,6-g']diquinolin-1-ium) | Dyomics ®-615 | JOE |
| ATTO ™ Rho14 (6-(2-((3-carboxypropyl)(methyl)carbamoyl)-3,4,5,6-tetrachlorophenyl)-1,11-diethyl-2,2,4,8,10,10-hexamethyl-10,11-dihydro-2H-pyrano[3,2-g:5,6-g']diquinolin-1-ium) | Dyomics ®-630 | LightCycler ® 640R |
| ATTO ™ Rho3B (N-(13-(2-((3-carboxypropyl)(methyl)carbamoyl)phenyl)-9-(diethylamino)-8,9-dihydro-3H-dibenzo[b,i]xanthen-3-ylidene)-N-ethylethanaminium | Dyomics ®-631 | LightCycler ® Red 610 |
| ATTO ™ Rho6G (N-(9-(2-((3-carboxypropyl)(methyl)carbamoyl)phenyl)-6-(ethylamino)-2,7-dimethyl-3H-xanthen-3-ylidene)-N-methylmethanaminium) | Dyomics ®-632 | LightCycler ® Red 640 |
| ATTO ™ Thio12 ([9-[2-[3-carboxypropyl(methyl)carbamoyl]phenyl]-6-(dimethylamino)thioxanthen-3-ylidene]-dimethylazanium) | Dyomics ®-633 | LightCycler ® Red 670 |
| BD Horizon ™ V450 | Dyomics ®-634 | LightCycler ® Red 705 |
| BODIPY ® 493/503 (3-(5,5-difluoro-1,3,7,9-tetramethyl-3H,5H-5λ4-dipyrrolo[1,2-c:2',1'-f][1,3,2]diazaborinin-10-yl)propanoic acid) | Dyomics ®-635 | Lissamine Rhodamine B (2-[3-(diethylamino)-6-diethylazaniumylidenexanthen-9-yl]-5-sulfobenzenesulfonate) |
| BODIPY ® 530/550 (3-(5,5-difluoro-1,3-diphenyl-3H,5H-5λ4-dipyrrolo[1,2-c:2',1'-f][1,3,2]diazaborinin-7-yl)propanoic acid) | Dyomics ®-636 | Napthofluorescein (7',19'-dihydroxyspiro[2-benzofuran-3,13'-2-oxapentacyclo[12.8.0.0$^{3,12}$.0$^{4,9}$.0$^{17,22}$]docosa-1(14),3(12),4(9),5,7,10,15,17(2 2),18,20-decaene]-1-one) |
| BODIPY ® 558/568 (3-(5,5-difluoro-3-(thiophen-2-yl)-3H,5H-5λ4-dipyrrolo[1,2-c:2',1'-f][1,3,2]diazaborinin-7-yl)propanoic acid) | Dyomics ®-647 | Oregon Green ® 488 (4-(2,7-difluoro-3-hydroxy-6-oxoxanthen-9-yl)benzene-1,3-dicarboxylic acid) |
| BODIPY ® 564/570 ((E)-3-(5,5-difluoro-3-styryl-3H,5H-5λ4-dipyrrolo[1,2-c:2',1'-f][1,3,2]diazaborinin-7-yl)propanoic acid) | Dyomics ®-647P1 | Oregon Green ® 514 |

TABLE 3-continued

| Examples of fluorophores | | |
|---|---|---|
| Fluorophores | | |
| BODIPY ® 576/589 (3-(5,5-difluoro-3-(1H-pyrrol-2-yl)-3H,5H-5λ4-dipyrrolo[1,2-c:2',1'-f][1,3,2]diazaborinin-7-yl)propanoic acid) | Dyomics ®-648 | Pacific Blue ™ |
| BODIPY ® 581/591 (3-(5,5-difluoro-3-((1E,3E)-4-phenylbuta-1,3-dien-1-yl)-3H,5H-5λ4-dipyrrolo[1,2-c:2',1'-f][1,3,2]diazaborinin-7-yl)propanoic acid) | Dyomics ®-648P1 | Pacific Green ™ |
| BODIPY ® 630/650 ((E)-6-(2-(4-(2-(5,5-difluoro-3-(thiophen-2-yl)-3H,5H-5λ4-dipyrrolo[1,2-c:2',1'-f][1,3,2]diazaborinin-7-yl)vinyl)phenoxy)acetamido)hexanoic acid) | Dyomics ®-649 | Pacific Orange ™ |
| BODIPY ® 650/665 ((E)-6-(2-(4-(2-(5,5-difluoro-3-(1H-pyrrol-2-yl)-3H,5H-5λ4-dipyrrolo[1,2-c:2',1'-f][1,3,2]diazaborinin-7-yl)vinyl)phenoxy)acetamido)hexanoic acid) | Dyomics ®-649P1 | PET |
| BODIPY ® FL (3-(5,5-difluoro-1,3-dimethyl-3H,5H-54-dipyrrolo[1,2-c:2',1'-f][1,3,2]diazaborinin-7-yl)propanoic acid) | Dyomics ®-650 | PF350 |
| BODIPY ® FL-X (6-(3-(5,5-difluoro-1,3-dimethyl-3H,5H-5λ4-dipyrrolo[1,2-c:2',1'-f][1,3,2]diazaborinin-7-yl)propanamido)hexanoic acid) | Dyomics ®-651 | PF405 |
| BODIPY ® R6G (3-(5,5-difluoro-3-phenyl-3H,5H-5λ4-dipyrrolo[1,2-c:2',1'-f][1,3,2]diazaborinin-7-yl)propanoic acid) | Dyomics ®-652 | PF415 |
| BODIPY ® TMR (6-(3-(5,5-difluoro-3-(4-methoxyphenyl)-7,9-dimethyl-3H,5H-5λ4-dipyrrolo[1,2-c:2',1'-f][1,3,2]diazaborinin-8-yl)propanamido)hexanoic acid) | Dyomics ®-654 | PF488 |
| BODIPY ® TR (7-(4-(2-((5-carboxypentyl)amino)-2-oxoethoxy)phenyl)-5,5-difluoro-3-(thiophen-2-yl)-5H-5λ4-dipyrrolo[1,2-c:2',1'-f][1,3,2]diazaborinin-4-ium) | Dyomics ®-675 | PF505 |
| C5.5 (2,5-dioxopyrrolidin-1-yl 6-(1,1-dimethyl-2-((1E,3E,5E)-5-(1,1,3-trimethyl-1,3-dihydro-2H-benzo[e]indol-2-ylidene)penta-1,3-dien-1-yl)-1H-3λ4-benzo[e]indol-3-yl)hexanoate) | Dyomics ®-676 | PF532 |
| C7 (2,5-dioxopyrrolidin-1-yl 6-(3,3-dimethyl-2-((E)-2-((E)-3-(2-((E)-1,3,3-trimethylindolin-2-ylidene)ethylidene)cyclohex-1-en-1-yl)vinyl)-3H-1λ4-indol-1-yl)hexanoate) | Dyomics ®-677 | PF546 |
| CAL Fluor ® Gold 540 (4,5-dichloro-2-(2,7-dichloro-6-hydroxy-3-oxo-3H-xanthen-9-yl)benzoic acid) | Dyomics ®-678 | PF555P |
| CAL Fluor ® Green 510 (2-(6-hydroxy-3-oxo-3H-xanthen-9-yl)benzoic acid) | Dyomics ®-679P1 | PF568 |
| CAL Fluor ® Orange 560 ((E)-N-(9-(2-carboxyphenyl)-6-(ethylamino)-2,7-dimethyl-3H-xanthen-3-ylidene)ethanaminium) | Dyomics ®-680 | PF594 |

TABLE 3-continued

| Examples of fluorophores Fluorophores | | |
|---|---|---|
| CAL Fluor ® Red 590 (N-(6-(diethylamino)-9-(2-(1-(methyl(propyl)amino)vinyl)phenyl)-3H-xanthen-3-ylidene)-N-ethylethanaminium) | Dyomics ®-681 | PF610 |
| CAL Fluor ® Red 610 | Dyomics ®-682 | PF633P |
| CAL Fluor ® Red 615 | Dyomics ®-700 | PF647P |
| CAL Fluor ® Red 635 (6-(2-carboxy-4,5-dimethylphenyl)-1,11-diethyl-2,2,4,8,10,10-hexamethyl-10,11-dihydro-2H-pyrano[3,2-g:5,6-g']diquinolin-1-ium) | Dyomics ®-701 | Quasar ® 570 (2-((1E,3E)-3-(3-(5-carboxypentyl)-1,1-dimethyl-1,3-dihydro-2H-benzo[e]indol-2-ylidene)prop-1-en-1-yl)-3-ethyl-1,1-dimethyl-1H-benzo[e]indol-3-ium) |
| Cascade ® Blue (8-hydroxy-1,8-dihydropyrene-1,3,6-trisulfonate) | Dyomics ®-703 | Quasar ® 670 (2-((1E,3E)-5-((E)-1-(5-carboxypentyl)-3,3-dimethylindolin-2-ylidene)penta-1,3-dien-1-yl)-1-ethyl-3,3-dimethyl-3H-indol-1-ium) |
| CF ™ 350 | Dyomics ®-704 | Quasar ® 705 (2-((1E,3E,5E)-5-(3-(5-carboxypentyl)-1,1-dimethyl-1,3-dihydro-2H-benzo[e]indol-2-ylidene)penta-1,3-dien-1-yl)-3-ethyl-1,1-dimethyl-1H-benzo[e]indol-3-ium) |
| CF ™ 405M | Dyomics ®-730 | Rhoadmine 123 ([6-amino-9-(2-methoxycarbonylphenyl)xanthen-3-ylidene]azanium) |
| CF ™ 405S | Dyomics ®-731 | Rhodamine 6G ([9-(2-ethoxycarbonylphenyl)-6-(ethylamino)-2,7-dimethylxanthen-3-ylidene]-ethylazanium) |
| CF ™ 488A | Dyomics ®-732 | Rhodamine B ([9-(2-carboxyphenyl)-6-(diethylamino)xanthen-3-ylidene]-diethylazanium) |
| CF ™ 514 | Dyomics ®-734 | Rhodamine Green ([6-amino-9-(2,5-dicarboxyphenyl)xanthen-3-ylidene]azanium) |
| CF ™ 532 | Dyomics ®-749 | Rhodamine Green-X (2-(6-amino-3-(l4-azaneylidene)-3H-xanthen-9-yl)benzoic acid) |
| CF ™ 543 | Dyomics ®-749P1 | Rhodamine Red (4-(3-((2I5-butan-2-yl)imino)-6-(diethylamino)-3H-xanthen-9-yl)benzene-1,3-disulfonate) |
| CF ™ 546 | Dyomics ®-750 | ROX |
| CF ™ 555 | Dyomics ®-751 | ROX |
| CF ™ 568 | Dyomics ®-752 | Seta ™ 375 |
| CF ™ 594 | Dyomics ®-754 | Seta ™ 470 |
| CF ™ 620R | Dyomics ®-776 | Seta ™ 555 |
| CF ™ 633 | Dyomics ®-777 | Seta ™ 632 |
| CF ™ 633-V1 | Dyomics ®-778 | Seta ™ 633 |
| CF ™ 640R | Dyomics ®-780 | Seta ™ 650 |
| CF ™ 640R-Vl | Dyomics ®-781 | Seta ™ 660 |
| CF ™ 640R-V2 | Dyomics ®-782 | Seta ™ 670 |
| CF ™ 660C | Dyomics ®-800 | Seta ™ 680 |
| CF ™ 660R | Dyomics ®-831 | Seta ™ 700 |
| CF ™ 680 | DyLight ® 350 | Seta ™ 750 |
| CF ™ 680R | DyLight ® 405 | Seta ™ 780 |
| CF ™ 680R-V1 | DyLight ® 415-Co1 | Seta ™ APC-780 |
| CF ™ 750 | DyLight ® 425Q | Seta ™ PerCP-680 |
| CF ™ 770 | DyLight ® 485-LS | Seta ™ R-PE-670 |
| CF ™ 790 | DyLight ® 488 | Seta ™ 646 |
| Chromeo ™ 642 | DyLight ® 504Q | Seta ™ u 380 |
| Chromis 425N | DyLight ® 510-LS | Seta ™ u 425 |
| Chromis 500N | DyLight ® 515-LS | Seta ™ u 647 |
| Chromis 515N | DyLight ® 521-LS | Seta ™ u 405 |
| Chromis 530N | DyLight ® 530-R2 | Sulforhodamine 101 (2-(3-oxa-23-aza-9-azoniaheptacyclo[17.7.1.1$^{5,9}$.0$^{2,17}$.0$^{4,15}$.0$^{23,27}$.0$^{23,28}$]octacosa-1(27),2(17),4,9(28),13,15,18-heptaen-16-yl)-5-sulfobenzenesulfonate) |

TABLE 3-continued

Examples of fluorophores
Fluorophores

| | | |
|---|---|---|
| Chromis 550A | DyLight ® 543Q | TAMRA ™ (6-carboxytetramethylrhodamine) |
| Chromis 550C | DyLight ® 550 | TET |
| Chromis 550Z | DyLight ® 554-R0 | Texas Red ® (5-chlorosulfonyl-2-(3-oxa-23-aza-9-azoniaheptacyclo[17.7.1.1$^{5,9}$.0$^{2,17}$.0$^{4,15}$.0$^{23,27}$.0$^{13,28}$]octacosa-1(27),2(17),4,9(28),13,15,18-heptaen-16-yl)benzenesulfonate) |
| Chromis 560N | DyLight ® 554-R1 | TMR (5-carboxy-2-(6-(dimethylamino)-3-(dimethyliminio)-2,3-dihydro-1H-xanthen-9-yl)benzoate) |
| Chromis 570N | DyLight ® 590-R2 | TRITC (2-(6-(dimethylamino)-3-(dimethyliminio)-2,3-dihydro-1H-xanthen-9-yl)-4-thiocyanatobenzoate) |
| Chromis 577N | DyLight ® 594 | Yakima Yellow ™ (2-(7-(2-carboxylatoethyl)-2,5-dichloro-6-hydroxy-4-methyl-3-oxo-3H-xanthen-9-yl)-4,5-dichlorobenzoate) |
| Chromis 600N | DyLight ® 610-B1 | Zenon ® |
| Chromis 630N | DyLight ® 615-B2 | Zy3 (1-(5-carboxypentyl)-2-((E)-3-((E)-1-ethyl-3,3-dimethyl-5-sulfoindolin-2-ylidene)prop-1-en-1-yl)-3,3-dimethyl-3H-indol-1-ium-5-sulfonate) |
| Chromis 645A | DyLight ® 633 | Zy5 (1-(5-carboxypentyl)-2-((1E,3E)-5-((E)-1-ethyl-3,3-dimethyl-5-sulfoindolin-2-ylidene)penta-1,3-dien-1-yl)-3,3-dimethyl-3H-indol-1-ium-5-sulfonate) |
| Chromis 645C | DyLight ® 633-B1 | Zy5.5 (3-(5-carboxypentyl)-2-((1E,3E,5E)-5-(3-ethyl-1,1-dimethyl-6,8-disulfo-1,3-dihydro-2H-benzo[e]indol-2-ylidene)penta-1,3-dien-1-yl)-1,1-dimethyl-8-sulfo-1H-benzo[e]indol-3-ium-6-sulfonate) |
| Chromis 645Z | DyLight ® 633-B2 | Zy7 (1-(5-carboxypentyl)-2-((1E,3E,5E)-7-((E)-1-ethyl-3,3-dimethylindolin-2-ylidene)hepta-1,3,5-trien-1-yl)-3,3-dimethyl-3H-indol-1-ium) |
| Chromis 678A | DyLight ® 650 | Abberior ® Star 635 |
| Square 635 | Square 650 | Square 660 |
| Square 672 | Square 680 | Abberior ® Star 440SXP |
| Abberior ® Star470SXP | Abberior ® Star 488 | Abberior ® Star 512 |
| Abberior ® Star 520SXP | Abberior ® Star 580 | Abberior ® Star 600 |
| Abberior ® Star 635 | Abberior ® Star 635P | Abberior ® Star RED |

Dyes may also be classified based on the wavelength of maximum absorbance or emitted luminescence. Table 4 provides exemplary fluorophores grouped into columns according to approximate wavelength of maximum absorbance. The dyes listed in Table 4 are non-limiting, and the luminescent labels of the application may include dyes not listed in Table 4. The exact maximum absorbance or emission wavelength may not correspond to the indicated spectral ranges. In certain, embodiments, the luminescent labels of one or more luminescently labeled nucleotides is selected from the "Red" group listed in Table 4. In certain embodiments, the luminescent labels of one or more luminescently labeled nucleotides is selected from the "Green" group listed in Table 4. In certain embodiments, the luminescent labels of one or more luminescently labeled nucleotides is selected from the "Yellow/Orange" group listed in Table 4. In certain embodiments, the luminescent labels of four nucleotides are selected such that all are selected from one of the "Red", "Yellow/Orange", or "Green" group listed in Table 4. In certain embodiments, the luminescent labels of four nucleotides are selected such that three are selected from a first group of the "Red", "Yellow/Orange", and "Green" groups listed in Table 4, and the fourth is selected from a second group of the "Red", "Yellow/Orange", and "Green" groups listed in Table 4. In certain embodiments, the luminescent labels of four nucleotides are selected such that two are selected from a first of the "Red", "Yellow/Orange", and "Green" group listed in Table 4, and the third and fourth are selected from a second group of the "Red", "Yellow/Orange", and "Green" groups listed in Table 4. In certain embodiments, the luminescent labels of four nucleotides are selected such that two are selected from a first of the "Red", "Yellow/Orange", and "Green" groups listed in Table 4, and a third is selected from a second group of the "Red", "Yellow/Orange", and "Green" groups listed in Table 4, and a fourth is selected from a third group of the "Red", "Yellow/Orange", and "Green" groups listed in Table 4.

TABLE 4

| Examples of fluorophores by spectral range | | |
|---|---|---|
| "Green" 520-570 nm | "Yellow/Orange" 570-620 nm | "Red" 620-670 nm |
| 5/6-Carboxyrhodamine 6G | Alexa Fluor ® 594 ([13-[2-carboxy-4-(2,5-dioxopyrrolidin-1-yl)oxycarbonylphenyl]-6,7,7,19,19,20-hexamethyl-17-(sulfomethyl)-2-oxa-20-aza-6-azoniapentacyclo[12.8.0.0$^{3,12}$.0$^{5,10}$.0$^{16,21}$]docosa-1(14),3,5,8,10,12,15,17,21-nonaen-9-yl]methanesulfonate) | Alexa Fluor ® 633 |
| 6-TAMRA ™ (6-carboxytetramethylrhodamine) | Alexa Fluor ® 610-X (2,3,5-trichloro-4-[2-[[6-(2,5-dioxopyrrolidin-1-yl)oxy-6-oxohexyl]amino]-2-oxoethyl]sulfanyl-6-[6,7,7,19,19,20-hexamethyl-9,17-bis(sulfonatomethyl)-2-oxa-20-aza-6-azoniapentacyclo[12.8.0.0$^{3,12}$.0$^{5,10}$.0$^{16,21}$]docosa-1(14),3,5,8,10,12,15,17,21-nonaen-13-yl]benzoate;triethylazanium) | Alexa Fluor ® 647 (2-[5-[3,3-dimethyl-5-sulfo-1-(3-sulfopropyl)indol-1-ium-2-yl]penta-2,4-dienylidene]-3-methyl-3-[5-oxo-5-(6-phosphonooxyhexylamino)pentyl]-1-(3-sulfopropyl)indole-5-sulfonic acid) |
| Alexa Fluor ® 532 (5-(4-{[(2,5-dioxopyrrolidin-1-yl)oxy]carbonyl}phenyl)-2,3,3,7,7,8-hexamethyl-2,3,7,8-tetrahydro-1H-pyrano[3,2-f:5,6-f']diindole-10,12-disulfonic acid) | ATTO ™ 590 (4-(6,20-diethyl-7,7,9,17,19,19-hexamethyl-2-oxa-20-aza-6-azoniapentacyclo[12.8.0.0$^{3,12}$.0$^{5,10}$.0$^{16,21}$]docosa-1(14),3,5,8,10,12,15,17,21-nonaen-13-yl)benzene-1,3-dicarboxylic acid) | Alexa Fluor ® 660 |
| Alexa Fluor ® 546 (sodium 6-(2-carboxy-3,4,6-trichloro-5-{[2-({6-[(2,5-dioxopyrrolidin-1-yl)oxy]-6-oxohexyl}amino)-2-oxoethyl]thio}phenyl)-2,2,4,8,10,10-hexamethyl-3,4,5a,8,9,10,11,12a-octahydro-2H-pyrano[3,2-g:5,6-g']diquinolin-1-ium-12,14-disulfonate) | ATTO ™ 610 (4-[9-(dimethylamino)-11,11-dimethyl-3,4-dihydro-2H-naphtho[2,3-g]quinolin-1-ium-1-yl]butanoic acid) | ATTO ™ 633 |
| Alexa Fluor ® 555 (4-(3-amino-6-imino-4,5-disulfoxanthen-9-yl)benzene-1,3-dicarboxylic acid) | ATTO ™ 620 (N-(10-(2-((3-carboxypropyl)(methyl)carbamoyl)phenyl)-7-(dimethylamino)-9,9-dimethylanthracen-2(9H)-ylidene)-N-methylmethanaminium) | ATTO ™ 647 (11-(3-carboxypropyl)-1-ethyl-2,2,8,10,10,13,13-heptamethyl-4-(sulfomethyl)-2,8,9,10,11,13-hexahydrobenzo[1,2-g:5,4-g']diquinolin-1-ium) |
| Alexa Fluor ® 568 ([13-[2-carboxy-4-(2,5-dioxopyrrolidin-1-yl)oxycarbonylphenyl]-7,7,19,19-tetramethyl-17-(sulfomethyl)-2-oxa-20-aza-6-azoniapentacyclo[12.8.0.03,12.05,10.016,21]docosa-1(14),3,5,8,10,12,15,17,21-nonaen-9-yl]methanesulfonate) | BODIPY ® 576/589 3-(5,5-difluoro-3-(1H-pyrrol-2-yl)-3H,5H-5λ4-dipyrrolo[1,2-c:2',1'-f][1,3,2]diazaborinin-7-yl)propanoic acid) | ATTO ™ 647N ((2-(7-Ethyl-3,3,8,8,10-pentamethyl-7-aza-21-azoniahexacyclo[15.7.1.0$^{2,15}$.0$^{4,13}$.0$^{6,11}$.0$^{21,25}$]pentacosa-1,4(13),5,11,14,16,18,21(25)-octaen-14-yl)-N-methyl-N-(4-oxopentyl)benzamide) |
| ATTO ™ 520 ([9-(2-carboxyethyl)-6-(ethylamino)-2,7-dimethylxanthen-3-ylidene]-ethylazanium) | BODIPY ® 581/591 (3-(5,5-difluoro-3-((1E,3E)-4-phenylbuta-1,3-dien-1-yl)-3H,5H-5λ4-dipyrrolo[1,2-c:2',1'-f][1,3,2]diazaborinin-7-yl)propanoic acid) | ATTO ™ 655 ([6-(3-carboxypropyl)-20-ethyl-7,7-dimethyl-2-oxa-6,13-diaza-20-azoniapentacyclo[12.8.0.0$^{3,12}$.0$^{5,10}$.0$^{16,21}$]docosa-1(22),3(12),4,10,13,15,20-heptaen-9-yl]methanesulfonate |

TABLE 4-continued

Examples of fluorophores by spectral range

| "Green" 520-570 nm | "Yellow/Orange" 570-620 nm | "Red" 620-670 nm |
|---|---|---|
| ATTO ™ 532 | CF ™ 594 | ATTO ™ 665 |
| ATTO ™ 542 | CF ™ 620R | ATTO ™ 680 ([6-(3-carboxypropyl)-20-ethyl-7,7-dimethyl-2-oxa-6,13-diaza-20-azoniapentacyclo[12.8.0.0$^{3,12}$.0$^{5,10}$.0$^{16,21}$]docosa-1(22),3(12),4,8,10,13,15,20-octaen-9-yl]methanesulfonate) |
| ATTO ™ 550 | Chromis 570N | ATTO ™ Rho14 (6-(2-((3-carboxypropyl)(methyl)carbamoyl)-3,4,5,6-tetrachlorophenyl)-1,11-diethyl-2,2,4,8,10,10-hexamethyl-10,11-dihydro-2H-pyrano[3,2-g:5,6-g']diquinolin-1-ium) |
| ATTO ™ 565 (2-(6,20-diethyl-2-oxa-20-aza-6-azoniapentacyclo[12.8.0.0$^{3,12}$.0$^{5,10}$.0$^{16,21}$]docosa-1(14),3,5,10,12,15,21-heptaen-13-yl)terephthalic acid) | Chromis 577N | BODIPY ® 630/650 ((E)-6-(2-(4-(2-(5,5-difluoro-3-(thiophen-2-yl)-3H,5H-5λ4-dipyrrolo[1,2-c:2',1'-f][1,3,2]diazaborinin-7-yl)vinyl)phenoxy)acetamido)hexanoic acid) |
| BODIPY ® 530/550 (3-(5,5-difluoro-1,3-diphenyl-3H,5H-5λ4-dipyrrolo[1,2-c:2',1'-f][1,3,2]diazaborinin-7-yl)propanoic acid) | Chromis 600N | BODIPY ® 650/665 ((E)-6-(2-(4-(2-(5,5-difluoro-3-(1H-pyrrol-2-yl)-3H,5H-5λ4-dipyrrolo[1,2-c:2',1'-f][1,3,2]diazaborinin-7-yl)vinyl)phenoxy)acetamido)hexanoic acid) |
| BODIPY ® 558/568 (3-(5,5-difluoro-3-(thiophen-2-yl)-3H,5H-5λ4-dipyrrolo[1,2-c:2',1'-f][1,3,2]diazaborinin-7-yl)propanoic acid) | Dyomics ®-590 | CAL Fluor ® Red 635 (6-(2-carboxy-4,5-dimethylphenyl)-1,11-diethyl-2,2,4,8,10,10-hexamethyl-10,11-dihydro-2H-pyrano[3,2-g:5,6-g']diquinolin-1-ium) |
| BODIPY ® 564/570 ((E)-3-(5,5-difluoro-3-styryl-3H,5H-5λ4-dipyrrolo[1,2-c:2',1'-f][1,3,2]diazaborinin-7-yl)propanoic acid) | Dyomics ®-591 | CF ™ 633-V1 |
| CF ™ 514 | Dyomics ®-594 | CF ™ 640R-V1 |
| CF ™ 532 | Dyomics ®-601XL | CF ™ 633 |
| CF ™ 543 | Dyomics ®-605 | CF ™ 640R |
| CF ™ 546 | Dyomics ®-610 | CF ™ 640R-V2 |
| CF ™ 555 | Dyomics ®-615 | CF ™ 660C |
| CF568 | DyLight ® 590-R2 | CF ™ 660R |
| Chromis 530N | DyLight ® 594 | CF ™ 680 |
| Chromis 550A | DyLight ® 610-B1 | CF ™ 680R |
| Chromis 550C | DyLight ® 615-B2 | CF ™ 680R-V1 |
| Chromis 550Z | HiLyte ™ Fluor 594 | Chromeo ™ 642 |
| Chromis 560N | LightCycler ® Red 610 | Chromis 630N |
| Cy ® 3 (indodicarbocyanine 3) | PF594 | Chromis 645A |
| Cy ® 3.5 ((2Z)-2-[(E)-3-[(5-carboxypentyl)-1,1-dimethyl-6,8-disulfobenzo[e]indol-3-ium-2-yl]prop-2-enylidene]-3-ethyl-1,1-dimethyl-8-(trioxidanylsulfanyl)benzo[e]indole-6-sulfonate) | PF594 | Chromis 645A |
| Cy ® 3B (2-{2-[(2,5-dioxopyrrolidin-1-yl)oxy]-2-oxoethyl}-16,16,18,18-tetramethyl-6,7,7a,8a,9,10,16,18-octahydrobenzo[2",3"]indolizino[8",7":5',6']pyrano[3',2':3,4]pyrido[1,2-a]indol-5-ium-14-sulfonate) | PF610 | Chromis 645C |
| Dyomics ®-530 | Quasar ® 570 (2-((1E,3E)-3-(3-(5-carboxypentyl)-1,1-dimethyl-1,3-dihydro-2H-benzo[e]indol-2-ylidene)prop-1-en-1-yl)-3-ethyl- | Chromis 645Z |

TABLE 4-continued

Examples of fluorophores by spectral range

| "Green" 520-570 nm | "Yellow/Orange" 570-620 nm | "Red" 620-670 nm |
|---|---|---|
|  | 1,1-dimethyl-1H-benzo[e]indol-3-ium) |  |
| Dyomics ® -547 | Abberior ® Star 580 | Cy ® 5 (indodicarbocyanine 5) |
| Dyomics-547P1 | Abberior ® Star 600 | Cy ® 5.5 (indodicarbocyanine 5.5) |
| Dyomics ®-548 |  | Dyomics ®-630 |
| Dyomics ®-549P1 |  | Dyomics ®-631 |
| Dyomics ®-550 |  | Dyomics ®-632 |
| Dyomics ®-554 |  | Dyomics ®-633 |
| Dyomics ®-555 |  | Dyomics ®-634 |
| Dyomics ®-556 |  | Dyomics ®-635 |
| Dyomics ®-560 |  | Dyomics ®-636 |
| DyLight ® 521-LS |  | Dyomics ®-647 |
| DyLight ® 530-R2 |  | Dyomics ®-647P1 |
| DyLight ® 543Q |  | Dyomics ®-648 |
| DyLight ® 550 |  | Dyomics ®-648P1 |
| DyLight ® 554-R0 |  | Dyomics ®-649 |
| DyLight ® 554-R1 |  | Dyomics ®-649P1 |
| HiLyte ™ Fluor 532 |  | Dyomics ®-650 |
| HiLyte ™ Fluor 555 |  | Dyomics ®-651 |
| PF532 |  | Dyomics ®-652 |
| PF546 |  | Dyomics ®-654 |
| PF555P |  | DyLight ® 633 |
| PF568 |  | DyLight ® 633-B1 |
| Seta ™ 555 |  | DyLight ® 633-B2 |
| Abberior ® Star 520SXP |  | DyLight ® 650 |
|  |  | DyLight ® 655-B1 |
|  |  | DyLight ® 655-B2 |
|  |  | DyLight ® 655-B3 |
|  |  | DyLight ® 655-B4 |
|  |  | DyLight ® 662Q |
|  |  | DyLight ® 680 |
|  |  | DyLight ® 683Q |
|  |  | HiLyte ™ Fluor 647 |
|  |  | HiLyte ™ Fluor 680 |
|  |  | LightCycler ® 640R |
|  |  | LightCycler ® Red 640 |
|  |  | LightCycler ® Red 670 |
|  |  | PF633P |
|  |  | PF647P |
|  |  | Quasar ® 670 (2-((1E,3E)-5-((E)-1-(5-carboxypentyl)-3,3-dimethylindolin-2-ylidene)penta-1,3-dien-1-yl)-1-ethyl-3,3-dimethyl-3H-indol-1-ium) |
|  |  | Seta ™ 632 |
|  |  | Seta ™ 633 |
|  |  | Seta ™ 650 |
|  |  | Seta ™ 660 |
|  |  | Seta ™ 670 |
|  |  | Seta ™ Tau 647 |
|  |  | Square 635 |
|  |  | Square 650 |
|  |  | Square 660 |
|  |  | Abberior ® Star 635 |
|  |  | Abberior ® Star 635P |
|  |  | Abberior ® Star RED |

In certain embodiments, the luminescent label may comprise a first and second chromophore. In some embodiments, an excited state of the first chromophore is capable of relaxation via an energy transfer to the second chromophore. In some embodiments, the energy transfer is a Förster resonance energy transfer (FRET). Such a FRET pair may be useful for providing a luminescent label with properties that make the label easier to differentiate from amongst a plurality of luminescent labels. In certain embodiments, the FRET pair may absorb excitation energy in a first spectral range and emit luminescence in a second spectral range.

In some embodiments, the luminescent label is attached within a linker molecule described herein (e.g., integrated into an oligomeric or polymeric linker). Table 5 provides several examples of fluorophores compatible with such conjugation strategy in the context of an oligonucleotide strand. As shown, the cyanine-based fluorophores in Table 5 are conjugated to a 3' end of a first strand portion and a 5' end of a second strand portion such that the fluorophore itself forms part of the covalent linkage within the oligonucleotide strand (e.g., the luminescent label is attached without the use of a spacer). It should be appreciated that, in some embodiments, these and similar types of fluorophores can be attached within any class of oligomeric or polymeric structure. For example, in some embodiments, a fluorophore is attached within a peptide via conjugation to a C-terminal end of a first peptide portion and an N-terminal end of a second peptide portion. In some embodiments, a single linker molecule comprises two or more fluorophores attached within the linker (e.g., two, three, four, five, six, or more than six dyes attached within a single linker). In some embodiments, a linker comprises one or more fluorophores attached within the linker and one or more fluorophores attached via a spacer. For example, in some embodiments, a brightly labeled reactant described herein comprises one or more (e.g., one, two, three, four, five, six, or more than six) fluorophores attached within a linker and without a spacer, and one or more (e.g., one, two, three, four, five, six, or more than six) fluorophores attached to the linker via a spacer.

Table 5. Examples of fluorophores for attachment within a linker

TABLE 5

Examples of fluorophores for attachment within a linker

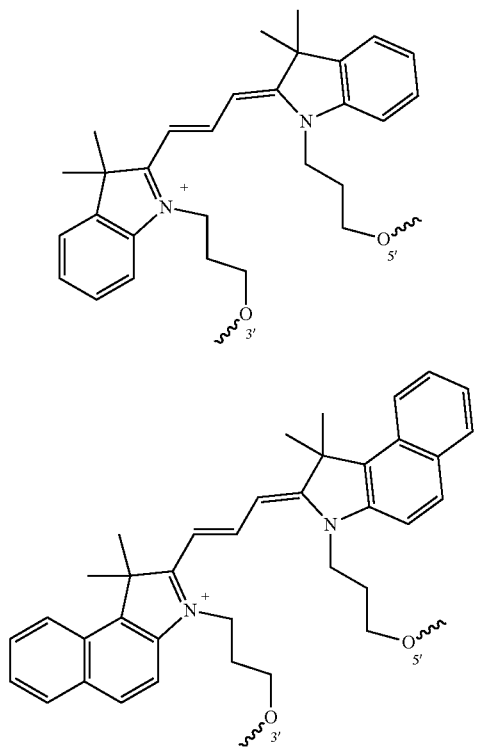

For a set of luminescently labeled molecules (e.g., luminescently labeled nucleotides), the properties of a luminescently labeled FRET pair may allow for selection of a plurality of distinguishable molecules (e.g., nucleotides). In some embodiments, the second chromophore of a FRET pair has a luminescent lifetime distinct from a plurality of other luminescently labeled molecules. In some embodiments, the second chromophore of a FRET pair has a luminescent intensity distinct from a plurality of other luminescently labeled molecules. In some embodiments, the second chromophore of a FRET pair has a luminescent lifetime and luminescent intensity distinct from a plurality of other luminescently labeled molecules. In some embodiments, the second chromophore of a FRET pair emits photons in a spectral range distinct from a plurality of other luminescently labeled molecules. In some embodiments, the first chromophore of a FRET pair has a luminescent lifetime distinct from a plurality of luminescently labeled molecules. In certain embodiments, the FRET pair may absorb excitation energy in a spectral range distinct from a plurality of other luminescently labeled molecules. In certain embodiments, the FRET pair may absorb excitation energy in the same spectral range as one or more of a plurality of other luminescently labeled molecules.

For sequencing reactions, certain combinations of brightly labeled reactants may be preferred. In some embodiments, at least one of the brightly labeled reactants comprises a cyanine dye, or analog thereof. In some embodiments, at least one of the brightly labeled reactants comprises a rhodamine dye, or analog thereof. In some embodiments, at least two of the brightly labeled reactants each comprises a cyanine dye, or analog thereof. In some embodiments, at least two of the brightly labeled reactants each comprises a rhodamine dye, or analog thereof. In some embodiments, at least three of the brightly labeled reactants each comprises a cyanine dye, or analog thereof. In some embodiments, at least three of the brightly labeled reactants each comprises a rhodamine dye, or analog thereof. In some embodiments, at least four of the brightly labeled reactants each comprises a cyanine dye, or analog thereof. In some embodiments, at least four of the brightly labeled reactants each comprises a rhodamine dye, or analog thereof. In some embodiments, three of the brightly labeled reactants each comprises a cyanine dye, or analog thereof, and a fourth brightly labeled reactant comprises a rhodamine dye, or analog thereof. In some embodiments, two of the brightly labeled reactants each comprises a cyanine dye, or analog thereof, and a third, and optionally a fourth, brightly labeled reactant comprises a rhodamine dye, or analog thereof. In some embodiments, three of the brightly labeled reactants each comprises a rhodamine dye, or analog thereof, and a third, and optionally a fourth, brightly labeled reactant comprises a cyanine dye, or analog thereof.

As described herein, a luminescent label is a molecule that absorbs one or more photons and may subsequently emit one or more photons after one or more time durations. The luminescence of the molecule is described by several parameters, including but not limited to luminescent lifetime, absorption spectra, emission spectra, luminescent quantum yield, and luminescent intensity. The terms absorption and excitation are used interchangeably throughout the application. In some embodiments, the terms luminescence and emission are used interchangeably. A typical luminescent molecule may absorb, or undergo excitation by, light at multiple wavelengths. Excitation at certain wavelengths or within certain spectral ranges may relax by a luminescent emission event, while excitation at certain other wavelengths or spectral ranges may not relax by a luminescent emission event. In some embodiments, a luminescent molecule is only suitably excited for luminescence at a single wavelength or within a single spectral range. In some embodiments, a luminescent molecule is suitably excited for luminescence at two or more wavelengths or within two or more spectral ranges. In some embodiments, a molecule is identified by measuring the wavelength of the excitation photon or the absorption spectrum.

The emitted photon from a luminescent emission event will emit at a wavelength within a spectral range of possible wavelengths. Typically the emitted photon has a longer wavelength (e.g., has less energy or is red-shifted) compared to the wavelength of the excitation photon. In certain embodiments, a molecule is identified by measuring the wavelength of an emitted photon. In certain embodiments, a molecule is identified by measuring the wavelength of a plurality of emitted photon. In certain embodiments, a molecule is identified by measuring the emission spectrum.

Luminescent lifetime refers to the time duration between an excitation event and an emission event. In some embodiments, luminescent lifetime is expressed as the constant in an equation of exponential decay. In some embodiments, wherein there are one or more pulse events delivering excitation energy, the time duration is the time between the pulse and the subsequent emission event.

Determination of a luminescent lifetime of a molecule can be performed using any suitable method (e.g., by measuring the lifetime using a suitable technique or by determining time-dependent characteristics of emission). In some embodiments, determining the luminescent lifetime of a molecule comprises determining the lifetime relative to one or more molecules (e.g., different luminescently labeled nucleoside polyphosphates in a sequencing reaction). In some embodiments, determining the luminescent lifetime of a molecule comprises determining the lifetime relative to a reference. In some embodiments, determining the luminescent lifetime of a molecule comprises measuring the lifetime (e.g., fluorescence lifetime). In some embodiments, determining the luminescent lifetime of a molecule comprises determining one or more temporal characteristics that are indicative of lifetime. In some embodiments, the luminescent lifetime of a molecule can be determined based on a distribution of a plurality of emission events (e.g., 1, 2, 3, 4, 5, 6, 7, 8, 9, 10, 11, 12, 13, 14, 15, 16, 17, 18, 19, 20, 30, 40, 50, 60, 70, 80, 90, 100, or more emission events) occurring across one or more time-gated windows relative to an excitation pulse. For example, a luminescent lifetime of a single molecule can be distinguished from a plurality of molecules having different luminescent lifetimes based on the distribution of photon arrival times measured with respect to an excitation pulse.

It should be appreciated that a luminescent lifetime of a single molecule is indicative of the timing of photons emitted after the single molecule reaches an excited state and the single molecule can be distinguished by information indicative of the timing of the photons. Some embodiments may include distinguishing a molecule from a plurality of molecules based on the molecule's luminescent lifetime by measuring times associated with photons emitted by the molecule. The distribution of times may provide an indication of the luminescent lifetime which may be determined from the distribution. In some embodiments, the single molecule is distinguishable from the plurality of molecules based on the distribution of times, such as by comparing the distribution of times to a reference distribution corresponding to a known molecule. In some embodiments, a value for the luminescent lifetime is determined from the distribution of times.

Luminescent quantum yield refers to the fraction of excitation events at a given wavelength or within a given spectral range that lead to an emission event, and is typically less than 1. In some embodiments, the luminescent quantum yield of a molecule described herein is between 0 and about 0.001, between about 0.001 and about 0.01, between about 0.01 and about 0.1, between about 0.1 and about 0.5, between about 0.5 and 0.9, or between about 0.9 and 1. In some embodiments, a molecule is identified by determining or estimating the luminescent quantum yield.

As used herein for single molecules, luminescent intensity refers to the number of emitted photons per unit time that are emitted by a molecule which is being excited by delivery of a pulsed excitation energy. In some embodiments, the luminescent intensity refers to the detected number of emitted photons per unit time that are emitted by a molecule which is being excited by delivery of a pulsed excitation energy, and are detected by a particular sensor or set of sensors.

The luminescent lifetime, luminescent quantum yield, and luminescent intensity may each vary for a given molecule under different conditions. In some embodiments, a single molecule will have a different observed luminescent lifetime, luminescent quantum yield, or luminescent intensity than for an ensemble of the molecules. In some embodiments, a molecule confined in a sample well will have a different observed luminescent lifetime, luminescent quantum yield, or luminescent intensity than for molecules not confined in a sample well. In some embodiments, a luminescent label or luminescent molecule attached to another molecule will have a different luminescent lifetime, luminescent quantum yield, or luminescent intensity than the luminescent label or luminescent molecule not attached to another molecule. In some embodiments, a molecule interacting with a macromolecular complex will have different luminescent lifetime, luminescent quantum yield, or luminescent intensity than a molecule not interacting with a macromolecular complex.

In certain embodiments, a luminescent molecule described in the application absorbs one photon and emits one photon after a time duration. In some embodiments, the luminescent lifetime of a molecule can be determined or estimated by measuring the time duration. In some embodiments, the luminescent lifetime of a molecule can be determined or estimated by measuring a plurality of time durations for multiple pulse events and emission events. In some embodiments, the luminescent lifetime of a molecule can be differentiated amongst the luminescent lifetimes of a plurality of types of molecules by measuring the time duration. In some embodiments, the luminescent lifetime of a molecule can be differentiated amongst the luminescent lifetimes of a plurality of types of molecules by measuring a plurality of time durations for multiple pulse events and emission events. In certain embodiments, a molecule is identified or differentiated amongst a plurality of types of molecules by determining or estimating the luminescent lifetime of the molecule. In certain embodiments, a molecule is identified or differentiated amongst a plurality of types of molecules by differentiating the luminescent lifetime of the molecule amongst a plurality of the luminescent lifetimes of a plurality of types of molecules.

In certain embodiments, the luminescent emission event is a fluorescence. In certain embodiments, the luminescent emission event is a phosphorescence. As used herein, the term luminescence encompasses all luminescent events including both fluorescence and phosphorescence.

Sequencing

Some aspects of the application are useful for sequencing biological polymers, such as nucleic acids and proteins. In some aspects, compositions and techniques described in the application can be used to identify a series of nucleotide or amino acid monomers that are incorporated into a nucleic acid or protein (e.g., by detecting a time-course of incorporation of a series of labeled nucleotide or amino acid monomers). In some embodiments, compositions and techniques described in the application can be used to identify a series of nucleotides that are incorporated into a template-dependent nucleic acid sequencing reaction product synthesized by a polymerase enzyme.

Upon base pairing between a nucleobase of a target nucleic acid and the complementary nucleoside polyphosphate (e.g., dNTP), the polymerase incorporates the dNTP into the newly synthesized nucleic acid strand by forming a phosphodiester bond between the 3' hydroxyl end of the newly synthesized strand and the alpha phosphate of the dNTP. In examples in which the luminescent label conjugated to the dNTP (e.g., through a linker of the application) is a fluorophore, its presence is signaled by excitation and a pulse of emission is detected during and/or after the step of incorporation. For detection labels (e.g., luminescent labels) that are conjugated, through a linker of the application, to the terminal (gamma) phosphate of the dNTP, incorporation of the dNTP into the newly synthesized strand results in release of the beta and gamma phosphates and the linker comprising the detection label, which is free to diffuse in the sample well, resulting in a decrease in emission detected from the fluorophore.

In certain embodiments, the template-dependent nucleic acid sequencing reaction product is synthesized in a sequencing reaction carried out by naturally occurring nucleic acid polymerases. In some embodiments, the polymerase is a mutant or modified variant of a naturally occurring polymerase. In some embodiments, the template-dependent nucleic acid sequencing product will comprise one or more nucleotide segments complementary to the template nucleic acid strand. In one aspect, the application provides a method of determining the sequence of a template (or target) nucleic acid strand by determining the sequence of its complementary nucleic acid strand.

The term "polymerase," as used herein, generally refers to any enzyme (or polymerizing enzyme) capable of catalyzing a polymerization reaction. Examples of polymerases include, without limitation, a nucleic acid polymerase, a transcriptase or a ligase. A polymerase can be a polymerization enzyme. Embodiments directed towards single molecule nucleic acid extension (e.g., for nucleic acid sequencing) may use any polymerase that is capable of synthesizing a nucleic acid complementary to a target nucleic acid molecule. In some embodiments, a polymerase may be a DNA polymerase, an RNA polymerase, a reverse transcriptase, and/or a mutant or altered form of one or more thereof.

Examples of polymerases include, but are not limited to, a DNA polymerase, an RNA polymerase, a thermostable polymerase, a wild-type polymerase, a modified polymerase, E. coli DNA polymerase I, T7 DNA polymerase, bacteriophage T4 DNA polymerase, φ29 (phi29) DNA polymerase, Taq polymerase, Tth polymerase, Tli polymerase, Pfu polymerase, Pwo polymerase, Vent® polymerase, Deep Vent® polymerase, ExTaq™ polymerase, LA Taq™ polymerase, Sso polymerase, Poc polymerase, Pab polymerase, Mth polymerase, ES4 polymerase, Tru polymerase, Tac polymerase, Tne polymerase, Tma polymerase, Tca polymerase, Tih polymerase, Tfi polymerase, Platinum® Taq polymerases, Tbr polymerase, Tfl polymerase, Tth polymerase, PfuTurbo polymerase, Pyrobest™ polymerase, Pwo polymerase, KOD polymerase, Bst polymerase, Sac polymerase, Klenow fragment, polymerase with 3' to 5' exonuclease activity, and variants, modified products and derivatives thereof. In some embodiments, the polymerase is a single subunit polymerase. Non-limiting examples of DNA polymerases and their properties are described in detail in, among other places, DNA Replication 2nd edition, Kornberg and Baker, W. H. Freeman, New York, N.Y. (1991).

In some embodiments, the polymerase is a polymerase with high processivity. However, in some embodiments, the polymerase is a polymerase with reduced processivity. Polymerase processivity generally refers to the capability of a polymerase to consecutively incorporate dNTPs into a nucleic acid template without releasing the nucleic acid template. In some embodiments, the polymerase is a polymerase with low 5'-3' exonuclease activity and/or 3'-5' exonuclease. In some embodiments, the polymerase is modified (e.g., by amino acid substitution) to have reduced 5'-3' exonuclease activity and/or 3'-5' activity relative to a corresponding wild-type polymerase. Further non-limiting examples of DNA polymerases include 9° Nm™ DNA polymerase (New England Biolabs), and a P680G mutant of the Klenow exo-polymerase (Tuske et al. (2000) JBC 275 (31):23759-23768). In some embodiments, a polymerase having reduced processivity provides increased accuracy for sequencing templates containing one or more stretches of nucleotide repeats (e.g., two or more sequential bases of the same type). In some embodiments, the polymerase is a polymerase that has a higher affinity for a labeled nucleotide than for a non-labeled nucleic acid.

In another aspect, the application provides methods of sequencing target nucleic acids by sequencing a plurality of nucleic acid fragments, wherein the target nucleic acid comprises the fragments. In certain embodiments, the method comprises combining a plurality of fragment sequences to provide a sequence or partial sequence for the parent target nucleic acid. In some embodiments, the step of combining is performed by computer hardware and software. The methods described herein may allow for a set of related target nucleic acids, such as an entire chromosome or genome to be sequenced.

During sequencing, a polymerizing enzyme may couple (e.g., attach) to a priming location of a target nucleic acid molecule. The priming location can be a primer that is complementary to a portion of the target nucleic acid molecule. As an alternative, the priming location is a gap or nick that is provided within a double stranded segment of the target nucleic acid molecule. A gap or nick can be from 0 to at least 1, 2, 3, 4, 5, 6, 7, 8, 9, 10, 20, 30, or 40 nucleotides in length. A nick can provide a break in one strand of a double stranded sequence, which can provide a priming location for a polymerizing enzyme, such as, for example, a strand displacing polymerase enzyme.

In some cases, a sequencing primer can be annealed to a target nucleic acid molecule that may or may not be immobilized to a solid support. A solid support can comprise, for example, a sample well (e.g., a nanoaperture, a reaction chamber) on a chip used for nucleic acid sequencing. In some embodiments, a sequencing primer may be immobilized to a solid support and hybridization of the target nucleic acid molecule also immobilizes the target nucleic acid molecule to the solid support. In some embodiments, a polymerase is immobilized to a solid support and soluble primer and target nucleic acid are contacted to the polymerase. However, in some embodiments, a complex comprising a polymerase, a target nucleic acid and a primer is formed in solution and the complex is immobilized to a solid support (e.g., via immobilization of the polymerase, primer, and/or target nucleic acid). In some embodiments, none of the components in a sample well (e.g., a nanoaperture, a reaction chamber) are immobilized to a solid support. For example, in some embodiments, a complex comprising a polymerase, a target nucleic acid, and a primer is formed in solution and the complex is not immobilized to a solid support.

Under appropriate conditions, a polymerase enzyme that is contacted to an annealed primer/target nucleic acid can add or incorporate one or more nucleotides onto the primer, and nucleotides can be added to the primer in a 5' to 3', template-dependent fashion. Such incorporation of nucleotides onto a primer (e.g., via the action of a polymerase) can generally be referred to as a primer extension reaction. Each nucleotide can be associated with a detectable label that can be detected and identified (e.g., based on its luminescent lifetime and/or other characteristics) during the nucleic acid extension reaction and used to determine each nucleotide incorporated into the extended primer and, thus, a sequence of the newly synthesized nucleic acid molecule. Via sequence complementarity of the newly synthesized nucleic acid molecule, the sequence of the target nucleic acid molecule can also be determined. In some cases, annealing of a sequencing primer to a target nucleic acid molecule and incorporation of nucleotides to the sequencing primer can occur at similar reaction conditions (e.g., the same or similar reaction temperature) or at differing reaction conditions (e.g., different reaction temperatures). In some embodiments, sequencing by synthesis methods can include the presence of a population of target nucleic acid molecules (e.g., copies of a target nucleic acid) and/or a step of amplification of the target nucleic acid to achieve a population of target nucleic acids. However, in some embodiments sequencing by synthesis is used to determine the sequence of a single molecule in each reaction that is being evaluated (and nucleic acid amplification is not required to prepare the target template for sequencing). In some embodiments, a plurality of single molecule sequencing reactions are performed in parallel (e.g., on a single chip) according to aspects of the present application. For example, in some embodiments, a plurality of single molecule sequencing reactions are each performed in separate reaction chambers (e.g., nanoapertures, sample wells) on a single chip.

Embodiments are capable of sequencing single nucleic acid molecules with high accuracy and long read lengths, such as an accuracy of at least about 50%, 60%, 70%, 75%, 80%, 85%, 90%, 95%, 96%, 97%, 98%, 99%, 99.9%, 99.99%, 99.999%, or 99.9999%, and/or read lengths greater than or equal to about 10 base pairs (bp), 50 bp, 100 bp, 200 bp, 300 bp, 400 bp, 500 bp, 1000 bp, 10,000 bp, 20,000 bp, 30,000 bp, 40,000 bp, 50,000 bp, or 100,000 bp. In some embodiments, the target nucleic acid molecule used in single molecule sequencing is a single stranded target nucleic acid (e.g., deoxyribonucleic acid (DNA), DNA derivatives, ribonucleic acid (RNA), RNA derivatives) template that is added or immobilized to a sample well (e.g., nanoaperture) containing at least one additional component of a sequencing reaction (e.g., a polymerase such as, a DNA polymerase, a sequencing primer) immobilized or attached to a solid support such as the bottom or side walls of the sample well. The target nucleic acid molecule or the polymerase can be attached to a sample wall, such as at the bottom or side walls of the sample well directly or through a linker. The sample well (e.g., nanoaperture) also can contain any other reagents needed for nucleic acid synthesis via a primer extension reaction, such as, for example suitable buffers, co-factors, enzymes (e.g., a polymerase) and deoxyribonucleoside polyphosphates, such as, e.g., deoxyribonucleoside triphosphates, including deoxyadenosine triphosphate (dATP), deoxycytidine triphosphate (dCTP), deoxyguanosine triphosphate (dGTP), deoxyuridine triphosphate (dUTP), and deoxythymidine triphosphate (dTTP) dNTPs, that include luminescent labels, such as fluorophores, which can be connected to the dNTPs through a linker of the application. In some embodiments, each class of dNTPs (e.g., adenine-containing dNTPs (e.g., dATP), cytosine-containing dNTPs (e.g., dCTP), guanine-containing dNTPs (e.g., dGTP), uracil-containing dNTPs (e.g., dUTPs) and thymine-containing dNTPs (e.g., dTTP)) is conjugated (e.g., through a linker of the application) to a distinct luminescent label such that detection of light emitted from the label indicates the identity of the dNTP that was incorporated into the newly synthesized nucleic acid. A "distinct luminescent label" can, in some embodiments, refer to one dNTP that comprises a different luminescent label (e.g., a different fluorophore) than another dNTP. In some embodiments, a distinct luminescent label refers to one dNTP that comprises a different number of the same or similar luminescent label as another dNTP. In some embodiments, a distinct luminescent label refers to one dNTP that comprises one or more luminescent properties that are detectably different from another dNTP. Emitted light from the luminescent label can be detected and attributed to its appropriate luminescent label (and, thus, associated dNTP) via any suitable device and/or method. The luminescent label may be conjugated (e.g., through a linker of the application) to the dNTP at any position such that the presence of the luminescent label does not inhibit the incorporation of the dNTP into the newly synthesized nucleic acid strand or the activity of the polymerase. In some embodiments, the luminescent label is conjugated (e.g., through a linker of the application) to the terminal phosphate (e.g., the gamma phosphate) of the dNTP.

In some embodiments, the single-stranded target nucleic acid template can be contacted with a sequencing primer, dNTPs, polymerase and other reagents necessary for nucleic acid synthesis. In some embodiments, all appropriate dNTPs can be contacted with the single-stranded target nucleic acid template simultaneously (e.g., all dNTPs are simultaneously present) such that incorporation of dNTPs can occur continuously. In other embodiments, the dNTPs can be contacted with the single-stranded target nucleic acid template sequentially, where the single-stranded target nucleic acid template is contacted with each appropriate dNTP separately, with washing steps in between contact of the single-stranded target nucleic acid template with differing dNTPs. Such a cycle of contacting the single-stranded target nucleic acid template with each dNTP separately followed by washing can be repeated for each successive base position of the single-stranded target nucleic acid template to be identified.

In some embodiments, the sequencing primer anneals to the single-stranded target nucleic acid template and the polymerase consecutively incorporates the dNTPs (or other nucleoside polyphosphate) to the primer based on the single-stranded target nucleic acid template. The unique luminescent label associated with each incorporated dNTP can be excited with the appropriate excitation light during or after incorporation of the dNTP to the primer and its emission can be subsequently detected, using, any suitable device(s) and/or method(s). Detection of a particular emission of light (e.g., having a particular emission lifetime, intensity, spectrum and/or combination thereof) can be attributed to a particular dNTP incorporated. The sequence obtained from the collection of detected luminescent labels can then be used to determine the sequence of the single-stranded target nucleic acid template via sequence complementarity.

In some embodiments, the present disclosure provides methods and compositions that may be advantageously utilized in the technologies described in co-pending U.S. patent application Ser. Nos. 14/543,865, 14/543,867, 14/543,888, 14/821,656, 14/821,686, 14/821,688, 15/161,067, 15/161,088, 15/161,125, 15/255,245, 15/255,303, 15/255,624, 15/261,697, 15/261,724, 15/600,979, 15/846, 967, 15/847,001, 15/971,493, 62/289,019, 62/296,546, 62/310,398, 62/339,790, 62/343,997, 62/344,123, and 62/426,144, the contents of each of which are incorporated herein by reference.

Kits

In yet other aspects, the application provides kits for sequencing a template nucleic acid. In some embodiments, a kit comprises a plurality of types of luminescently labeled nucleotides as described herein. In some embodiments, each type of labeled nucleotide comprises two or more luminescent labels attached to one or more nucleoside polyphosphates via a linker according to the application. In some embodiments, the plurality of nucleotides are selected from the labeled nucleotides depicted in FIGS. 3A-3C, 3E-3G, 4A-4C, 5A-5B, 6A-6C, and 8-10. For example, in some embodiments, the plurality of nucleotides are designed according to the structures shown in FIG. 3G. In some embodiments, the plurality of nucleotides are designed according to the structures shown in FIG. 3B (306), FIG. 3B (308), and FIG. 5A (502). In some embodiments, the kit further comprises a polymerizing enzyme (e.g., a DNA polymerase, as described elsewhere herein). In some embodiments, the kit further comprises a primer complementary to the template nucleic acid being sequenced.

In some aspects, the application provides reaction mixtures comprising one or more of the brightly labeled reactants described herein. In some embodiments, the reaction mixture comprises a mixture added to a sequencing reaction. In some embodiments, the reaction mixture includes a polymerizing enzyme. In some embodiments, the polymerizing enzyme is configured to be immobilized to a solid support (e.g., the bottom of a sample well, as described elsewhere herein). In some embodiments, the reaction mixture comprises a template nucleic acid to be sequenced. In some embodiments, the reaction mixture comprises a primer complementary to a portion of the template nucleic acid. In some embodiments, the reaction mixture comprises one or more components necessary to initiate a sequencing reaction (e.g., a divalent metal ion, such as magnesium or iron). In some embodiments, the reaction mixture comprises one or more components necessary to stabilize a sequencing reaction (e.g., one or more buffering agents, one or more reducing agents, etc.).

EXAMPLES

Example 1: Dye Attachment Strategies with Nucleic Acid Linkers

Various next-generation sequencing technologies implement labeled reaction components. For example, dye-labeled nucleotides can be used to make specific base calls during incorporation events based on the detection or observation of unique luminescent properties corresponding to each base type. These properties, such as lifetime and intensity, must therefore be readily identifiable for each base among a set. Initial efforts into enhancing fluorescence intensity of labeled nucleotides revealed that the brightness of a dye-labeled nucleotide was increased when a second dye molecule was added to the construct. However, fluorescence lifetime was noticeably decreased relative to the singly-labeled variant. In developing improved labeled nucleotides, nucleic acids were investigated as core structures for linking fluorescent dyes to nucleotides.

One potential source of altered fluorescence lifetime in multiply-labeled nucleotides is the extent of interaction between dye molecules of the same construct, which can result in a quenching effect. This possibility was explored further by generating the dye-labeled nucleotides shown in FIG. 8. Two dye molecules (DyLight® 530R2) were connected to a nucleoside polyphosphate via a nucleic acid linker. An unlabeled oligonucleotide strand was hybridized with the labeled oligonucleotide strand to impart rigidity in the nucleic acid linker. A first construct 800 was made using C6-amino-T spacers for dye attachment to the nucleic acid, and a second construct 802 was made using glycolamine spacers for dye attachment.

Analysis of the first construct revealed a fluorescence lifetime of approximately 1.4 ns, while the second construct exhibited a lifetime of approximately 3.5 ns. The measured increase in lifetime with the second construct was attributed to the use of relatively shorter spacers for dye attachment in comparison to the first construct. As shown in FIG. 8, the C6-amino-T spacers of the first construct are of greater length than the glycolamine spacers of the second construct. One possible explanation for the improved lifetime of the second construct is that the shortened spacer length decreased dye-dye interactions by limiting the extent to which the ranges of movement of the attached dyes overlapped.

Example 2: Increased Linker Rigidity Prolongs Fluorescence Lifetime

Following observations that spacer length can affect fluorescence lifetime, potentially due to spatial overlap of dyes, it was thought that a symmetrical arrangement of dyes in a multiply-labeled molecule might have similar effects. A Y-shaped nucleic acid linker was generated and is shown in FIG. 9. The initial construct had three oligonucleotide strands covalently attached via the branched linker shown. Two strands were each terminally attached to a dye molecule (Chromis 530N), whereas the third strand was terminally attached to a nucleoside polyphosphate. The third strand was further hybridized with an unlabeled strand to impart rigidity between the nucleoside polyphosphate and the labeled region. A second version of this construct was generated by hybridization with oligonucleotide component 902, which hybridizes to the first and second strands.

Analysis of the initial construct revealed a fluorescence lifetime of approximately 2.3 ns, while the construct having the additional oligonucleotide component 902 exhibited a lifetime of approximately 4.2 ns. One potential explanation for the measured increase in lifetime with the latter construct is that the oligonucleotide component 902 imparted rigidity in the labeled region. The increased rigidity could conceivably promote dye separation by constraining each dye to a more limited range of movement.

Example 3: Effects of Dye Spacer Length in Constrained Linker Configurations

Geometrically constrained linker configurations were further developed by generating the tris-dye labeled construct shown in FIG. 10. As shown, the nucleic acid linker portion included three main oligonucleotide components. The first component included four oligonucleotide strands covalently attached via the four-way branched linker shown. Three of these strands were each terminally attached to a dye molecule (ATTO™ Rho6G (N-(9-(2-((3-carboxypropyl)(methyl)carbamoyl)phenyl)-6-(ethylamino)-2,7-dimethyl-3H-xanthen-3-ylidene)-N-methylmethanaminium)), whereas the fourth strand was hybridized with a second oligonucleotide component. The second oligonucleotide component was terminally attached to two nucleoside polyphosphates via the branched linker shown. The third oligonucleotide component, which included three oligonucleotide strands covalently attached via the branched linker shown, was hybridized with the three dye-labeled strands of the first component to impart rigidity in the labeled region. Two separate tris-dye constructs having differing spacer lengths were generated according to the boxed area shown in FIG. 10.

The first tris-dye labeled nucleotide construct having a longer spacer (see FIG. 10, boxed area, top) showed a tripling in fluorescence intensity relative to a one-dye labeled nucleotide construct. Additionally, it was noted that lifetime was slightly reduced when compared to a two-dye, one nucleotide construct having the same dye molecule (not shown). Measurements obtained for the second tris-dye labeled nucleotide construct having a shorter spacer (see FIG. 10, boxed area, bottom) showed a slight increase in fluorescence lifetime relative to the first tris-dye labeled construct.

Earlier tris-dye labeled nucleotides produced multiple lifetimes during sequencing reactions, which was thought to be the result of two dyes interacting to produce a first lifetime while the non-interacting dye produced a second lifetime. Importantly, only a single lifetime was observed for either tris-dye labeled molecule shown in FIG. 10 during sequencing reactions.

EQUIVALENTS AND SCOPE

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents, and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding,"

"composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03. It should be appreciated that embodiments described in this document using an open-ended transitional phrase (e.g., "comprising") are also contemplated, in alternative embodiments, as "consisting of" and "consisting essentially of" the feature described by the open-ended transitional phrase. For example, if the disclosure describes "a composition comprising A and B," the disclosure also contemplates the alternative embodiments "a composition consisting of A and B" and "a composition consisting essentially of A and B."

The invention claimed is:

1. A labeled molecule comprising a reactant connected to two or more luminescent labels via a nucleic acid linker, wherein each luminescent label is at least 5 angstroms separated from any other luminescent label, wherein
   (i) at least one luminescent label is integrated within the nucleic acid linker, and wherein the at least one luminescent label that is integrated within the nucleic acid linker is a cyanine-based fluorophore; and/or
   (ii) wherein at least one luminescent label is attached to the nucleic acid linker via a glycolamine spacer molecule, and wherein the labeled nucleotide comprises the structure:

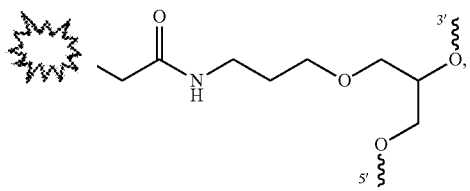

where 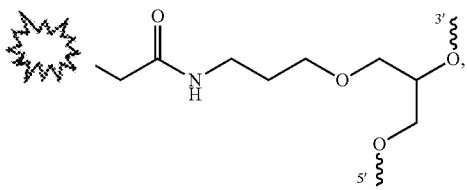 is the at least one luminescent label that is attached to the nucleic acid linker via the glycolamine spacer molecule.

2. The labeled molecule of claim 1, wherein the cyanine-based fluorophore has the chemical structure:

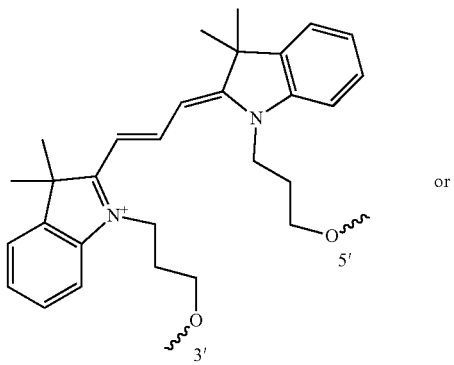

or

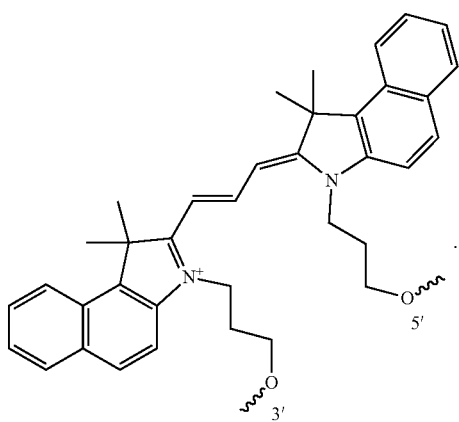

3. The labeled molecule of claim 1, wherein the at least one luminescent label attached to the nucleic acid linker via a glycolamine spacer molecule comprises a rhodamine dye, a BODIPY dye, or a cyanine dye.

4. A labeled nucleotide comprising a nucleoside polyphosphate connected to two or more luminescent labels via a nucleic acid linker, wherein the nucleic acid linker is connected to the terminal phosphate of the nucleoside polyphosphate, wherein each luminescent label is at least 5 angstroms separated from any other luminescent label, wherein
   (i) at least one luminescent label is integrated into the nucleic acid linker, and wherein the at least one luminescent label that is integrated within the nucleic acid linker is a cyanine-based fluorophore; and/or
   (ii) wherein at least one luminescent label is attached to the nucleic acid linker via a glycolamine spacer molecule, and wherein the labeled nucleotide comprises the structure:

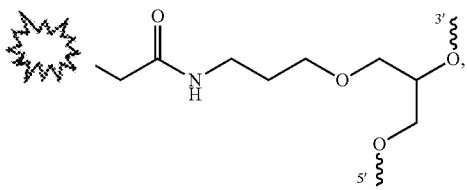

where 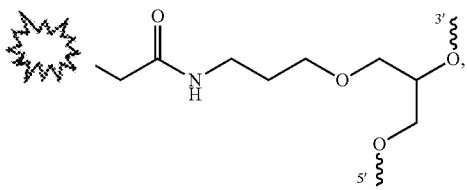 is the at least one luminescent label that is attached to the nucleic acid linker via the glycolamine spacer molecule.

5. The labeled nucleotide of claim 4, wherein each luminescent label comprises a center of mass that is at least 5 angstroms separated from the center of mass of any other luminescent label.

6. The labeled nucleotide of claim 4, wherein the cyanine-based fluorophore has the chemical structure:

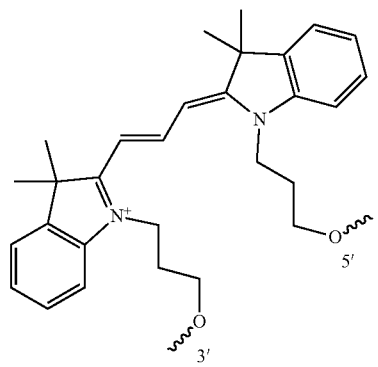

or

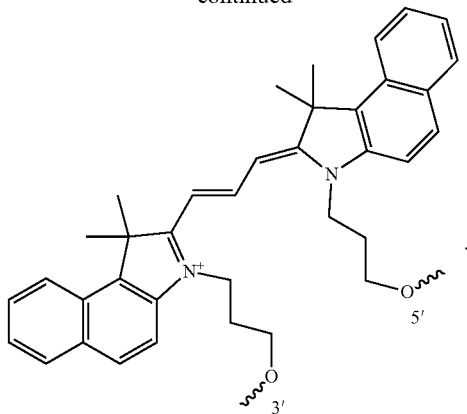

7. The labeled nucleotide of claim 4, wherein the at least one luminescent label attached to the nucleic acid linker via a glycolamine spacer molecule comprises a rhodamine dye, a BODIPY dye, or a cyanine dye.

8. The labeled nucleotide of claim 4, wherein the nucleic acid linker is an oligomer that comprises at least 10 monomeric units.

9. The labeled nucleotide of claim 8, wherein the oligomer comprises fewer than 150, fewer than 100, or fewer than 50 monomeric units.

10. The labeled nucleotide of claim 8, wherein at least one luminescent label is attached to the nucleic acid linker at an attachment site that is at least 5 monomeric units separated from any other attachment site.

11. The labeled nucleotide of claim 4, wherein the nucleic acid linker comprises a first oligonucleotide strand attached to the two or more luminescent labels at two or more attachment sites on the first oligonucleotide strand, and wherein each luminescent label comprises a steric volume having a center point that is at least 5 angstroms separated from that of any other luminescent label.

12. The labeled nucleotide of claim 11, further comprising a second oligonucleotide strand hybridized with the first oligonucleotide strand, wherein the first oligonucleotide strand is attached to the nucleoside polyphosphate.

13. The labeled nucleotide of claim 11, further comprising a second oligonucleotide strand hybridized with the first oligonucleotide strand, wherein the second oligonucleotide strand is attached to the nucleoside polyphosphate.

14. The labeled nucleotide of claim 11, wherein the two or more attachment sites are separated from one another by at least 5 and fewer than 50 bases on the first oligonucleotide strand.

15. The labeled nucleotide of claim 11, wherein each attachment site is at least 2 bases separated from a guanine or a cytosine on the first oligonucleotide strand.

16. The labeled nucleotide of claim 11, wherein at least one attachment site occurs at an abasic site on the first oligonucleotide strand.

17. The labeled nucleotide of claim 11, wherein the first oligonucleotide strand forms one or more stem-loops.

18. The labeled nucleotide of claim 17, wherein a loop region of each stem-loop comprises an attachment site of the two or more attachment sites.

* * * * *